(12) United States Patent
Badawi et al.

(10) Patent No.: US 12,042,428 B2
(45) Date of Patent: *Jul. 23, 2024

(54) OCULAR DELIVERY SYSTEMS AND METHODS

(71) Applicant: Sight Sciences, Inc., Menlo Park, CA (US)

(72) Inventors: David Y. Badawi, Glenview, IL (US); Daniel O'Keeffe, San Francisco, CA (US); Paul Badawi, Atherton, CA (US)

(73) Assignee: SIGHT SCIENCES, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/130,354

(22) Filed: Apr. 3, 2023

(65) Prior Publication Data

US 2023/0233372 A1 Jul. 27, 2023

Related U.S. Application Data

(63) Continuation of application No. 17/827,494, filed on May 27, 2022, now Pat. No. 11,617,679, which is a
(Continued)

(51) Int. Cl.
*A61F 9/00* (2006.01)
*A61F 9/007* (2006.01)

(52) U.S. Cl.
CPC .......... *A61F 9/0008* (2013.01); *A61F 9/0017* (2013.01); *A61F 9/007* (2013.01); *A61F 9/00736* (2013.01); *A61F 9/00781* (2013.01)

(58) Field of Classification Search
CPC ...... A61F 9/0008; A61F 9/0017; A61F 9/007; A61F 9/00736; A61F 9/00781
See application file for complete search history.

(56) References Cited

U.S. PATENT DOCUMENTS

| | | | |
|---|---|---|---|
| 3,159,161 | A | 12/1964 | Ness |
| 4,068,664 | A | 1/1978 | Sharp et al. |

(Continued)

FOREIGN PATENT DOCUMENTS

| | | |
|---|---|---|
| CA | 2244646 A1 | 2/1999 |
| CA | 2567140 A1 | 4/2004 |

(Continued)

OTHER PUBLICATIONS

Ahn, W. et al. (2002). "The "Gauge" System for the Medical Use," Anesth. Analg. 95:1125, with Table 1.
(Continued)

*Primary Examiner* — Jocelin C Tanner
(74) *Attorney, Agent, or Firm* — Cooley LLP

(57) ABSTRACT

Described here are systems and methods for accessing Schlemm's canal and for delivering an ocular device or fluid composition therein. The ocular devices may maintain the patency of Schlemm's canal without substantially interfering with transmural fluid flow across the canal. The fluid composition may be a viscoelastic fluid that is delivered into the canal to facilitate drainage of aqueous humor by disrupting the canal and surrounding trabeculocanalicular tissues. Tools for disrupting these tissues and minimally invasive methods for treating medical conditions associated with elevated intraocular pressure, including glaucoma, are also described.

30 Claims, 21 Drawing Sheets

Related U.S. Application Data continuation of application No. 17/553,671, filed on Dec. 16, 2021, now Pat. No. 11,389,327, which is a continuation of application No. 17/472,147, filed on Sep. 10, 2021, now abandoned, which is a continuation of application No. 17/239,263, filed on Apr. 23, 2021, now Pat. No. 11,116,660, which is a continuation of application No. 17/098,231, filed on Nov. 13, 2020, now abandoned, which is a continuation of application No. 16/189,882, filed on Nov. 13, 2018, now Pat. No. 10,857,027, which is a continuation of application No. 14/816,822, filed on Aug. 3, 2015, now Pat. No. 10,179,066, which is a continuation of application No. 13/644,748, filed on Oct. 4, 2012, now Pat. No. 9,095,412.

(60) Provisional application No. 61/613,274, filed on Mar. 20, 2012.

(56) References Cited

U.S. PATENT DOCUMENTS

| | | |
|---|---|---|
| 4,457,757 A | 7/1984 | Molteno |
| 4,501,274 A | 2/1985 | Skjaerpe |
| 4,553,545 A | 11/1985 | Maass et al. |
| 4,719,825 A | 1/1988 | LaHaye et al. |
| 4,936,825 A | 6/1990 | Ungerleider |
| 4,957,505 A | 9/1990 | McDonald |
| 5,092,837 A | 3/1992 | Ritch et al. |
| 5,180,362 A | 1/1993 | Worst |
| 5,284,476 A | 2/1994 | Koch |
| 5,358,473 A | 10/1994 | Mitchell |
| 5,360,399 A * | 11/1994 | Stegmann ........... A61F 9/00781 604/521 |
| 5,368,572 A | 11/1994 | Shirota |
| 5,486,165 A | 1/1996 | Stegmann |
| 5,540,657 A | 7/1996 | Kurjan et al. |
| 5,558,634 A | 9/1996 | Mitchell |
| 5,569,197 A | 10/1996 | Helmus et al. |
| 5,626,558 A | 5/1997 | Suson |
| 5,639,278 A | 6/1997 | Dereume et al. |
| 5,792,099 A | 8/1998 | DeCamp et al. |
| 5,792,103 A | 8/1998 | Schwartz et al. |
| 5,868,697 A | 2/1999 | Richter et al. |
| 6,036,678 A | 3/2000 | Giungo |
| 6,050,970 A | 4/2000 | Baerveldt |
| 6,050,999 A | 4/2000 | Paraschac et al. |
| 6,299,603 B1 * | 10/2001 | Hecker ................. A61F 9/007 604/289 |
| 6,309,375 B1 | 10/2001 | Glines et al. |
| 6,375,642 B1 | 4/2002 | Grieshaber et al. |
| 6,450,984 B1 | 9/2002 | Lynch et al. |
| 6,491,670 B1 | 12/2002 | Toth et al. |
| 6,494,857 B1 | 12/2002 | Neuhann |
| 6,508,779 B1 | 1/2003 | Suson |
| 6,524,275 B1 | 2/2003 | Lynch et al. |
| 6,533,768 B1 | 3/2003 | Hill |
| 6,616,996 B1 | 9/2003 | Keith et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,726,676 B2 | 4/2004 | Stegmann et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,840,952 B2 | 1/2005 | Saker et al. |
| 6,843,792 B2 | 1/2005 | Nishtala et al. |
| 6,893,415 B2 | 5/2005 | Madsen et al. |
| 6,955,656 B2 | 10/2005 | Bergheim et al. |
| 6,962,573 B1 | 11/2005 | Wilcox |
| 7,094,225 B2 | 8/2006 | Tu et al. |
| 7,135,009 B2 | 11/2006 | Tu et al. |
| 7,186,232 B1 | 3/2007 | Smedley et al. |
| 7,192,412 B1 | 3/2007 | Zhou et al. |
| 7,207,980 B2 | 4/2007 | Christian et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,588,597 B2 | 9/2009 | Frid |
| 7,713,228 B2 | 5/2010 | Robin |
| 7,740,604 B2 | 6/2010 | Schieber et al. |
| 7,806,847 B2 | 10/2010 | Wilcox |
| 7,850,637 B2 | 12/2010 | Lynch et al. |
| 7,867,205 B2 | 1/2011 | Bergheim et al. |
| 7,909,789 B2 | 3/2011 | Badawi et al. |
| 7,951,155 B2 | 5/2011 | Smedley et al. |
| 7,967,772 B2 | 6/2011 | McKenzie et al. |
| 8,034,105 B2 | 10/2011 | Stegmann et al. |
| 8,075,511 B2 | 12/2011 | Tu et al. |
| 8,109,896 B2 | 2/2012 | Nissan et al. |
| 8,123,729 B2 | 2/2012 | Yamamoto et al. |
| 8,133,208 B2 | 3/2012 | Hetherington |
| 8,137,307 B2 | 3/2012 | Tennican et al. |
| 8,152,752 B2 | 4/2012 | Lynch et al. |
| 8,172,899 B2 | 5/2012 | Silvestrini et al. |
| 8,267,882 B2 | 9/2012 | Euteneuer et al. |
| 8,273,050 B2 | 9/2012 | Bergheim et al. |
| 8,282,592 B2 | 10/2012 | Schieber et al. |
| 8,287,482 B2 | 10/2012 | Badawi et al. |
| 8,333,742 B2 | 12/2012 | Bergheim et al. |
| 8,337,509 B2 | 12/2012 | Schieber et al. |
| 8,348,924 B2 | 1/2013 | Christian et al. |
| 8,366,653 B2 | 2/2013 | Shareef et al. |
| 8,372,026 B2 | 2/2013 | Schieber et al. |
| 8,388,568 B2 | 3/2013 | Lynch et al. |
| 8,403,920 B2 | 3/2013 | Lind et al. |
| 8,414,518 B2 | 4/2013 | Schieber et al. |
| 8,414,636 B2 | 4/2013 | Nabulsi et al. |
| 8,425,449 B2 | 4/2013 | Wardle et al. |
| 8,425,450 B2 | 4/2013 | Wilcox |
| 8,439,972 B2 | 5/2013 | Badawi et al. |
| 8,444,589 B2 | 5/2013 | Silvestrini |
| 8,491,549 B2 | 7/2013 | Conston et al. |
| 8,512,321 B2 | 8/2013 | Baerveldt et al. |
| 8,512,404 B2 | 8/2013 | Frion et al. |
| 8,529,622 B2 | 9/2013 | Badawi et al. |
| 8,540,659 B2 | 9/2013 | Berlin |
| 8,540,681 B2 | 9/2013 | Hetherington |
| 8,540,761 B2 | 9/2013 | Rabkin et al. |
| 8,545,431 B2 | 10/2013 | Rickard |
| 8,568,391 B2 | 10/2013 | Kearns et al. |
| 8,617,094 B2 | 12/2013 | Smedley et al. |
| 8,657,776 B2 | 2/2014 | Wardle et al. |
| 8,663,150 B2 | 3/2014 | Wardle et al. |
| 8,715,266 B2 | 5/2014 | Bos |
| 8,734,377 B2 | 5/2014 | Schieber et al. |
| 8,747,299 B2 | 6/2014 | Grieshaber |
| 8,771,217 B2 | 7/2014 | Lynch et al. |
| 8,801,648 B2 | 8/2014 | Bergheim et al. |
| 8,808,222 B2 | 8/2014 | Schieber et al. |
| 8,827,990 B2 | 9/2014 | Van Valen et al. |
| 8,852,137 B2 | 10/2014 | Horvath et al. |
| 8,876,898 B2 | 11/2014 | Badawi et al. |
| 8,888,734 B2 | 11/2014 | Nissan et al. |
| 8,894,603 B2 | 11/2014 | Badawi et al. |
| 8,926,546 B2 | 1/2015 | Wilcox |
| 8,961,447 B2 | 2/2015 | Schieber et al. |
| 9,039,650 B2 | 5/2015 | Schieber et al. |
| 9,044,301 B1 | 6/2015 | Pinchuk et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 9,095,412 B2 | 8/2015 | Badawi et al. |
| 9,107,729 B2 | 8/2015 | Sorensen et al. |
| 9,125,723 B2 | 9/2015 | Horvath et al. |
| 9,155,655 B2 | 10/2015 | Schieber et al. |
| 9,192,516 B2 | 11/2015 | Horvath et al. |
| 9,211,213 B2 | 12/2015 | Wardle et al. |
| 9,216,109 B2 * | 12/2015 | Badawi ............... A61F 9/00736 |
| 9,220,632 B2 | 12/2015 | Smedley et al. |
| 9,226,850 B2 | 1/2016 | Baerveldt et al. |

(56) References Cited

U.S. PATENT DOCUMENTS

| | | |
|---|---|---|
| 9,226,852 B2 | 1/2016 | Schieber et al. |
| 9,301,875 B2 | 4/2016 | Tu et al. |
| 9,326,891 B2 | 5/2016 | Horvath et al. |
| 9,339,514 B2 | 5/2016 | Bos et al. |
| 9,351,874 B2 | 5/2016 | Schieber et al. |
| 9,358,155 B2 | 6/2016 | Sorensen et al. |
| 9,358,156 B2 | 6/2016 | Wardle et al. |
| 9,370,443 B2 | 6/2016 | Badawi et al. |
| 9,381,111 B2 | 7/2016 | Hickingbotham et al. |
| 9,402,767 B2 | 8/2016 | Schieber et al. |
| 9,486,361 B2 | 11/2016 | Badawi et al. |
| 9,492,319 B2 | 11/2016 | Grieshaber et al. |
| 9,492,320 B2 | 11/2016 | Lynch et al. |
| 9,510,973 B2 | 12/2016 | Wardle |
| 9,855,167 B2 | 1/2018 | Badawi et al. |
| 9,889,258 B2 | 2/2018 | Bengtsson et al. |
| 9,895,258 B2 | 2/2018 | Badawi et al. |
| 10,154,924 B2 | 12/2018 | Clauson et al. |
| 10,179,066 B2 | 1/2019 | Badawi et al. |
| 10,299,958 B2 | 5/2019 | Badawi et al. |
| 10,314,742 B2 | 6/2019 | Badawi et al. |
| 10,398,597 B2 | 9/2019 | Badawi et al. |
| 10,406,030 B2 | 9/2019 | Badawi et al. |
| 10,857,027 B2 | 12/2020 | Badawi et al. |
| 10,888,453 B2 | 1/2021 | Badawi et al. |
| 10,905,591 B1 | 2/2021 | Ianchulev |
| 11,090,188 B2 | 8/2021 | Badawi et al. |
| 11,116,660 B2 | 9/2021 | Badawi et al. |
| 11,166,847 B2 | 11/2021 | Badawi et al. |
| 11,259,961 B2 | 3/2022 | Ianchulev |
| 11,344,447 B2 | 5/2022 | Badawi et al. |
| 11,389,327 B2 | 7/2022 | Badawi et al. |
| 11,389,328 B2 | 7/2022 | Badawi et al. |
| 11,419,762 B2 | 8/2022 | Lanchulev |
| 11,419,886 B2 | 8/2022 | Badawi et al. |
| 11,471,324 B2 | 10/2022 | Badawi et al. |
| 11,504,270 B1 | 11/2022 | Badawi et al. |
| 11,617,679 B2 | 4/2023 | Badawi et al. |
| 2001/0014788 A1 | 8/2001 | Morris |
| 2002/0013546 A1 | 1/2002 | Grieshaber et al. |
| 2002/0013572 A1 | 1/2002 | Berlin |
| 2002/0055753 A1 | 5/2002 | Silvestrini |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2002/0165478 A1 | 11/2002 | Gharib et al. |
| 2003/0060447 A1 | 3/2003 | Karakelle et al. |
| 2003/0060752 A1 | 3/2003 | Bergheim et al. |
| 2003/0060873 A1 | 3/2003 | Gertner et al. |
| 2003/0120200 A1 | 6/2003 | Bergheim et al. |
| 2003/0181848 A1 | 9/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0044310 A1 | 3/2004 | Suzuki |
| 2004/0102719 A1 | 5/2004 | Keith et al. |
| 2004/0102729 A1 | 5/2004 | Haffner et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2005/0038334 A1 | 2/2005 | Lynch et al. |
| 2005/0055082 A1 | 3/2005 | Ben Muvhar et al. |
| 2005/0090807 A1 | 4/2005 | Lynch et al. |
| 2005/0101967 A1 | 5/2005 | Weber et al. |
| 2005/0125003 A1* | 6/2005 | Pinchuk ............ A61F 9/00781 604/8 |
| 2005/0154399 A1 | 7/2005 | Weber et al. |
| 2005/0165363 A1 | 7/2005 | Judson et al. |
| 2005/0171507 A1* | 8/2005 | Christian ............ A61F 9/00781 604/524 |
| 2005/0192527 A1 | 9/2005 | Gharib et al. |
| 2005/0209549 A1 | 9/2005 | Bergheim et al. |
| 2005/0250788 A1 | 11/2005 | Tu et al. |
| 2005/0266047 A1 | 12/2005 | Tu et al. |
| 2005/0267555 A1 | 12/2005 | Marnfeldt et al. |
| 2005/0277864 A1 | 12/2005 | Haffner et al. |
| 2005/0288619 A1 | 12/2005 | Gharib et al. |
| 2006/0032507 A1 | 2/2006 | Tu |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0149194 A1* | 7/2006 | Conston ............ A61B 17/3421 604/294 |
| 2006/0155300 A1 | 7/2006 | Stamper et al. |
| 2006/0173077 A1 | 8/2006 | Cagle |
| 2006/0173397 A1 | 8/2006 | Tu et al. |
| 2006/0173446 A1 | 8/2006 | Dacquay et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0217741 A1 | 9/2006 | Ghannoum |
| 2006/0241580 A1 | 10/2006 | Mittelstein et al. |
| 2007/0073275 A1 | 3/2007 | Conston et al. |
| 2007/0106236 A1 | 5/2007 | Coroneo |
| 2007/0167910 A1 | 7/2007 | Tennican et al. |
| 2007/0191863 A1 | 8/2007 | De Juan, Jr. et al. |
| 2007/0260173 A1 | 11/2007 | Boukhny et al. |
| 2007/0276420 A1 | 11/2007 | Sorensen et al. |
| 2008/0004596 A1 | 1/2008 | Yun et al. |
| 2008/0058704 A1 | 3/2008 | Hee et al. |
| 2008/0058760 A1 | 3/2008 | Agerup |
| 2008/0082078 A1 | 4/2008 | Berlin |
| 2008/0108934 A1 | 5/2008 | Berlin |
| 2008/0300574 A1 | 12/2008 | Belson et al. |
| 2009/0036827 A1* | 2/2009 | Cazzini ............ A61F 9/0017 604/60 |
| 2009/0043321 A1 | 2/2009 | Conston et al. |
| 2009/0082860 A1 | 3/2009 | Schieber et al. |
| 2009/0082862 A1 | 3/2009 | Schieber et al. |
| 2009/0082863 A1 | 3/2009 | Schieber et al. |
| 2009/0132040 A1 | 5/2009 | Frion et al. |
| 2009/0227934 A1 | 9/2009 | Euteneuer et al. |
| 2009/0247955 A1 | 10/2009 | Yamamoto et al. |
| 2009/0287143 A1 | 11/2009 | Line |
| 2009/0287233 A1 | 11/2009 | Huculak |
| 2010/0019177 A1 | 1/2010 | Luckevich |
| 2010/0087774 A1 | 4/2010 | Haffner et al. |
| 2010/0121248 A1 | 5/2010 | Yu et al. |
| 2010/0173866 A1 | 7/2010 | Hee et al. |
| 2010/0179652 A1 | 7/2010 | Yamamoto et al. |
| 2010/0222802 A1 | 9/2010 | Gillespie |
| 2010/0241046 A1 | 9/2010 | Pinchuk et al. |
| 2010/0262174 A1 | 10/2010 | Sretavan et al. |
| 2011/0009874 A1 | 1/2011 | Wardle et al. |
| 2011/0009958 A1 | 1/2011 | Wardle et al. |
| 2011/0098809 A1* | 4/2011 | Wardle ............ A61F 9/00781 623/6.12 |
| 2011/0224597 A1 | 9/2011 | Stegmann et al. |
| 2011/0238009 A1 | 9/2011 | Meron et al. |
| 2011/0238075 A1 | 9/2011 | Clauson et al. |
| 2011/0306915 A1 | 12/2011 | De Juan, Jr. et al. |
| 2012/0010702 A1 | 1/2012 | Stegmann et al. |
| 2012/0123315 A1 | 5/2012 | Horvath et al. |
| 2012/0123434 A1 | 5/2012 | Grabner et al. |
| 2012/0136306 A1 | 5/2012 | Bartha |
| 2012/0165720 A1 | 6/2012 | Horvath et al. |
| 2012/0191064 A1 | 7/2012 | Conston et al. |
| 2012/0197175 A1 | 8/2012 | Horvath et al. |
| 2012/0203160 A1 | 8/2012 | Kahook et al. |
| 2012/0220917 A1 | 8/2012 | Silvestrini et al. |
| 2012/0310072 A1 | 12/2012 | Grieshaber |
| 2012/0310137 A1 | 12/2012 | Silvestrini |
| 2012/0325704 A1 | 12/2012 | Kerns et al. |
| 2013/0041346 A1 | 2/2013 | Alon |
| 2013/0158462 A1 | 6/2013 | Wardle et al. |
| 2013/0245600 A1 | 9/2013 | Yamamoto et al. |

(56) References Cited

U.S. PATENT DOCUMENTS

| | | |
|---|---|---|
| 2013/0274655 A1 | 10/2013 | Jennings et al. |
| 2014/0066833 A1 | 3/2014 | Yaron et al. |
| 2014/0081194 A1 | 3/2014 | Burns et al. |
| 2014/0121584 A1 | 5/2014 | Wardle et al. |
| 2014/0128847 A1 | 5/2014 | Lopez |
| 2014/0135916 A1 | 5/2014 | Clauson et al. |
| 2014/0163448 A1 | 6/2014 | Lind et al. |
| 2014/0171852 A1 | 6/2014 | Khor |
| 2014/0194916 A1 | 7/2014 | Ichikawa |
| 2014/0213958 A1 | 7/2014 | Clauson et al. |
| 2014/0236066 A1 | 8/2014 | Horvath et al. |
| 2014/0276332 A1 | 9/2014 | Crimaldi et al. |
| 2014/0288485 A1 | 9/2014 | Berlin |
| 2014/0309599 A1 | 10/2014 | Schaller |
| 2014/0323995 A1 | 10/2014 | Clauson et al. |
| 2014/0364791 A1 | 12/2014 | Stegmann et al. |
| 2015/0005623 A1 | 1/2015 | Grover et al. |
| 2015/0011926 A1 | 1/2015 | Reitsamer et al. |
| 2015/0051699 A1 | 2/2015 | Badawi et al. |
| 2015/0065940 A1 | 3/2015 | Rangel-Friedman et al. |
| 2015/0080783 A1 | 3/2015 | Berlin |
| 2015/0112372 A1 | 4/2015 | Perez Grossmann |
| 2015/0119787 A1 | 4/2015 | Wardle et al. |
| 2015/0125328 A1 | 5/2015 | Bourne et al. |
| 2015/0133946 A1 | 5/2015 | Horvath et al. |
| 2015/0148615 A1 | 5/2015 | Brennan et al. |
| 2015/0216729 A1 | 8/2015 | Doci |
| 2015/0223981 A1 | 8/2015 | Smedley et al. |
| 2015/0223983 A1 | 8/2015 | Schieber et al. |
| 2015/0250649 A1 | 9/2015 | Euteneuer et al. |
| 2015/0257932 A1 | 9/2015 | Pinchuk et al. |
| 2015/0282982 A1 | 10/2015 | Schieber et al. |
| 2015/0313758 A1 | 11/2015 | Wilcox |
| 2015/0320596 A1 | 11/2015 | Gifford, III et al. |
| 2015/0374545 A1 | 12/2015 | Horvath et al. |
| 2016/0022486 A1 | 1/2016 | Clauson et al. |
| 2016/0051408 A1 | 2/2016 | Baerveldt et al. |
| 2016/0095985 A1 | 4/2016 | Novak |
| 2016/0100980 A1 | 4/2016 | Badawi et al. |
| 2016/0106589 A1 | 4/2016 | Mittelstein et al. |
| 2016/0135994 A1 | 5/2016 | Romoda et al. |
| 2016/0143778 A1 | 5/2016 | Aljuri et al. |
| 2016/0151204 A1 | 6/2016 | Haffner et al. |
| 2016/0158453 A1 | 6/2016 | Oakley et al. |
| 2016/0220417 A1 | 8/2016 | Schieber et al. |
| 2016/0220418 A1 | 8/2016 | Sorensen et al. |
| 2016/0256317 A1 | 9/2016 | Horvath et al. |
| 2016/0256323 A1 | 9/2016 | Horvath et al. |
| 2016/0287438 A1 | 10/2016 | Badawi et al. |
| 2016/0302965 A1 | 10/2016 | Erickson et al. |
| 2016/0331588 A1 | 11/2016 | Ambati et al. |
| 2016/0346006 A1 | 12/2016 | Hickengbotham et al. |
| 2016/0354248 A1 | 12/2016 | Kahook |
| 2017/0202677 A1 | 7/2017 | Badawi et al. |
| 2017/0258507 A1 | 9/2017 | Hetherington |
| 2019/0314200 A1 | 10/2019 | Badawi et al. |
| 2020/0038243 A1 | 2/2020 | Badawi et al. |
| 2020/0121503 A1 | 4/2020 | Badawi et al. |
| 2021/0236313 A1 | 8/2021 | Badawi et al. |
| 2021/0386584 A1 | 12/2021 | Badawi et al. |
| 2022/0104967 A1 | 4/2022 | Badawi et al. |
| 2022/0160668 A1 | 5/2022 | Badawi et al. |
| 2022/0168146 A1 | 6/2022 | Badawi et al. |
| 2022/0280339 A1 | 9/2022 | Badawi et al. |
| 2022/0280340 A1 | 9/2022 | Badawi et al. |
| 2022/0354695 A1 | 11/2022 | Badawi et al. |
| 2023/0118632 A1 | 4/2023 | Arnoldussen et al. |
| 2023/0181355 A1 | 6/2023 | Badawi et al. |
| 2023/0233371 A1 | 7/2023 | Badawi et al. |

FOREIGN PATENT DOCUMENTS

| | | |
|---|---|---|
| CA | 2778452 A1 | 4/2011 |
| CN | 1678407 A | 10/2005 |
| CN | 1909859 A | 2/2007 |
| CN | 101505830 A | 8/2009 |
| CN | 201824103 U | 5/2011 |
| CN | 102123713 A | 7/2011 |
| CN | 102202706 A | 9/2011 |
| CN | 202400240 U | 8/2012 |
| EP | 2 830 553 B1 | 12/2017 |
| JP | 03-168154 A | 7/1991 |
| JP | 2002-541976 A | 12/2002 |
| JP | 2003-180730 A | 7/2003 |
| JP | 2005-510317 A | 4/2005 |
| JP | 2005-538809 A | 12/2005 |
| JP | 2007-527251 A | 9/2007 |
| JP | 2012-527318 A | 11/2012 |
| JP | 2013-512707 A | 4/2013 |
| JP | 2014-036867 A | 2/2014 |
| JP | 2014-533600 A | 12/2014 |
| WO | WO-00/64391 A1 | 11/2000 |
| WO | WO-00/64393 A1 | 11/2000 |
| WO | WO-01/97727 A1 | 12/2001 |
| WO | WO-02/36052 A1 | 5/2002 |
| WO | WO-03/045582 A1 | 6/2003 |
| WO | WO-2004/026361 A1 | 4/2004 |
| WO | WO-2004/069664 A2 | 8/2004 |
| WO | WO-2004/069664 A3 | 8/2004 |
| WO | WO-2005/016418 A1 | 2/2005 |
| WO | WO-2005/105197 A2 | 11/2005 |
| WO | WO-2005/105197 A3 | 11/2005 |
| WO | WO-2005/107664 A2 | 11/2005 |
| WO | WO-2005/107664 A3 | 11/2005 |
| WO | WO-2005/117752 A1 | 12/2005 |
| WO | WO-2006/066103 A2 | 6/2006 |
| WO | WO-2006/066103 A3 | 6/2006 |
| WO | WO-2008/002377 A1 | 1/2008 |
| WO | WO-2009/042596 A2 | 4/2009 |
| WO | WO-2009/042596 A3 | 4/2009 |
| WO | WO-2009/067369 A1 | 5/2009 |
| WO | WO-2009/111645 A1 | 9/2009 |
| WO | WO-2010/065970 A1 | 6/2010 |
| WO | WO-2011/006078 A1 | 1/2011 |
| WO | WO-2011/006113 A1 | 1/2011 |
| WO | WO-2011/050360 A1 | 4/2011 |
| WO | WO-2011/097408 A1 | 8/2011 |
| WO | WO-2011/106781 A1 | 9/2011 |
| WO | WO-2013/141898 A1 | 9/2013 |
| WO | WO-2016/042162 A1 | 3/2016 |
| WO | WO-2016/159999 A1 | 10/2016 |

OTHER PUBLICATIONS

Aragona, P. et al. (2002). "Long Term Treatment with Sodium Hyaluronate-Containing Artificial Tears Reduces Ocular Surface Damage in Patients with Dry Eye," Br. J. Ophthalmol. 86:181-184.

Bahler, C.K. et al. (2004). "Trabecular bypass stents decrease intraocular pressure in cultured human anterior segments," Am. J. Ophthalmol. 138:988-994.

Balazs, E.A. et al. (1972). "Hyaluronic Acid and Replacement of Vitreous and Aqueous Humor," Modern Problems in Ophthalmology 10:3-21.

Boyle, E.L. (Feb. 1, 2006). "New Glaucoma Devices Take Different Approaches to IOP Lowering," Ocular Surgery News U.S. Edition, located at <http://www.osnsupersite.com/view.aspx?rid=12436>, last visited on Apr. 23, 2012, 4 pages, revisited on Apr. 19, 2016, 5 pages.

Butany, J. et al. (2005). "Coronary artery stents; identification and evaluation," J. Clin. Pathol. 58:795-804.

ClinicalTrials.Gov (2006). A study of the trabecular micro-bypass stent in combination with cataract surgery in subjects with open angle glaucoma, NCT00323284, 6 total pages.

Colombo, A. et al. (2002). "Selection of coronary stents," J. Am. Coll. Cardiol. 40:1021-1033.

Corrected Notice of Allowability mailed on Nov. 23, 2018, for U.S. Appl. No. 14/816,822, filed Aug. 3, 2015, 2 pages.

Corrected Notice of Allowability mailed on Dec. 12, 2018, for U.S. Appl. No. 14/816,822, filed Aug. 3, 2015, 2 pages.

Corrected Notice of Allowability mailed on Feb. 21, 2019, for U.S. Appl. No. 14/675,580, filed Mar. 31, 2015, 6 pages.

(56) References Cited

OTHER PUBLICATIONS

Corrected Notice of Allowability mailed on Apr. 3, 2019, for U.S. Appl. No. 14/675,580, filed Mar. 31, 2015, 3 pages.
Corrected Notice of Allowability mailed on Oct. 12, 2021, for U.S. Appl. No. 16/532,260, filed Aug. 5, 2019, 2 pages.
Corrected Notice of Allowability mailed on Apr. 15, 2022, for U.S. Appl. No. 17/239,270, filed Apr. 23, 2021, 2 pages.
Corrected Notice of Allowability mailed on Oct. 14, 2022, for U.S. Appl. No. 17/033,408, filed Sep. 25, 2020, 2 pages.
Corrected Notice of Allowability mailed on Mar. 3, 2023, for U.S. Appl. No. 17/827,494, filed May 27, 2022, 5 pages.
Drusedau, M.U.H. et al. (2000). "Viscocanalostomy for primary open-angle glaucoma: The gross Pankow experience," J. Cataract Refract. Surg. 26:1367-1373.
Extended European Search Report mailed Apr. 22, 2015, for EP Patent Application No. 11 740 372.5, filed Feb. 3, 2011, six pages.
Extended European Search Report mailed on Jun. 9, 2016, for European Patent Application No. 16 155 079.3, filed on May 31, 2007, 7 pages.
Extended European Search Report mailed on May 17, 2011, for European Patent Application No. 11 162 487.0, filed on May 31, 2007, 6 pages.
Extended European Search Report mailed on Mar. 24, 2016, for European Patent Application No. 12 871 982.0, filed on Oct. 4, 2012, 7 pages.
Extended European Search Report mailed on Nov. 20, 2018, for European Patent Application No. 15 888 007.0, filed on Mar. 31, 2015, 9 pages.
Extended European Search Report mailed on Feb. 4, 2022, for European Patent Application No. 21 179 625.5, filed on Mar. 31, 2015, 8 pages.
Final Office Action mailed on Nov. 1, 2010, for U.S. Appl. No. 11/475,523, filed Jun. 26, 2006, 12 pages.
Final Office Action mailed on Jul. 19, 2012, for U.S. Appl. No. 13/245,811, filed Sep. 26, 2011, 6 pages.
Final Office Action mailed on Feb. 1, 2013, for U.S. Appl. No. 13/020,706, filed Feb. 3, 2011, 6 pages.
Final Office Action mailed on Sep. 15, 2014, for U.S. Appl. No. 13/025,112, filed Feb. 10, 2011, 13 pages.
Final Office Action mailed on Sep. 20, 2013, for U.S. Appl. No. 13/644,780, filed Oct. 4, 2012, 16 pages.
Final Office Action mailed on Nov. 12, 2013, for U.S. Appl. No. 13/644,748, filed Oct. 4, 2012, 8 pages.
Final Office Action mailed on Jan. 8, 2014, for U.S. Appl. No. 13/644,758, filed Oct. 4, 2012, 8 pages.
Final Office Action mailed on Sep. 3, 2014, for U.S. Appl. No. 13/644,758, filed Oct. 4, 2012, 8 pages.
Final Office Action mailed on Apr. 23, 2015, for U.S. Appl. No. 14/527,292, filed Oct. 29, 2014, 8 pages.
Final Office Action mailed on Aug. 19, 2015, for U.S. Appl. No. 13/445,816, filed Apr. 12, 2012, 6 pages.
Final Office Action mailed on Mar. 9, 2016, for U.S. Appl. No. 14/539,648, filed Nov. 12, 2014, 11 pages.
Final Office Action mailed on Oct. 3, 2016, for U.S. Appl. No. 13/644,769, filed Oct. 4, 2012, 27 pages.
Final Office Action mailed on May 18, 2017, for U.S. Appl. No. 14/539,648, filed Nov. 12, 2014, 14 pages.
Final Office Action mailed on Jan. 29, 2018, for U.S. Appl. No. 14/973,620, filed Dec. 17, 2015, 19 pages.
Final Office Action mailed on Apr. 6, 2018, for U.S. Appl. No. 15/683,652, filed Aug. 22, 2017, 11 pages.
Final Office Action mailed on Jun. 1, 2018, for U.S. Appl. No. 14/816,822, filed Aug. 3, 2015, 6 pages.
Final Office Action mailed on Oct. 19, 2018, for U.S. Appl. No. 15/683,652, filed Aug. 22, 2017, 8 pages.
Final Office Action mailed on Apr. 19, 2019, for U.S. Appl. No. 14/973,620, filed Dec. 17, 2015, 12 pages.
Final Office Action mailed on Jun. 9, 2020, for U.S. Appl. No. 15/854,126, filed Dec. 26, 2017, 9 pages.
Final Office Action mailed on Jun. 9, 2020, for U.S. Appl. No. 16/189,882, filed Nov. 13, 2018, 12 pages.
Final Office Action mailed on Apr. 1, 2021, for U.S. Appl. No. 16/532,260, filed Aug. 5, 2019, 8 pages.
Final Office Action mailed on Dec. 21, 2021, for U.S. Appl. No. 17/239,270, filed Apr. 23, 2021, 14 pages.
Final Office Action mailed on Dec. 27, 2022, for U.S. Appl. No. 17/827,485, filed May 27, 2022, 30 pages.
Glaukos iStent (2022). iStent inject® W, 9 total pages.
Guerrero, A.H et al. (2000). "Complications of glaucoma drainage implant surgery," Int. Ophthalmol. Clin. 40:149-163.
International Search Report mailed on Nov. 30, 2007, for PCT Application No. PCT/US2007/013038, filed on May 31, 2007, 4 pages.
International Search Report mailed on Apr. 5, 2011, for PCT Application No. PCT/US2011/023643, filed on Feb. 3, 2011, 2 pages.
International Search Report mailed on Feb. 1, 2013, for PCT Application No. PCT/US2012/058751, filed on Oct. 4, 2012, 4 pages.
International Search Report mailed on Sep. 14, 2015, for PCT Application No. PCT/US2015/023720, filed on Mar. 31, 2015, 5 pages.
Jacob, J.S. (1985). "Corneal thickness changes following cataract surgery: effect of lens implantation and sodium hyaluronate," British Journal of Ophthalmology 69:567-571.
Johnson, D.H. et al. (2001). "How does nonpenetrating glaucoma surgery work? Aqueous outflow resistance and glaucoma surgery." J. Glaucoma 10:55-67.
Minckler, D. et al. (2006). "Aqueous shunts for glaucoma review," Cochrane Library, 47 total pages.
Myers, T.D. et al. (1999). "Comparison of the Effects of Viscoelastic Agents on Clinical Properties of the Unfolder Lens Injection System," Journal of Cataract and Refractive Surgery 25:953-958.
Nesterov, A.P. (1970). "Role of Blockage of Schlemm's Canal in Pathogenesis of Primary Open-Angle Glaucoma," Am. J. Ophthalmol. 70:691-696.
Non-Final Office Action mailed on May 17, 2010, for U.S. Appl. No. 11/475,523, filed Jun. 26, 2006, 10 pages.
Non-Final Office Action mailed on Jan. 26, 2012, for U.S. Appl. No. 12/695,053, filed Jan. 27, 2010, 10 pages.
Non-Final Office Action mailed on Mar. 15, 2012, for U.S. Appl. No. 13/245,811, filed Sep. 26, 2011, 4 pages.
Non-Final Office Action mailed on May 11, 2012, for U.S. Appl. No. 13/020,706, filed Feb. 3, 2011, 5 pages.
Non-Final Office Action mailed on Nov. 9, 2012, for U.S. Appl. No. 13/245,811, filed Sep. 26, 2011, 5 pages.
Non-Final Office Action mailed on Apr. 24, 2013, for U.S. Appl. No. 13/644,780, filed Oct. 4, 2012, 13 pages.
Non-Final Office Action mailed on Jun. 12, 2013, for U.S. Appl. No. 13/644,748, filed Oct. 4, 2012, 8 pages.
Non-Final Office Action mailed on Sep. 9, 2013, for U.S. Appl. No. 13/644,758, filed Oct. 4, 2012, 7 pages.
Non-Final Office Action mailed on Feb. 7, 2014, for U.S. Appl. No. 13/644,780, filed Oct. 4, 2012, 12 pages.
Non-Final Office Action mailed on Feb. 24, 2014, for U.S. Appl. No. 13/025,112, filed Feb. 10, 2011, 12 pages.
Non-Final Office Action mailed on May 15, 2014, for U.S. Appl. No. 13/644,758, filed Oct. 4, 2012, 7 pages.
Non-Final Office Action mailed on Nov. 28, 2014, for U.S. Appl. No. 13/644,748, filed Oct. 4, 2012, 7 pages.
Non-Final Office Action mailed on Jan. 14, 2015, for U.S. Appl. No. 13/644,758, filed Oct. 4, 2012, 10 pages.
Non-Final Office Action mailed on Feb. 4, 2015, for U.S. Appl. No. 13/445,816, filed Apr. 12, 2012, 6 pages.
Non-Final Office Action mailed on Feb. 23, 2015, for U.S. Appl. No. 13/025,112, filed Feb. 10, 2011, 17 pages.
Non-Final Office Action mailed on Jul. 10, 2015, for U.S. Appl. No. 13/025,112, filed Feb. 10, 2011, 16 pages.
Non-Final Office Action mailed on Oct. 7, 2015, for U.S. Appl. No. 14/527,292, filed Oct. 29, 2014, 5 pages.
Non-Final Office Action mailed on Nov. 3, 2015, for U.S. Appl. No. 14/539,648, filed Nov. 12, 2014, 7 pages.

(56) References Cited

OTHER PUBLICATIONS

Non-Final Office Action mailed on Dec. 14, 2015, for U.S. Appl. No. 13/445,816, filed Apr. 12, 2012, 7 pages.
Non-Final Office Action mailed on Jun. 7, 2016, for U.S. Appl. No. 14/527,292, filed Oct. 29, 2014, 5 pages.
Non-Final Office Action mailed on Feb. 25, 2016, for U.S. Appl. No. 13/644,769, filed Oct. 4, 2012, 19 pages.
Non-Final Office Action mailed on Jan. 18, 2017, for U.S. Appl. No. 14/539,648, filed Nov. 12, 2014, 13 pages.
Non-Final Office Action mailed on Mar. 22, 2017, for U.S. Appl. No. 13/644,769, filed Oct. 4, 2012, 31 pages.
Non-Final Office Action mailed on Aug. 28, 2017, for U.S. Appl. No. 14/973,620, filed Dec. 17, 2015, 6 pages.
Non-Final Office Action mailed on Nov. 7, 2017, for U.S. Appl. No. 14/816,822, filed Aug. 3, 2015, 14 pages.
Non-Final Office Action mailed on Dec. 15, 2017, for U.S. Appl. No. 15/343,147, filed Nov. 3, 2016, 12 pages.
Non-Final Office Action mailed on Apr. 4, 2018, for U.S. Appl. No. 14/675,580, filed Mar. 31, 2015, 10 pages.
Non-Final Office Action mailed on Aug. 9, 2018, for U.S. Appl. No. 15/182,165, filed Jun. 14, 2016, 9 pages.
Non-Final Office Action mailed on Aug. 29, 2018, for U.S. Appl. No. 14/973,620, filed Dec. 17, 2015, 11 pages.
Non-Final Office Action mailed on Sep. 20, 2018, for U.S. Appl. No. 15/340,911, filed Nov. 1, 2016, 7 pages.
Non-Final Office Action mailed on Oct. 7, 2019, for U.S. Appl. No. 15/854,126, filed Dec. 26, 2017, 13 pages.
Non-Final Office Action mailed on Nov. 25, 2019, for U.S. Appl. No. 16/189,882, filed Nov. 13, 2018, 12 pages.
Non-Final Office Action mailed on Aug. 10, 2020, for U.S. Appl. No. 14/973,620, filed Dec. 17, 2015, 8 pages.
Non-Final Office Action mailed on Oct. 1, 2020, for U.S. Appl. No. 16/397,733, filed Apr. 29, 2019, 7 pages.
Non-Final Office Action mailed on Jul. 15, 2021, for U.S. Appl. No. 17/239,263, filed Apr. 23, 2021, 9 pages.
Non-Final Office Action mailed on Aug. 26, 2021, for U.S. Appl. No. 17/239,270, filed Apr. 23, 2021, 21 pages.
Non-Final Office Action mailed on Mar. 4, 2022, for U.S. Appl. No. 17/553,671, filed Dec. 16, 2021, 9 pages.
Non-Final Office Action mailed on Mar. 10, 2022, for U.S. Appl. No. 17/553,408, filed Dec. 16, 2021, 18 pages.
Non-Final Office Action mailed on Apr. 26, 2022, for U.S. Appl. No. 16/413,466, filed May 15, 2019, 8 pages.
Non-Final Office Action mailed on Jul. 27, 2022, for U.S. Appl. No. 16/526,832, filed Jul. 30, 2019, 8 pages.
Non-Final Office Action mailed on Aug. 4, 2022, for U.S. Appl. No. 17/827,494, filed May 27, 2022, 20 pages.
Non-Final Office Action mailed on Aug. 24, 2022, for U.S. Appl. No. 17/827,485, filed May 27, 2022, 25 pages.
Non-Final Office Action mailed on Mar. 16, 2023, for U.S. Appl. No. 17/397,817, filed Aug. 9, 2021, 8 pages.
Notice of Allowance mailed on Feb. 2, 2011, for U.S. Appl. No. 11/475,523, filed Jun. 26, 2006, 6 pages.
Notice of Allowance mailed on Jun. 11, 2012, for U.S. Appl. No. 12/695,053, filed Jan. 27, 2010, 7 pages.
Notice of Allowance mailed on Apr. 2, 2013, for U.S. Appl. No. 13/245,811, filed Sep. 26, 2011, 6 pages.
Notice of Allowance mailed on May 10, 2013, for U.S. Appl. No. 13/020,706, filed Feb. 3, 2011, 8 pages.
Notice of Allowance mailed on Jul. 7, 2014, for U.S. Appl. No. 14/012,963, filed Aug. 28, 2013, 6 pages.
Notice of Allowance mailed on Jul. 23, 2014, for U.S. Appl. No. 13/644,780, filed Oct. 4, 2012, 8 pages.
Notice of Allowance mailed on Mar. 30, 2015, for U.S. Appl. No. 13/644,748, filed Oct. 4, 2012, 5 pages.
Notice of Allowance mailed on Aug. 10, 2015, for U.S. Appl. No. 13/644,758, filed Oct. 4, 2012, 7 pages.
Notice of Allowance mailed on Mar. 1, 2016, for U.S. Appl. No. 13/025,112, filed Feb. 10, 2011, 7 pages.

Corrected Notice of Allowability mailed on Apr. 25, 2016, U.S. Appl. No. 13/025,112, filed Feb. 10, 2011, 2 pages.
Notice of Allowance mailed on Jul. 13, 2016, for U.S. Appl. No. 13/445,816, filed Apr. 12, 2012, 7 pages.
Corrected Notice of Allowability mailed on Sep. 1, 2016, for U.S. Appl. No. 13/445,816, filed Apr. 12, 2012, 2 pages.
Notice of Allowance mailed on Oct. 25, 2017, for U.S. Appl. No. 13/644,769, filed Oct. 4, 2012, 8 pages.
Notice of Allowance mailed on Nov. 21, 2017, for U.S. Appl. No. 14/539,648, filed Nov. 12, 2014, 10 pages.
Notice of Allowance mailed on Aug. 31, 2018, for U.S. Appl. No. 14/816,822, filed Aug. 3, 2015, 7 pages.
Notice of Allowance mailed on Jan. 9, 2019, for U.S. Appl. No. 14/675,580, filed Mar. 31, 2015, 9 pages.
Notice of Allowance mailed on Feb. 6, 2019, for U.S. Appl. No. 15/182,165, filed Jun. 14, 2016, 8 pages.
Notice of Allowance mailed on Apr. 15, 2019, for U.S. Appl. No. 15/683,652, filed Aug. 22, 2017, 5 pages.
Notice of Allowance mailed on Apr. 23, 2019, for U.S. Appl. No. 15/340,911, filed Nov. 1, 2016, 5 pages.
Notice of Allowance mailed on Aug. 20, 2020, for U.S. Appl. No. 16/189,882, filed Nov. 13, 2018, 8 pages.
Notice of Allowance mailed on Sep. 16, 2020, for U.S. Appl. No. 15/854,126, filed Dec. 26, 2017, 9 pages.
Notice of Allowance mailed on Aug. 2, 2021, for U.S. Appl. No. 17/239,263, filed Apr. 23, 2021, 5 pages.
Notice of Allowance mailed on Sep. 17, 2021, for U.S. Appl. No. 16/532,260, filed Aug. 5, 2019, 9 pages.
Notice of Allowance mailed on Mar. 15, 2022, for U.S. Appl. No. 17/239,270, filed Apr. 23, 2021, 8 pages.
Notice of Allowance mailed on May 31, 2022, for U.S. Appl. No. 17/553,671, filed Dec. 16, 2021, 7 pages.
Notice of Allowance mailed on Jun. 8, 2022, for U.S. Appl. No. 16/413,466, filed May 15, 2019, 5 pages.
Notice of Allowance mailed on Jun. 28, 2022, for U.S. Appl. No. 17/553,408, filed Dec. 16, 2021, 9 pages.
Notice of Allowance mailed on Jul. 8, 2022, for U.S. Appl. No. 17/033,408, filed Sep. 25, 2020, 12 pages.
Notice of Allowance mailed on Nov. 23, 2022, for U.S. Appl. No. 17/827,494, filed May 27, 2022, 8 pages.
Notice of Allowance mailed on Nov. 29, 2022, for U.S. Appl. No. 16/526,832, filed Jul. 30, 2019, 5 pages.
Notice of Allowance mailed on Apr. 27, 2023, for U.S. Appl. No. 17/990,589, filed Nov. 18, 2022, 12 pages.
Notice of Allowance mailed on May 4, 2023, for U.S. Appl. No. 17/827,485, filed May 27, 2022, 12 pages.
Notice of Allowance mailed on May 11, 2023, for U.S. Appl. No. 16/526,832, filed Jul. 30, 2019, 5 pages.
Razeghinejad, M.R. et al. (2011). "A History of the Surgical Management of Glaucoma," Optom. Vis. Sci. 88:E39-E47.
Samuelson, T.W. (2011). "Randomized evaluation of the trabecular micro-bypass stent with phacoemulsification in patients with glaucoma and cataract," Ophthalmol. 118:459-467.
Schwartz, K.S. et al. (2006). "Glaucoma drainage implants: a critical comparison of types," Curr. Opin. Ophthalmol. 17:181-189.
Sidoti, P.A. et al. (1994). "Glaucoma drainage implants," Curr. Opin. Ophthalmol. 11:85-98.
Stefansson, J. (1925). "American journal of ophthalmology," vol. 8, pp. 681-693.
Stegmann, R. et al. (1999). "Viscocanalostomy for Open-Angle Glaucoma in Black African Patients," Journal of Cataract & Refractive Surgery 25:316-322.
Stegmann, R. (2002). Robert Stegmann, MD: taking on the challenges of ocular trauma and disease, Ocular Surgery News, located at https://www.healio.com/news/ophthalmology/20120331/robert-stegmann-md-taking-on-the-challenges-of-ocular-trauma-and-disease, 4 total pages.
Summary of Safety and Effectiveness Data, STAARVISCTM (sodium hyaluronate) Premarket Approval Application (PMA) No. P000046, Apr. 18, 2001, 11 total pages.
Wild, G.J. et al. (2001). "Dilation of Schlemm's Canal in Viscocanalostomy: Comparison of 2 Viscoelastic Substances," Journal of Cataract and Refractive Surgery 27:1294-1297.

(56) References Cited

OTHER PUBLICATIONS

Written Opinion mailed on Nov. 30, 2007, for PCT Application No. PCT/US2007/013038, filed on May 31, 2007, 6 pages.
Written Opinion mailed on Apr. 5, 2011, for PCT Application No. PCT/US2011/023643, filled on Feb. 3, 2011, 5 pages.
Written Opinion mailed on Feb. 1, 2013, for PCT Application No. PCT/US2012/058751, filed on Oct. 4, 2012, 6 pages.
Written Opinion mailed on Sep. 14, 2015, for PCT Application No. PCT/US15/23720, filed on Mar. 31, 2015, 8 pages.
Yablonski, M.E. (2005). "Trabeculectomy with internal tube shunt—a novel glaucoma surgery," J. Glaucoma 14:91-97.
Zhou, J. et al. (2006). "Trabecular bypass - Effect of Schlemm canal and collector channel dilation," J. Glaucoma 15:446-455.
Abu-Hassan, D.W. et al. (2014). "The trabecular meshwork: a basic review of form and function," J. Ocul. Biol. 2(1), 22 total pages.
Bonsignore, C. (2003). "A decade of evolution in stent design," SMST-2003, Proceedings of the International Conference on Shape and Memory and Superelastic Technologies, pp. 519-528, 13 total pages.
Brubaker, R.F. (2004). "Goldmann's equation and clinical measures of aqueous dynamics," Experimental Eye Research 78:633-637.
Brunette, D.M. et al. (2001). "Chapter 8: Mechanical, thermal, chemical and electrochemical surface treatment of titanium," in Titanium in Medicine: Material science, engineering, biological responses and medical applications, Springer, pp. 232-266.
Dietlein, T.S. et al. (2008). "Combined cataract-glaucoma surgery using the intracanalicular Eyepass glaucoma implant: first clinical results of a prospective pilot study," J. Cataract Refract Surg. 34:247-252.
Duerig, T. et al. (1999). "An overview of nitinol medical applications," Materials Science and Engineering A273-275:149-160.
Food and Drug Administration (Apr. 1, 2004). "Title 21—Food and Drugs Chapter I—Food and Drug Administration Department of Health and Human Services Subchapter H—Medical Devices," 2 total pages.
Glaukos Corporation iStent® Trabecular Micro-Bypass Stent (2021). Directions for Use/Package Insert, 23 total pages.
Healio (May 4, 2004). "EyePass glaucoma device shows promise," Ocular Surgery News, located at https://www.healio.com/news/ophthalmology/20120331/eyepass-glaucoma-device-shows-promise, 2 total pages.
Healio (Sep. 15, 2002). "Robert Stegmann, MD: taking on the challenges of ocular trauma and disease," Ocular Surgery News 20th Anniversary, 5 total pages.
Hill, R. (Nov./Dec. 2012). "Sidebar: Inventor's Perspective," located at https://glaucomatoday.com/articles/2012-nov-dec/sidebar-inventors-perspective, 3 total pages.
Hsu, S.W. et al. (May 2006). "In Vitro Studies of the Neuroform Microstent Using Transparent Human Intracranial Arteries," AJNR Am. J. Neuroradiol. 27:1135-1139.
Khng, C. et al. (2008). "Evaluation of the relationship between corneal diameter and lens diameter," J. Cataract Refract. Surg. 34:475-479.
Llobet, A. et al. (2003). "Understanding Trabecular Meshwork Physiology: a Key to the Control of Intraocular Pressure?" News Physiol. Sci. 18:205-209.
Mishra, P. et al. (Nov. 17, 2014). "Glaucoma drainage device: a review," Journal of Evolution and Medical and Dental Sciences, vol. 3, Issue 62, pp. 13744-13758.
Nitinol Product Information (2003). Memry Materials, 5 total pages.
Non-Final Office Action mailed on Jun. 23, 2023, for U.S. Appl. No. 18/130,353, filed Apr. 3, 2023, 15 pages.
Notice of Allowance mailed on Aug. 9, 2023, for U.S. Appl. No. 17/990,589, filed Nov. 18, 2022, 11 pages.
Pride, G.L. et al. (2004). "Stent-coil treatment of a distal internal carotid artery dissecting pseudoaneurysm on a redundant loop by use of a flexible, dedicated nitinol intracranial stent," AJNR Am. J. Neuroradiol. 25:333-337.
Prielipp, R.C. et al. (2007). "Stents, Stents, Everywhere—Now even in the BRAIN," apsf Newsletter, 8 total pages.
Schlemm's Canal Position Inside the Eye (IMAGE), EurekAlert! 2023, located at https://www.eurekalert.org/multimedia/757562, 2 total pages.
Sherwood, M. et al. (Mar. 1, 2006). "Rethinking glaucoma surgery: Aqueous within the eyewall," David E.I. Pyott Glaucoma Education Center, located at https://www.aao.org/education/current-insight/rethinking-glaucoma-surgery-aqueous-within-eyewall, 5 total pages.
Shrestha, S. et al. (2020). "Coronary artery stents: From the beginning to the present," Consultant 60:e1, 13 total pages.
Stoeckel, D. et al. (2002). "A survey of stent designs," Min. Invas. Ther. & Allied Technol. 11:137-147.
Usui, T. et al. (Aug. 2011). "Identification of Schlemm's canal and its surrounding tissues by anterior segment fourier domain optical coherence tomography," Invest. Ophthalmol. Vis. Sci. 52:6934-6939.
Weinreb, R.N. et al. (2004). "Primary open-angle glaucoma," Lancet 363:1711-1720.
Wittman, B. et al. (2017). "Eyepass Glaucoma Implant in Open-Angle Glaucoma After Failed Conventional Medical Therapy: Clinical Results of a 5-Year-Follow-up," J. Glaucoma 26:328-334.
Notice of Allowance mailed on Sep. 20, 2023, for U.S. Appl. No. 17/827,485, filed May 27, 2022, 10 pages.
Notice of Allowance mailed on Jan. 8, 2024, for U.S. Appl. No. 17/827,485, filed May 27, 2022, 10 pages.
Written Opinion of the International Searching Authority mailed on Feb. 7, 2024, for PCT Application No. PCT/US2023/072711, filed on Aug. 23, 2023, 12 pages.
Extended European Search Report mailed on Feb. 19, 2024, for EP Application No. 23 190 417.8, filed on Oct. 4, 2012, 7 pages.
Final Office Action mailed on Mar. 18, 2024, for U.S. Appl. No. 18/197,679, filed May 15, 2023, 26 pages.
Non-Final Office Action mailed on Mar. 20, 2024, for U.S. Appl. No. 17/498,626, filed Oct. 11, 2021, 7 pages.
Non-Final Office Action mailed on May 7, 2024, for U.S. Appl. No. 18/130,353, filed Apr. 3, 2023, 14 pages.
Non-Final Office Action mailed on May 10, 2024, for U.S. Appl. No. 16/943,644, filed Jul. 30, 2020, 10 pages.

* cited by examiner

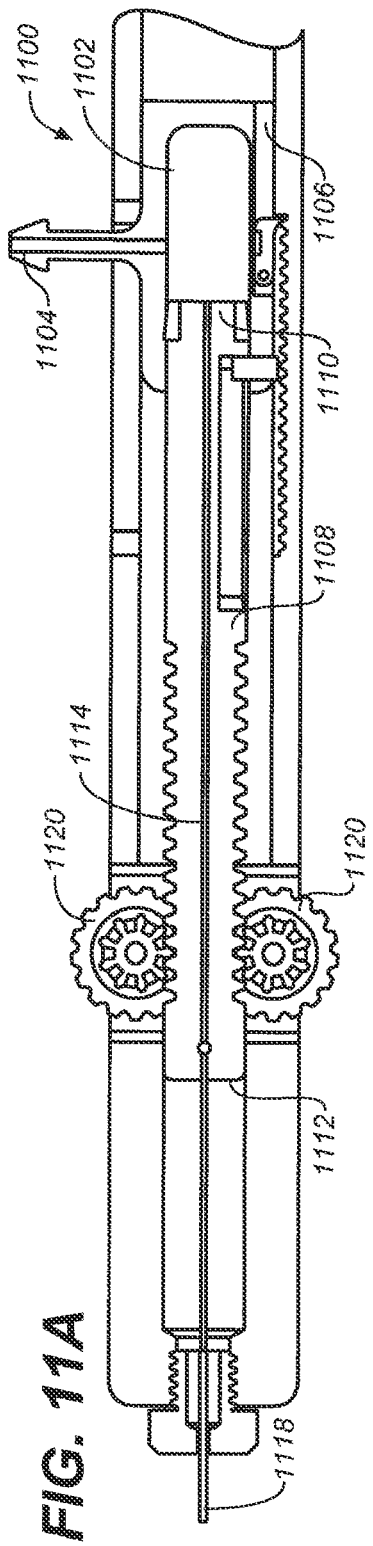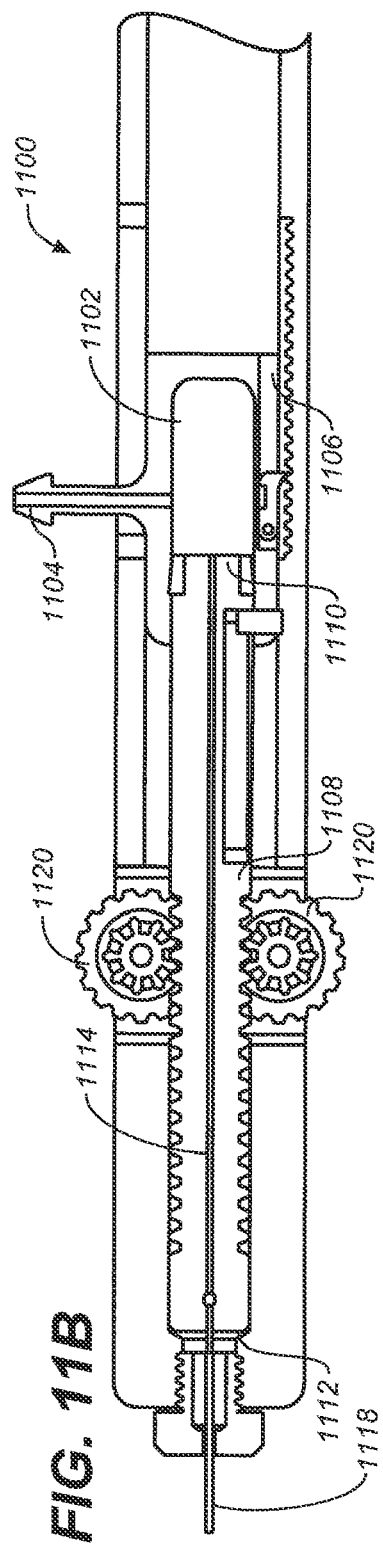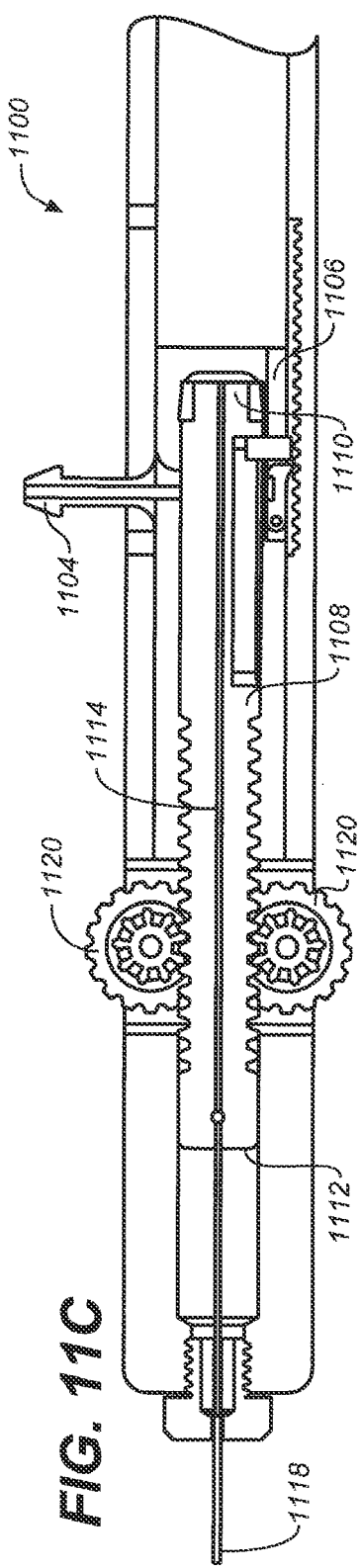

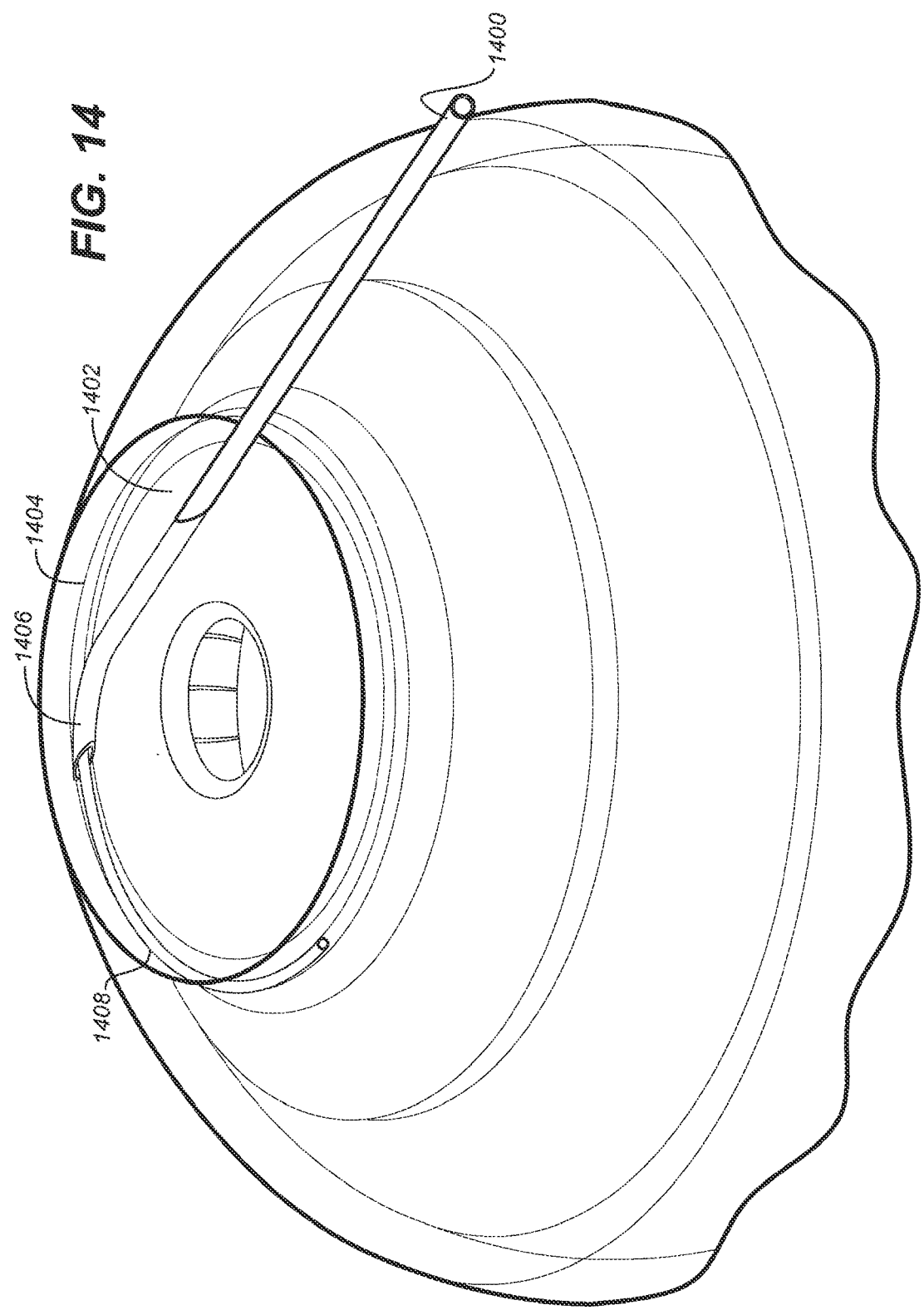

OCULAR DELIVERY SYSTEMS AND METHODS

CROSS-REFERENCE TO RELATED APPLICATIONS

This application is a continuation of U.S. application Ser. No. 17/827,494, filed on May 27, 2022, which is a continuation of U.S. application Ser. No. 17/553,671, filed on Dec. 16, 2021, which issued as U.S. Pat. No. 11,389,327 on Jul. 19, 2022, which is a continuation of U.S. application Ser. No. 17/472,147, filed on Sep. 10, 2021, which is a continuation of U.S. application Ser. No. 17/239,263, filed on Apr. 23, 2021, which issued as U.S. Pat. No. 11,116,660 on Sep. 14, 2021, which is a continuation of U.S. application Ser. No. 17/098,231, filed on Nov. 13, 2020, which is a continuation of U.S. application Ser. No. 16/189,882, filed on Nov. 13, 2018, which issued as U.S. Pat. No. 10,857,027 on Dec. 8, 2020, which is a continuation of U.S. application Ser. No. 14/816,822, filed Aug. 3, 2015, which issued as U.S. Pat. No. 10,179,066 on Jan. 15, 2019, which is a continuation of U.S. application Ser. No. 13/644,748, filed Oct. 4, 2012, which issued as U.S. Pat. No. 9,095,412 on Aug. 4, 2015, which claims priority to U.S. Provisional Application Ser. No. 61/613,274, filed on Mar. 20, 2012, each of which is hereby incorporated by reference in its entirety.

FIELD

Described here are systems and methods for accessing Schlemm's canal in an eye and for delivering an ocular device, tool or fluid composition therein. The ocular devices may maintain the patency of Schlemm's canal without substantially interfering with transmural, transluminal, circumferential, or longitudinal aqueous humor fluid flow across the canal. The fluid composition may be a viscoelastic fluid that is delivered into the canal to facilitate drainage of aqueous humor by dilating the canal, disrupting juxtacanalicular meshwork and the adjacent wall of Schlemm's canal, and increasing aqueous permeability through the trabeculo-canalicular, or transmural, outflow pathway. Minimally invasive methods for treating medical conditions associated with elevated intraocular pressure, including glaucoma, are also described.

BACKGROUND

Glaucoma is a potentially blinding disease that affects over 60 million people worldwide, or about 1-2% of the population. Typically, glaucoma is characterized by elevated intraocular pressure. Increased pressure in the eye can cause damage to the optic nerve which can lead to loss of vision and even blindness if left untreated. Consistent reduction of intraocular pressure can slow down or stop progressive loss of vision associated with glaucoma.

Increased intraocular pressure is generally caused by sub-optimal efflux or drainage of fluid (aqueous humor) from the eye. Aqueous humor or fluid is a clear, colorless fluid that is continuously replenished in the eye. Aqueous humor is produced by the ciliary body, and then ultimately exits the eye through the trabecular meshwork. The trabecular meshwork extends circumferentially around the eye at the anterior chamber angle, or drainage angle, which is formed at the intersection between the peripheral iris or iris root, the anterior sclera or scleral spur and the peripheral cornea. The trabecular meshwork feeds outwardly into Schlemm's canal, a narrow circumferential passageway generally surrounding the exterior border of the trabecular meshwork. Positioned around and radially extending from Schlemm's canal are aqueous veins or collector channels that receive drained fluid. The net drainage or efflux of aqueous humor can be reduced as a result of decreased facility of outflow, decreased outflow through the trabecular meshwork and canal of Schlemm drainage apparatus, increased episcleral venous pressure, or possibly, increased production of aqueous humor. Flow out of the eye can also be restricted by blockages or constriction in the trabecular meshwork and/or Schlemm's canal.

Glaucoma, pre-glaucoma, and ocular hypertension currently can be treated by reducing intraocular pressure using one or more modalities, including medication, incisional surgery, laser surgery, cryosurgery, and other forms of surgery. In general, medications or medical therapy are the first lines of therapy. If medical therapy is not sufficiently effective, more invasive surgical treatments may be used. For example, a standard incisional surgical procedure to reduce intraocular pressure is trabeculectomy, or filtration surgery. This procedure involves creating a new drainage site for aqueous humor. Instead of naturally draining through the trabecular meshwork, a new drainage pathway is created by removing a portion of sclera and trabecular meshwork at the drainage angle. This creates an opening or passage between the anterior chamber and the subconjunctival space that is drained by conjunctival blood vessels and lymphatics. The new opening may be covered with sclera and/or conjunctiva to create a new reservoir called a bleb into which aqueous humor can drain. However, trabeculectomy carries both short and long term risks. These risks include blockage of the surgically-created opening through scarring or other mechanisms, hypotony or abnormally low intraocular pressure, expulsive hemorrhage, hyphema, intraocular infection or endophthalmitis, shallow anterior chamber angle, macular hypotony, choroidal exudation, and others. Thus, alternatives to trabeculectomy are actively being sought.

One alternative is to implant a device in Schlemm's canal that maintains the patency of the canal or aids flow of aqueous humor from the anterior chamber into the canal. Various stents, shunts, catheters, and procedures have been devised for this purpose and employ an ab-externo (from the outside of the eye) approach to deliver the implant or catheter into Schlemm's canal. This method of placement is invasive and typically prolonged, requiring the creation of tissue flaps and deep dissections to access the canal. Additionally, it is very difficult for many surgeons to find and access Schlemm's canal from this incisional approach because Schlemm's canal has a small diameter, e.g., approximately 50 to 250 microns in cross-sectional diameter, and it may be even smaller when collapsed. One such procedure, ab-externo canaloplasty, involves making a deep scleral incision and flap, finding and unroofing Schlemm's canal, circumnavigating all 360 degrees of the canal with a catheter from the outside of the eye, and either employing viscoelastic, a circumferential tensioning suture, or both to help maintain patency of the canal. The procedure is quite challenging and can take anywhere from forty-five minutes to two hours. The long-term safety and efficacy of canaloplasty is very promising, but the procedure remains surgically challenging and invasive.

Another alternative to trabeculectomy is viscocanalostomy, which involves the injection of a viscoelastic solution into Schlemm's canal to dilate the canal and associated collector channels. Dilation of the canal and collector channels in this manner generally facilitates drainage of aqueous humor from the anterior chamber through the trabecular meshwork and Schlemm's canal, and out through the natural trabeculocanalicular outflow pathway. Viscocanalostomy is similar to canaloplasty (both are invasive and ab-externo), except that viscocanalostomy does not involve a suture and does not restore all 360 degrees of outflow facility. Some advantages of viscocanalostomy are that sudden drops in intraocular pressure, hyphema, hypotony, and flat anterior chambers may be avoided. The risk of cataract formation and infection may also be minimized because of the absence of full eye wall penetration, anterior chamber opening, and iridectomy. A further advantage of viscocanalostomy is that the procedure restores the physiologic outflow pathway, thus avoiding the need for external filtration in the majority of eyes. This makes the success of the procedure partly independent of conjunctival or episcleral scarring, which is a leading cause of failure in trabeculectomy. Moreover, the absence of an elevated filtering bleb avoids related ocular discomfort and potentially devastating ocular infections, and the procedure can be carried out in any quadrant of the outflow pathway. Finally, because the entire physiology and purpose of the trabecular meshwork is unknown, retaining it may have benefits that will be realized in the future.

However, despite the advantages of viscocanalostomy and canaloplasty over trabeculectomy, current viscocanalostomy and canaloplasty techniques are still very invasive because access to Schlemm's canal must be created by making a deep incision into the sclera and creating a scleral flap and un-roofing Schlemm's canal. In their current forms, these procedures are both "ab-externo" procedures. "Ab-externo" generally means "from the outside" and therefore inherently implies invasiveness. On the other hand, "ab-interno" means "from the inside" and inherently implies a less invasive or minimally invasive approach. The ab-externo viscocanalostomy and canaloplasty procedures also remain challenging to surgeons, because as previously stated, it is difficult to find and access Schlemm's canal from the outside using a deep incisional approach due to the small diameter of Schlemm's canal. A further drawback still is that at most, viscocanalostomy can only dilate 60 degrees of Schlemm's canal, which is a 360 degree ring-shaped outflow vessel-like structure. The more of the canal that can be dilated, the more total aqueous outflow can be restored.

Accordingly, it would be beneficial to have systems that easily and atraumatically provide access to Schlemm's canal using an ab-interno approach for the delivery of ocular devices and compositions. It would also be useful to have systems that deliver devices and compositions into Schlemm's canal expeditiously to decrease procedure time and the risk of infection without compromising safety and precision of the delivery procedure. It would also be useful to have systems that deliver devices and fluid compositions into Schlemm's canal using an ab-interno approach so that cataract surgery and glaucoma surgery can both be accomplished during the same surgical sitting using the very same corneal or scleral incision. Such incisions are smaller and allow for less invasive surgery. This approach allows for accessing Schlemm's canal through the trabecular meshwork from the inside of the eye, and thus it is called "ab-interno". Methods of delivering ocular devices and compositions that effectively disrupt the juxtacanalicular meshwork and adjacent wall of Schlemm's canal, also known as the inner wall of Schlemm's canal, maintain the patency of Schlemm's canal, increase outflow, decrease resistance to outflow, or effectively dilate the canal using the systems in a minimally invasive, ab-interno manner would also be desirable.

SUMMARY

Described here are systems and methods for easily accessing Schlemm's canal with minimal trauma and for delivering an ocular device (e.g., an implant) therein. Other systems and methods may be implant-free, and/or rely on the delivery and removal of a therapeutic (disruptive) tool and/or the delivery of a fluid composition into Schlemm's canal to improve flow through the trabeculocanalicular outflow system, which consists of the trabecular meshwork, juxtacanalicular tissue, Schlemm's canal, and collector channels. Once implanted within the canal, the ocular device may maintain the patency of Schlemm's canal without substantially interfering with transmural fluid flow across the canal. Transmural flow, or transmural aqueous humor flow, is defined as flow of aqueous humor from the anterior chamber across the trabecular meshwork into the lumen of Schlemm's canal, across and along the lumen of Schlemm's canal, and ultimately into aqueous collector channels originating in the outer wall of Schlemm's canal. The fluid composition, e.g., a viscoelastic fluid, delivered into the canal may facilitate drainage of aqueous humor by dilating the canal, rendering the trabecular meshwork and inner wall of Schlemm's canal more permeable to aqueous humor, and also dilating aqueous collector channels. The therapeutic tool may also facilitate drainage of aqueous humor by dilating the canal, dilating the collector channels, disrupting or stretching the trabecular meshwork, disrupting or stretching the juxtacanalicular tissue, tearing the trabecular meshwork or juxtacanalicular tissue, or completely removing the trabecular meshwork or juxtacanalicular tissue. Any or all of these actions may reduce resistance to outflow, increase aqueous outflow and drainage, and reduce intraocular pressure. One of the beneficial features of the system may be a cannula configured with a distal curved portion that defines a radius of curvature, where the radius of curvature directly engages the bevel at the distal tip of the cannula. The specific configuration of the handle of the system may also be useful. The handle may be sized and shaped so that it is easily manipulated with one hand. Furthermore, the handle may be designed for universal manipulation. By "universal" it is meant that the handle is ergonomically configured for both right-handed and left-handed use, for use to access any quadrant of the eye, and for use in advancing a cannula or conduit into Schlemm's canal in a clockwise or counterclockwise fashion. Such an ergonomic configuration may include a drive assembly that can be actuated by fingers of one hand (e.g., the right hand) when in a first orientation, and when turned over to a second, flipped orientation, can be actuated by the fingers of the other hand (e.g., the left hand). Alternatively, the cannula itself can be rotated to the extent needed (e.g., 180 degrees) to provide ambidextrous ease of use in a clockwise or counterclockwise advancement direction. Additionally, such a configuration may include a drive assembly that can be actuated by fingers of one hand (e.g., the right hand) to deliver an implant or fluid in a clockwise fashion when in a first orientation, and when turned over to a second, flipped orientation, can be actuated by the fingers of the same hand (e.g., the right hand) to deliver fluid or an implant in a counterclockwise fashion.

The ocular delivery systems described herein generally include a universal handle having a grip portion and a housing that has an interior and a distal end. A cannula is typically coupled to and extends from the housing distal end. The cannula may include a proximal end and a distal curved portion, where the distal curved portion has a proximal end and a distal end, and a radius of curvature defined between the ends. The cannula may also be configured to include a body; a distal tip having a bevel; and a lumen extending from the proximal end through the distal tip. The bevel may directly engage the distal end of the curved portion of the cannula (i.e., the bevel may directly engage the radius of curvature). The systems may also generally include a drive assembly substantially contained within the housing comprising gears that translate rotational movement to linear movement.

When an ocular device is to be implanted into Schlemm's canal, the system may further include a slidable positioning element having a proximal end and a distal end that is coaxially disposed within the cannula lumen. The distal end of the slidable positioning element may comprise an engagement mechanism for positioning (including manipulating) the ocular device within the canal. Exemplary engagement mechanisms that may be employed comprise hooks, jaws, clasps, or complimentary mating elements for releasable attachment of the ocular devices.

The system may be configured to include a fluid assembly in the handle and a slidable conduit coaxially disposed within the cannula lumen when a fluid composition is to be delivered into Schlemm's canal. The fluid composition may be delivered through the distal end of the conduit or through openings spaced along the axial length of the conduit. Additionally, the fluid assembly may be coupled to a loading component configured to transfer fluid compositions into a reservoir at least partially defined by the assembly. Some variations of the system may have the fluid composition preloaded in the reservoir. Exemplary fluid compositions include without limitation, saline, pharmaceutical compounds, and viscoelastic fluids. The viscoelastic fluids may comprise hyaluronic acid, chondroitin sulfate, cellulose, or salts, derivatives, or mixtures thereof. Use of sodium hyaluronate as the viscoelastic fluid may be beneficial. Additionally, commercially available syringes of viscoelastic may be loaded into the handle to function as a reservoir where the plunger of the syringe is gradually compressed to deliver viscoelastic. When a therapeutic (disruptive) tool is used (without the delivery of an implant or fluid), the handle may or may not include a fluid reservoir.

Methods for implanting an ocular device within Schlemm's canal are also described. Using the ocular delivery systems disclosed herein, the method generally includes the steps of creating an incision in the ocular wall that provides access to the anterior chamber of the eye; advancing a cannula of the system through the incision, across a portion of the anterior chamber, to the trabecular meshwork, and piercing the trabecular meshwork; accessing Schlemm's canal with the cannula; and implanting the device within the canal. The cannula will typically comprise a proximal end and a distal curved portion, the distal curved portion having a proximal end and a distal end and a radius of curvature defined between the ends; a body; a distal tip having a bevel, the bevel directly engaging the distal end of the curved portion of the cannula; and a lumen extending from the proximal end through the distal tip. A positioning element slidable within the cannula lumen may be employed during the step of implanting the device within the canal. The device may be implanted to reduce intraocular pressure or to treat a medical condition such as glaucoma, pre-glaucoma, or ocular hypertension.

Methods for delivering a fluid composition into Schlemm's canal are further described. Using the ocular delivery systems disclosed herein, the method generally includes the steps of creating an incision in the ocular wall that provides access to the anterior chamber of the eye; advancing a cannula of the system through the incision to the trabecular meshwork; accessing Schlemm's canal with the cannula; and delivering the fluid composition into Schlemm's canal using a conduit slidable within the cannula lumen. The cannula will typically comprise a proximal end and a distal curved portion, the distal curved portion having a proximal end and a distal end and a radius of curvature defined between the ends; a body; a distal tip having a bevel, the bevel directly engaging the distal end of the curved portion of the cannula; and a lumen extending from the proximal end through the distal tip. The fluid composition may be delivered into Schlemm's canal through the distal end of the conduit or through openings spaced along the axial length of the conduit. Fluids such as saline and viscoelastic solutions may be delivered into the canal to dilate the canal and collector channels and/or to disrupt the juxtacanalicular meshwork or inner wall of Schlemm's canal to enhance permeability to aqueous humor, reduce resistance to aqueous outflow, or increase aqueous outflow. Examples of viscoelastic solutions are those that include hyaluronic acid, chondroitin sulfate, cellulose, and derivatives and mixtures thereof. As previously stated, the use of sodium hyaluronate as the viscoelastic solution may be beneficial. Drugs for treating glaucoma may also be combined with the viscoelastic solutions. The drugs may also be delivered alone without viscoelastic if desired.

When the fluid composition is delivered, the delivery step may include actuation of the drive assembly so that retraction of at least a portion of the gears (or reversal of gear movement) pressurizes the reservoir in an amount sufficient to force the fluid composition through the conduit lumen. The fluid composition may be delivered to dilate Schlemm's canal. The fluid composition may also be delivered to reduce intraocular pressure or to treat a medical condition such as glaucoma.

The systems, devices, and methods described herein may also employ varying degrees of force to disrupt trabeculo-canalicular tissues, e.g., the trabecular meshwork, juxta-canalicular tissue, Schlemm's canal, walls of Schlemm's canal, septae inside Schlemm's canal, and collector channels, to improve drainage of aqueous humor and in turn, reduce intraocular pressure and treat conditions of the eye. The disruptive force may be generated by implant-free methods, e.g., by delivering a disruptive volume of viscoelastic fluid, advancing disruptive tools, e.g., cannulas, conduits, catheters, etc., including one or more disruptive components on their distal portions, or both. Depending on factors such as the type or severity of the condition being treated, the disruptive force may be generated to partially cut, tear, stretch, dilate, destroy, or completely destroy and/or remove, the trabecular meshwork and/or juxtacanalicular tissue, and may be adjusted by varying the volume of viscoelastic fluid delivered, or by varying the tool configuration, as further discussed below.

The viscoelastic fluid may be delivered using a unitary and single-handed, single-operator controlled device. Advancement of the disruptive tools may also be provided by a unitary and single-handed, single-operator controlled device. By "unitary" it is meant that one device is employed to advance a conduit through at least a portion of Schlemm's canal and deliver a viscoelastic fluid, disruptive tool, or implant into Schlemm's canal. By "single-operator controlled" it is meant that all features of the device, e.g., cannula, conduit, and tool advancement and retraction, ocular device delivery, fluid delivery, etc., can be performed by one user. This is in contrast to other systems that use forceps to advance a delivery catheter into Schlemm's canal and/or devices containing viscoelastic fluid that are separate or independent from a delivery catheter, and which require connection to the delivery catheter during a procedure by an assistant or assistants while the delivery catheter is held by the surgeon. Following delivery of a disruptive volume of fluid or a disruptive tool, an implant, e.g., a helical support, may be advanced into Schlemm's canal to maintain its patency, or energy delivered to modify the structure of Schlemm's canal and/or the surrounding trabeculocanalicular tissues.

The single-handed, single-operator controlled device for delivering fluids may include a cannula; a conduit slidably disposed within, and advanceable distally from, the cannula; and a handle coupled to the cannula, where a portion of the handle defines a fluid reservoir, and where the handle is capable of being operated with a single-hand to deliver the fluid from the reservoir through the conduit.

Alternatively, a device for delivering viscoelastic fluids may include a cannula; a conduit slidably disposed within, and advanceable distally from, the cannula; a handle coupled to the cannula, where a portion of the handle defines a fluid reservoir; and a linear gear moveable to advance a fluid from the fluid reservoir through the conduit.

The device for delivering viscoelastic fluids may also be configured to include a universal handle having a proximal end and a distal end; a cannula extending from the distal end and having a proximal portion and a distal portion; a slidable conduit disposed within the cannula; a housing having an interior and upper and lower surfaces; and a wheeled drive assembly; where the wheeled drive assembly extends past the upper and lower surfaces of the housing. Such a device having a universal handle may further include a rotating cannula that can be rotated, e.g., from a left to right position, and a wheeled drive assembly that comprises a single wheel (rotatable component) configured to slide the conduit. Instead of a wheel, a button or slide could also be configured to slide the conduit.

In all variations of the viscoelastic fluid delivery devices, the conduit may have an outer diameter ranging from about 25 microns to about 500 microns, from about 50 microns to about 500 microns, from about 150 microns to about 500 microns, from about 200 microns to about 500 microns, from about 300 microns to about 500 microns, from about 200 microns to about 250 microns, or from about 180 microns to about 300 microns. In some instances it may be beneficial for the conduit to have an outer diameter of about 240 microns. The conduit may also comprise a plurality of openings spaced along at least a portion of its axial length or have a distal end with a cut out configured as a half tube.

In addition to disrupting Schlemm's canal and the surrounding trabeculocanalicular tissues using a disruptive volume of viscoelastic fluid, the outer diameter of the conduit may be sized to disrupt those tissues. For example, a conduit having an outer diameter ranging from about 200 microns to about 500 microns may be beneficial for disrupting tissues. Furthermore, a distal portion of the conduit may include a disruptive component, e.g., a notch, hook, barb, or combinations thereof, that disrupts tissues. However, the devices may not need to include both features, i.e., deliver a disruptive volume of viscoelastic fluid and also have a conduit sized for disruption. A conduit sized or configured for disruption of Schlemm's canal and surrounding tissues may be used alone to reduce intraocular pressure, without the delivery of fluids. Such a conduit may or may not have a lumen. Conduits may also be configured to be inflatable or expandable to a size that disrupts tissues as it is advanced.

The handle of the viscoelastic fluid delivery devices described herein may include a drive assembly capable of pressurizing the fluid to deliver the fluid from the reservoir through the conduit. The drive assembly may be a wheeled drive assembly that includes one rotatable component or a plurality of rotatable components. The reservoir may be preloaded with the viscoelastic fluid. Exemplary viscoelastic fluids may comprise hyaluronic acid, chondroitin sulfate, cellulose, or salts, derivatives, or mixtures thereof. It may be beneficial to use sodium hyaluronate as the viscoelastic fluid.

The implant-free methods for treating conditions of the eye may include advancing a conduit into Schlemm's canal, where the conduit has been loaded with a volume of viscoelastic fluid, and delivering the viscoelastic fluid into Schlemm's canal at a volume sufficient to disrupt the trabeculocanalicular tissues to reduce intraocular pressure. However, the implant-free methods for treating conditions of the eye may not necessarily include delivery of viscoelastic fluids. In these instances, the method may comprise advancing a device into Schlemm's canal, where the device has a diameter between about 200 and about 500 microns, and where advancement of the device into Schlemm's canal disrupts the trabeculocanalicular tissues sufficient to reduce intraocular pressure.

Other methods for treating conditions of the eye may be single-handed, single-operator methods for introducing viscoelastic fluid into Schlemm's canal that include advancing a conduit into Schlemm's canal, where the conduit has been loaded with a volume of viscoelastic fluid, and delivering the viscoelastic fluid into Schlemm's canal, where delivering the volume of viscoelastic fluid is accomplished by a single-handed device used by a single operator.

When viscoelastic fluids are delivered in the methods disclosed herein, the disruptive volume may be between about 2 µl (microliters) to about 16 µl (microliters), or between about 2 µl to about 8 µl. In some variations of the method, the volume of fluid capable of disrupting trabeculocanalicular tissues is about 2 µl, about 3 µl, about 4 µl, about 5 µl, about 6 µl, about 7 about 8 µl, about 9 µl, about 10 µl, about 11 µl, about 12 µl, 13 µl, about 14 µl, about 15 µl, or about 16 µl. It may be beneficial to deliver a volume of about 4 µl of viscoelastic fluid in certain instances. In yet further variations, the volume of fluid delivered ranges from about 1 µl per 360 degrees of the canal to about 50 µl per 360 degrees of the canal. The viscoelastic fluid may be delivered while advancing the conduit of a single-handed, single-operator controlled device from Schlemm's canal in the clockwise direction, counterclockwise direction, or both, and/or during withdrawal of the conduit from Schlemm's canal. As previously stated, the viscoelastic fluid may be delivered to disrupt Schlemm's canal and surrounding trabeculocanalicular tissues. For example, the delivered viscoelastic fluid may cause disruption by dilating Schlemm's canal, increasing the porosity of the trabecular meshwork, stretching the trabecular meshwork, forming microtears in juxtacanalicular tissue, removing septae from Schlemm's canal, dilating collector channels, or a combination thereof. The conduit may be loaded with the viscoelastic fluid at the start of an ocular procedure so that a single-operator can use a single hand to manipulate the device (e.g., advance and retract the conduit or any associated tool) and deliver the fluid into the trabeculocanalicular tissues.

The methods disclosed herein may also include advancement of the conduit about a 360 degree arc of Schlemm's canal, a 180 degree arc of Schlemm's canal, or a 90 degree arc of Schlemm's canal. Advancement may occur from a single access point in Schlemm's canal or from multiple access points in the canal. The disclosed methods may also be used to treat a variety of eye conditions, including, but not limited to, glaucoma, pre-glaucoma, and ocular hypertension.

Methods for ab-interno trabeculotomy and goniotomy are also disclosed using the devices and steps disclosed herein, including advancing a cannula at least partially through the anterior chamber of the eye, entering Schlemm's canal at a single access point using the cannula, and delivering a volume of a viscoelastic fluid through a conduit slidable within, and extendable from, the cannula, sufficient to disrupt the structure of Schlemm's canal and surrounding trabeculocanalicular tissues to reduce intraocular pressure. Another method that may be useful in treating conditions of the eye includes entering Schlemm's canal using a conduit extendable from a single-operator controlled handle, the handle comprising a fluid reservoir, and delivering a volume of a viscoelastic fluid from the fluid reservoir through the conduit by increasing pressure within the fluid reservoir, where the volume of delivered viscoelastic fluid is sufficient to disrupt the structure of Schlemm's canal and surrounding tissues to reduce intraocular pressure. Other methods for ab-interno trabeculotomy and goniotomy may include cutting, tearing, and/or removing trabecular meshwork without the delivery of a viscoelastic fluid. In such methods, a conduit configured to mechanically tear and remove trabecular meshwork may be employed. Here the conduit may comprise a larger diameter, cutting features, and/or tool along or at the distal portion or the conduit. For example, if the trabecular meshwork were being both cut and removed, the conduit might pull excised tissue back into the cannula during retraction.

BRIEF DESCRIPTION OF THE DRAWINGS

FIG. 4A shows the drive assembly in the handle of the system in a first orientation for use with one hand and FIG. 4B shows the handle in a second, flipped orientation that can be used with the other hand.

FIG. 10A is a perspective view of the system. FIG. 10B is a partial cross-sectional view of the system.

FIGS. 11A-11C illustrate an exemplary method of delivering a fluid composition out of the delivery system.

FIG. 14 is a stylized depiction of an ab-interno method for accessing Schlemm's canal with the cannula of an exemplary delivery system.

DETAILED DESCRIPTION

Described here are systems and methods for accessing Schlemm's canal and for delivering an ocular device and/or fluid composition therein to reduce intraocular pressure and thereby treat conditions of the eye. The fluids and certain components of the system, e.g., the slidable conduit, may be used to provide a force for disrupting trabeculocanalicular tissues, which include the trabecular meshwork, juxtacanalicular tissue, Schlemm's canal, and the collector channels. As used herein, the term "disrupting" refers to the delivery of a volume of fluid or a system component that alters the tissue in a manner that improves flow through the trabeculocanalicular outflow pathway. Examples of tissue disruption include, but are not limited to, dilation of Schlemm's canal, dilation of collector channels, increasing the porosity of the trabecular meshwork, stretching the trabecular meshwork, forming microtears in juxtacanalicular tissue, removing septae from Schlemm's canal, cutting or removal of trabeculocanalicular tissues, or a combination thereof.

Figure 1:
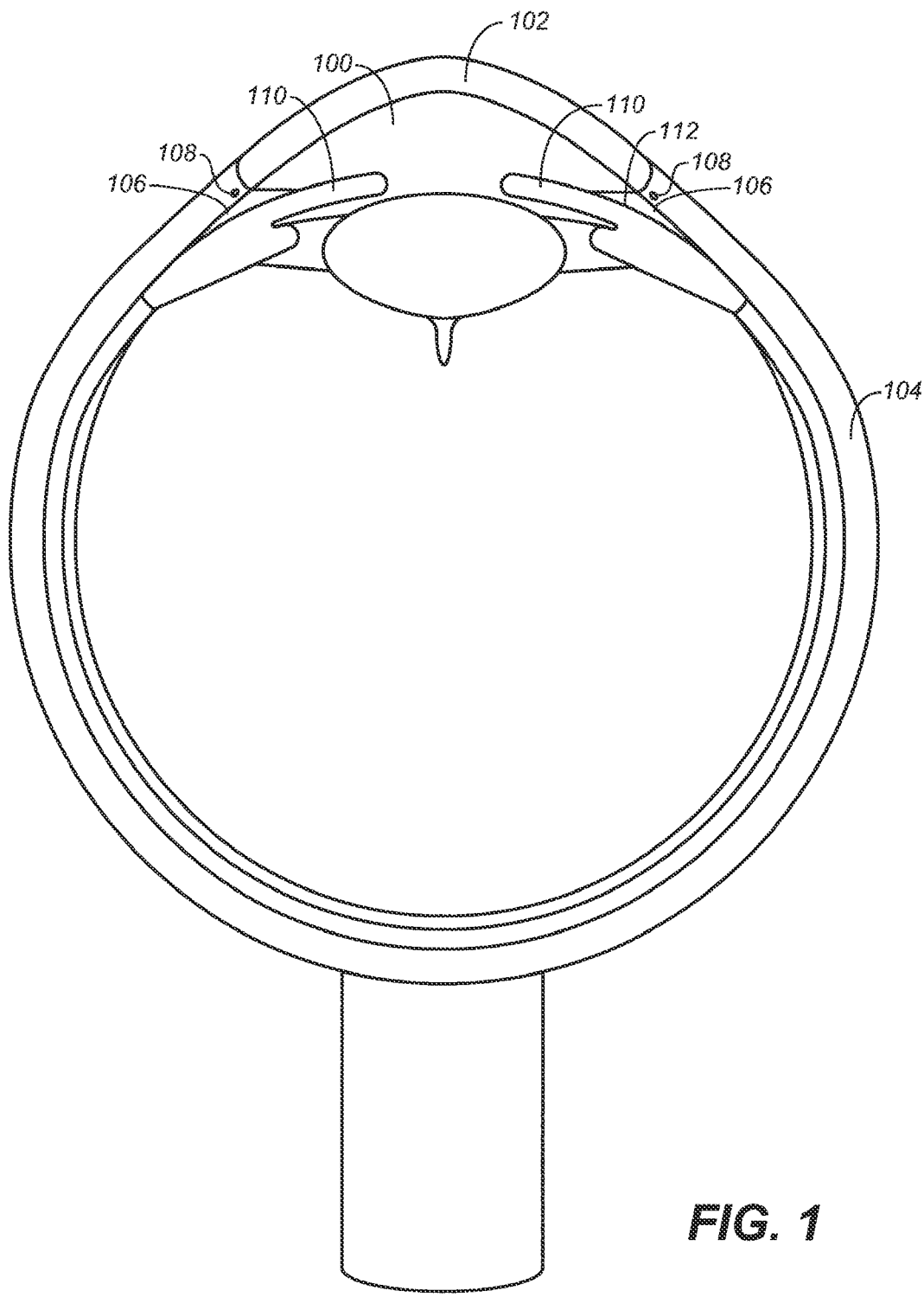
FIG. 1 shows a stylized, cross-sectional view of the eye and some of the structures involved in the flow of aqueous humor out of the eye.

To better understand the systems and methods described here, it may be useful to explain some of the basic eye anatomy. FIG. 1 is a stylized depiction of a normal human eye. The anterior chamber (100) is shown as bounded on its anterior surface by the cornea (102). The cornea (102) is connected on its periphery to the sclera (104), which is a tough fibrous tissue forming the white shell of the eye. Trabecular meshwork (106) is located on the outer periphery of the anterior chamber (100). The trabecular meshwork (106) extends 360 degrees circumferentially around the anterior chamber (100). Located on the outer peripheral surface of the trabecular meshwork (106) is Schlemm's canal (108). Schlemm's canal (108) extends 360 degrees circumferentially around the meshwork (106). At the apex formed between the iris (110), meshwork (106), and sclera (104), is angle (112).

The systems are generally configured for single-handed manipulation and for control by a single operator, and include one or more features useful for easily accessing Schlemm's canal with minimal trauma. Once access to the canal has been obtained, the system may deliver an ocular device, a fluid composition, or both. In some variations, the system advances a tool that disrupts Schlemm's canal and surrounding tissues without delivery of an ocular device or a fluid composition. For example, the tool may be a conduit, slidable within, and extendable from, the cannula used to access the canal, having an outer diameter sized to disrupt the canal and surrounding tissues. The distal end of the conduit may also be provided with a disruptive component to aid in the disruption of trabeculocanalicular tissues.

The device that is implanted into the canal will generally be configured to maintain the patency of Schlemm's canal without substantially interfering with transmural fluid flow across the canal. Ocular implants such as those disclosed in U.S. Pat. No. 7,909,789 may be delivered. In some variations, the implants in U.S. Pat. No. 7,909,789 include a support having a least one fenestration that completely traverses a central core of Schlemm's canal without substantially interfering with transmural fluid flow or longitudinal fluid flow across or along the canal. The ocular device may also disrupt the juxtacanalicular trabecular meshwork or adjacent inner wall of Schlemm's canal. The ocular devices may also be coated with a drug useful for treating ocular hypertension, glaucoma, or pre-glaucoma, infection, or scarring or inflammation postoperatively. The ocular device may also be formed to be solid, semi-solid, or bioabsorbable.

The systems may also be used to deliver a fluid composition, e.g., saline or a viscoelastic fluid. The saline may be used for irrigation. The viscoelastic fluid may be employed in ab-interno versions of viscocanalostomy or canaloplasty procedures to disrupt the canal and surrounding tissues.

I. Systems/Devices

The systems described herein may be single-handed, single-operator controlled devices that generally include a universal handle having a grip portion and a housing that has an interior and a distal end. A cannula is typically coupled to and extends from the housing distal end. The cannula may include a proximal end and a distal curved portion, where the distal curved portion has a proximal end and a distal end, and a radius of curvature defined between the ends. The cannula may also be configured to include a body; a distal tip having a bevel; and a lumen extending from the proximal end through the distal tip. The bevel may directly engage the distal end of the curved portion of the cannula (i.e., the bevel may directly engage the radius of curvature). The systems may also generally include a drive assembly partially contained within the housing comprising gears that translate rotational movement to linear movement. When an ocular device is to be implanted into Schlemm's canal, the systems may further include a slidable positioning element having a proximal end and a distal end that is coaxially disposed within the cannula lumen. The system may also be configured to include a fluid assembly in the handle and a slidable conduit coaxially disposed within the cannula lumen when a fluid composition is to be delivered into Schlemm's canal. Fluid compositions such as saline, viscoelastic fluids, including viscoelastic solutions, air, and gas may be delivered using the system. Suitable markings, colorings, or indicators may be included on any portion of the system to help identify the location or position of the distal end of the cannula, the positioning element, the engagement mechanism, the ocular device, or the slidable conduit.

Universal Handle

The ocular delivery systems described herein may include a universal handle capable of single-handed use. For example, the handle may be configured to be capable for use with the right hand in one orientation, and then with a simple flip of the handle (or by rotating the cannula itself 180 degrees) to a second orientation, use with the left hand. The handle generally includes a grip portion and a housing. The grip portion may be raised, depressed, or grooved in certain areas, or textured to improve hold of the handle by the user or to improve comfort of the user. The housing may include an interior portion and a distal end. The interior portion of the housing may contain a drive assembly and a positioning element (both further described below). In some variations, the distal end of the housing includes a fluid port that can provide fluids for irrigation of the operative field or to purge air from the system.

The universal handle may be made from any suitable material, including without limitation, fluoropolymers; thermoplastics such as polyetheretherketone, polyethylene, polyethylene terephthalate, polyurethane, nylon, and the like; and silicone. In some variations, the housing or portions thereof may be made from transparent materials. Materials with suitable transparency are typically polymers such as acrylic copolymers, acrylonitrile butadiene styrene (ABS), polycarbonate, polystyrene, polyvinyl chloride (PVC), polyethylene terephthalate glycol (PETG), and styrene acrylonitrile (SAN). Acrylic copolymers that may be particular useful include, but are not limited to, polymethyl methacrylate (PMMA) copolymer and styrene methyl methacrylate (SMMA) copolymer (e.g., Zylar 631® acrylic copolymer).

The length of the universal handle may generally be between about 4 inches (10.2 cm) and 10 inches (25.4 cm). In some variations, the length of the universal handle is about 7 inches (17.8 cm).

Cannula

The cannula of the ocular delivery system is typically coupled to and extends from the housing distal end, and is generally configured to provide easy and minimally traumatic access to Schlemm's canal using a minimally invasive ab-interno approach. Some variations of the cannula may include a proximal end and a distal curved portion, where the distal curved portion has a proximal end and a distal end, and a radius of curvature defined between the ends. The cannula may also be configured to include a body; a distal tip having a bevel; and a lumen extending from the proximal end through the distal tip. The bevel may directly engage the distal end of the curved portion of the cannula (i.e., the bevel may directly engage the radius of curvature).

The cannula may be made from any suitable material with sufficient stiffness to allow it to be advanced through the eye wall and anterior chamber. For example, the cannula may be formed of a metal such as stainless steel, nickel, titanium, aluminum, or alloys thereof (e.g., Nitinol® metal alloy) or a polymer. Exemplary polymers include without limitation, polycarbonate, polyetheretherketone (PEEK), polyethylene, polypropylene, polyimide, polyamide, polysulfone, polyether block amide (PEBAX), and fluoropolymers. In some instances, it may be advantageous to coat the cannula with a lubricious polymer to reduce friction between the ocular tissue and the cannula during the procedure. Lubricious polymers are well known in the art, and include, without limitation, polyvinyl alcohol, polyethylene glycol, polyvinyl pyrrolidone, fluorinated polymers (including polytetralluomethylene (PTFE or Teflon®)), and polyethylene oxide.

The cannula generally has an outer diameter sized to gain access to the lumen of Schlemm's canal while minimally obstructing the surgeon's view. Accordingly, the outer diameter may range from about 150 microns to about 800 microns. The cannula also has an inner diameter, which may range from about 50 microns to about 400 microns. The cannula may also be formed to have any suitable cross-sectional profile, e.g., circular, elliptical, triangular, square, rectangular, etc.

The cannula may be configured to include multiple portions or parts. A cannula having a body, a distal curved portion having a proximal end and a distal end, a radius of curvature defined between the ends, and a bevel at the distal tip of the cannula that directly engages the distal end of the curved portion of the cannula may be particularly useful for accessing the lumen of Schlemm's canal. Here the body (straight portion of the cannula) may have a length ranging from about 5 mm to about 50 mm, about 10 mm to about 30 mm, or from about 14 mm to about 20 mm. In some variations, the body may have a length of about 18 mm. The distal curved portion of the cannula may be uniform in cross-sectional shape or it may taper closer to the distal end to facilitate entry into Schlemm's canal. The radius of curvature of the distal curved portion may be adapted to facilitate tangential entry, as well as precise and minimally traumatic entry into Schlemm's canal, and may range from about 1 mm to about 10 mm or from about 2 mm to about 5 mm. In one variation, the radius of curvature is about 2.5 mm. The cannula may also have an angular span suitable for facilitating entry into Schlemm's canal, and may range from about 70 degrees to about 170 degrees, or about 100 degrees to about 150 degrees. In one variation, the angular span is about 120 degrees.

The size, shape, geometry, etc., of the bevel at the distal end of the curved portion of the cannula may be beneficial in allowing easy and minimally traumatic access to Schlemm's canal. In this respect, and as described in further detail below, having a bevel that directly engages the radius of curvature of the distal end of the cannula may be particularly useful.

In other variations, the cannula may include a short straight segment coupled to the distal end of the distal curved portion of the cannula (e.g., at the end of the radius of curvature). Here the bevel engages the straight segment and not the radius of curvature. The length of the straight segment may range from about 0.5 mm to about 5 mm. In some variations, the length of the straight segment ranges from about 0.5 mm to about 3 mm, or from about 0.5 mm to about 1 mm. The length of the straight segment may also less than about 0.5 mm, e.g., it may be about 0.1 mm, about 0.2 mm, about 0.3 mm, or about 0.4 mm. In variations where the bevel directly engages the distal end of the curved portion of the cannula (i.e., the bevel directly engages the radius of curvature), the cannula lacks a straight segment (length of the straight segment is zero).

It may also be useful to have a bevel that is sharp and short to minimize the distance that any ocular device will have to travel when being implanted into the canal. Exemplary bevel angles may range from about 10 degrees to about 90 degrees. In one variation, the bevel angle is about 35 degrees. The bevel may also be oriented in suitable direction. For example, the bevel may be oriented so that it opens up towards the surgeon, or it may be reversed to open away from the surgeon or in any plane in between.

Figure 15:
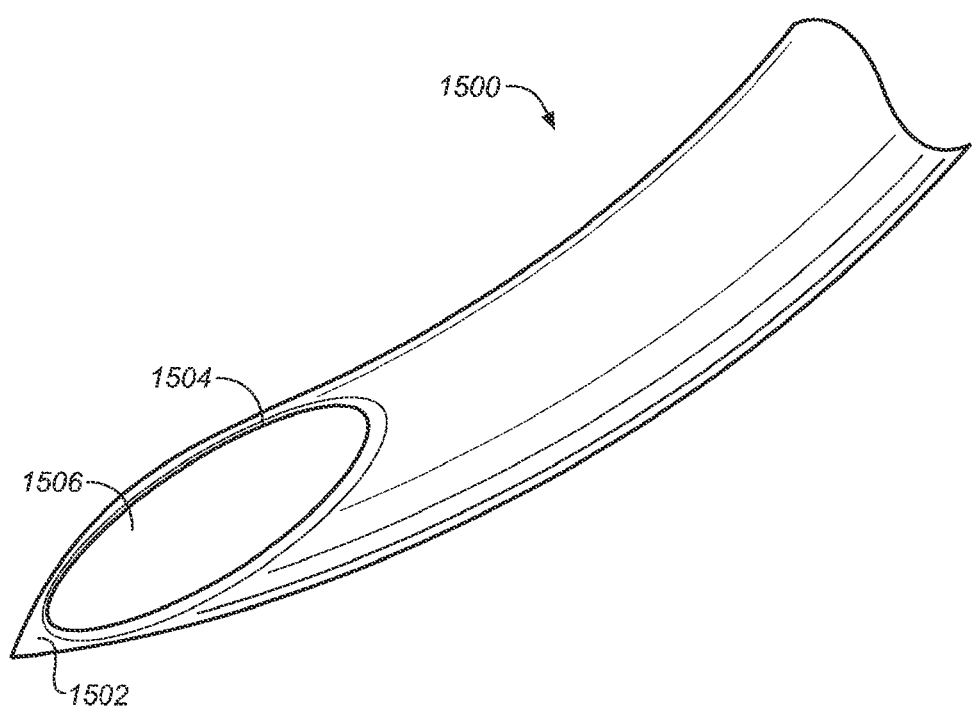
FIG. 15 depicts an exemplary cannula according to another variation.

In yet further variations, the cannula is configured to include one section that is sharp, and another section that is blunt (e.g., deburred). The dual surface configuration of such a cannula may be advantageous since it may provide easier canal access by piercing the meshwork while also providing a gentle, dispersed force on the conduit during conduit retraction into the cannula to avoid cutting or breaking the conduit due to retraction force. For example, as shown in FIG. 15, the distal end of cannula (1500) may have a sharp, piercing tip (1502) and a smooth edge (1504) that define portions of opening (1506), through which 1600 a slidable conduit (not shown) may be advanced and retracted. The sharp tip (1502) may be formed by compounding multiple bevels. The smooth edge (1504) may be created by laser ablation or deburring an inner bevel edge.

Drive Assembly

The drive assembly of the delivery system is generally configured to move an ocular device, conduit, and/or fluid composition out of the universal handle and into Schlemm's canal. The drive assembly may also be configured to position an ocular device within the canal, including advancing the device into the canal and retracting the device from the canal. The drive assembly may be at least partially contained within the housing and may include any suitable component or combination of components capable of providing the handle with universal functionality. In some variations, the drive assembly includes components that translate rotational motion into linear motion. For example, the drive assembly may include a linear gear and a pair of pinion gear mechanisms. The linear gear may have teeth on its surface that engage corresponding teeth on the pinion gears. Each of the pinion gear mechanisms may also be coupled to a rotatable component (e.g., a wheel). Such coupling may be accomplished with a pin that can be threaded through a central opening in the rotatable component and pinion gear, and a nut that secures the rotatable component and pinion gear in a manner so that rotation of the rotatable component also rotates the pinion gear and vice versa. The wheels may be attached to the pinion gear by one of the following methods: 1) the wheels and pinion gears are molded as one part using plastic injection molding technology; 2) the wheels slide onto the pinion gear and secured with adhesive; or 3) the wheels slide on the pinion gear and are mechanically fixed with a fastener or a "press fit", where the wheels are forced onto the pinion gear and friction holds them secure. In all of the mentioned situations, the wheels and pinion gears may rotate coaxially, in the same direction, and at the same angular rate. In some variations, each of the pinion gear mechanisms is coupled to at least two rotatable components. In other variations, the drive assembly may be configured to include a single rotatable component, a plurality of rotatable components, or no rotatable component. The wheel may have markings or colorings to indicate degree of advancement or direction of advancement.

One variation of the drive assembly useful to include in the universal handle comprises a linear gear, a pair of pinion gear mechanisms, and two rotatable components coupled to each pinion gear (for a total of four rotatable components). Here the pinion gear mechanisms and associated wheels would be disposed on either side of the linear gear. The pinion gears and linear gear would contact each other, i.e., the teeth of the pinion gears would directly engage corresponding teeth on the linear gear, and the wheels on one side of the linear gear would contact the wheels on the opposite side of the linear gear. In this variation, the drive assembly can be manipulated with one hand when in a first configuration, and then manipulated with the other hand when flipped over to a second configuration. A drive assembly having such flexible capability can be easily used by a surgeon who is right hand dominant or left hand dominant. In a further variation, the drive assembly may include one rotatable component on one side of the handle and the "universal" feature of the handle provided by a cannula that itself can rotate instead of flipping the handle.

One or both pinion gear mechanisms can be disengaged from the linear gear by biasing their position off axis from the linear gear. This action de-couples the pinion gear teeth to the linear gear teeth to prevent linear gear movement. The pinion gear mechanism can also be locked to prevent rotation by engaging an intersecting pin or feature that prevents wheel rotation.

In other variations, the drive assembly includes a linear gear and a single pinion gear mechanism with two associated wheels. Further variations of the drive assembly may not employ translation of rotational motion to linear motion. For example, a slide (e.g., a finger slide) on the handle that is fixed or detachably coupled to a gear within the housing of the handle (e.g., a linear gear as previously described) could be used to deliver an ocular device or fluid composition. Here the drive assembly may be configured so that advancement of the slide correspondingly advances components that deliver an ocular device or fluid composition into Schlemm's canal, and retraction of the slide correspondingly retracts those components. In yet further variations, a button that can be pressed by one finger or squeezed by two fingers could be employed instead of a slide.

Positioning Element

The ocular delivery systems may further include a slidable positioning element coaxially disposed within the lumen of the cannula for controlled implantation of an ocular device within Schlemm's canal. The positioning element generally comprises a proximal end, a distal end, and an engagement mechanism at the distal end. The ocular device is generally releasably coupled to the engagement mechanism. The positioning element may be advanced to deploy an ocular device within the cannula into Schlemm's canal, or it may be retracted to help with positioning and/or repositioning of an ocular device, or disengagement of an ocular device from the engagement mechanism.

Some variations of the engagement mechanism include a proximal coiled portion and a distal hook. When an implant having at least one fenestration (e.g., a proximal fenestration) is to be implanted, the hook may be releasably engaged to the fenestration. The ocular device may be disengaged from the hook by the application of gentle force on the coil or by another component that can be advanced over the coil to push the device off the hook or by using shape memory materials that passively disengages when exiting the cannula. It may be advantageous to use the hook when retraction of the ocular device is desired. The surgeon may simply move the delivery system and engagement mechanism so that it disengages any fenestration or notch on the implant.

In another variation, the engagement mechanism includes opposing jaws. Here the engagement mechanism may include a first jaw and a second jaw, where the jaws have a closed configuration and an open configuration. The jaws may be used to grip and manipulate the ocular device, and releasably couple the ocular device to the positioning element. The jaws may be formed by splitting or bifurcating the distal end of a wire, e.g., by laser cutting. The grasping force of the jaws may be achieved by constraining the jaws within the cannula. The ocular device may be released once the jaws are advanced out of the cannula and expand. The jaws may also be pivotably connected. In yet another variation, the first jaw may include at least one tine, and the second jaw may include at least one aperture for receiving the tine when the jaws are in the closed configuration.

In further variations, the engagement mechanism comprises a looped portion. This variation of the engagement mechanism will typically be used with an ocular device comprising a spring-like clasp at its proximal end, where the clasp has a collapsed configuration and an expanded configuration. The clasp is generally fabricated in the expanded position. Thus, when a device having a clasp is disposed within the cannula, the first and second arms or tabs of the clasp may collapse around the looped portion of the engagement mechanism. Once the clasped portion of the device has exited the cannula, the arms or tabs may expand to release the ocular device from the looped portion.

Still another variation of the engagement mechanism includes a female to male interface. For example, the engagement mechanism may comprise a notch configured to interface with a complimentary mating element (e.g., a tab) on the ocular device. The notch (female component) may be formed within hypodermic tubing or may be made by creating a fenestration through the distal end of a positioning element made from a solid wire or element, and the tab or hook (male component) may formed as part of the ocular device and may be inserted into the fenestration or notch in the positioning element. With this configuration, the ocular device may be released from the positioning element as it is advanced out of the cannula either by the surgeon's manipulation or by shape setting of the positioning element that causes it to passively detach from the ocular device or both.

Reservoir and Slidable Conduit

The systems generally include a reservoir when a fluid composition is to be delivered into Schlemm's canal. As further described below, the reservoir may be at least partially defined by a fluid assembly and the housing, and the linear gear within the handle. The fluid assembly may be made from any suitable material previously mentioned for the cannula and the housing. The volume of fluid (in microliters) contained within the reservoir may range from about 2 µl to about 1000 or from about 2 µl to about 500 µl. In some variations, the reservoir volume may range from about 50 µl to about 100 µl. Some variations of the fluid assembly include a locking mechanism for preventing movement of the assembly within the handle, e.g., when the linear gear is being advanced or retracted. The locking mechanism may comprise a ratchet pawl, a combination of ratchet pawls or any other suitable mechanism that can be locked to prevent movement of the fluid assembly, and unlocked to allow movement of the fluid assembly.

The fluid composition may be preloaded in the reservoir or loaded into the reservoir prior to use of the system, e.g., at the start of an ocular procedure, so that the fluid can be delivered by a single device and by a single user. Again, this is in contrast to other systems that use forceps or other advancement tools to advance a fluid delivery catheter into Schlemm's canal and/or devices containing viscoelastic fluid that are separate or independent from a delivery catheter or catheter advancement tool, and which require connection to the delivery catheter or catheter advancement tool during a procedure by, e.g., an assistant, or by the hand of the surgeon while the delivery catheter or catheter advancement tool is held by another hand of the surgeon. For example, a loading component may be provided on the fluid assembly for transfer of a fluid composition into the reservoir. The loading component may have any suitable configuration that provides reversible securement of a fluid container, e.g., a syringe, cartridge, etc., to the system, and loading of a fluid composition into the reservoir. The loading component may be a luer fitting or include a one-way valve. A slidable conduit coaxially disposed within the cannula lumen may be operatively connected to the reservoir for delivery of a fluid composition into Schlemm's canal. The slidable conduit generally has a proximal end, a distal end, and a wall that defines a conduit lumen extending therethrough. However, in some instances, the delivery system lacks a slidable conduit, and the fluid composition is delivered solely through the cannula. In other instances, two slidable conduits may be employed that each simultaneously advance through the canal in both clockwise and counterclockwise directions to more rapidly cannulate Schlemm's canal and deliver therapy. As previously stated, the fluid may be delivered in a volume that provides sufficient force to disrupt Schlemm's canal and surrounding trabeculocanalicular tissues. Exemplary disruptive volumes may be about 1 µl, about 2 µl, about 3 µl, about 4 µl, about 5 µl, about 6 µl, about 7 µl, about 8 µl, about 9 µl, about 10 µl, about 11 µl, about 12 µl, about 13 µl, about 14 µl, about 15 µl, about 16 µl, about 17 µl, about 18 µl, about 19 µl, or about 20 µl. In some variations, the disruptive volume fluid may range from about 1 µl to about 50 µl, or from about 20 µl to about 50 µl.

The slidable conduit may be made from any suitable material that imparts the desired flexibility and pushability for introduction through the eye wall, accessing Schlemm's canal, and/or navigation through other ocular tissue structures. For example, the conduit may comprise a polymer; a polymer reinforced with metal wire, braid or coil; composites of polymers and metal; or metals such as stainless steel, titanium, nitinol, or alloys thereof. The slidable conduit may be straight with enough flexibility and pushability to navigate the ring-shaped Schlemm's canal or may be pre-shaped to about a 2-10 mm radius of curvature or about a 6 mm radius of curvature (i.e. the approximate radius of curvature of Schlemm's canal in an adult human) to more easily circumnavigate Schlemm's canal, partially or in its entirety. In some other variations, the slidable conduit includes a plurality of openings through its wall that are spaced along the axial length of the conduit. In this variation, the fluid composition may be delivered from the reservoir through the openings in the conduit and into Schlemm's canal. This lateral ejection of fluid (e.g., a viscoelastic fluid) would further enhance disruption of outflow tissues and enhance permeability to aqueous humor. It is understood that the openings can be of any suitable number, size and shape, and spaced along the axial length of the conduit (including the distal end) in any suitable manner. In other variations, the distal end of the slidable conduit may be configured or modified to aid delivery of the fluid composition into Schlemm's canal. For example, the distal end of the conduit may comprise a cut out configured as a half tube. The distal end of the conduit may also be configured as a blunt bevel, an atraumatic tip, an enlarged atraumatic tip, or a rough surface that disrupts the juxtatrabecular portion of Schlemm's canal or juxtatrabecular meshwork. Additionally, the conduit may have one or more projections emanating from it to further disrupt the juxtatrabecular portion of Schlemm's canal or juxtatrabecular meshwork and thus increase permeability of aqueous humor through the trabecular meshwork into Schlemm's canal. In some instances, the conduit may also deliver energy to the trabeculocanalicular tissues. In other instances, the conduit may be an off the shelf commercially available or customized polypropylene suture (or other material). The suture may be sized so that it can be advanced through the cannula and into a portion of Schlemm's canal (e.g., 0 to 360 degrees of the canal) to disrupt, stent, and/or apply tension to the canal, and/or to tear the trabeculocanalicular tissues. An exemplary range of suture size may range from about 50 microns to about 300 microns. The suture may be removed from the canal or left within the canal to continuously deliver tension on the meshwork and maintain patency of the canal.

The cannula of the systems described herein may also deliver various surgical tools by ab-interno methods. For example, catheters, wires, probes, and other tools may also be employed ab-interno to access Schlemm's canal and then to create holes, partial thickness disruptions, or perforations in discreet locations or all along the trabecular meshwork or inner wall of Schlemm's canal. The surgeon may also advance the tools all the way across the canal and through the collector channel outer wall to access the sclera and subconjunctival space (again all from an ab-interno approach) to make incisions that create a scleral lake into which aqueous can drain to the scleral veins or subconjunctival space or to deliver an ocular device ab-interno that resides and drains into the scleral lake or sub conjunctival space from the anterior chamber or Schlemm's canal.

The reservoir may contain various fluid compositions for delivery into Schlemm's canal. Exemplary fluid compositions include saline and viscoelastic fluids. The viscoelastic fluids may comprise hyaluronic acid, chondroitin sulfate, cellulose, derivatives or mixtures thereof, or solutions thereof. In one variation, the viscoelastic fluid comprises sodium hyaluronate. In another variation, the viscoelastic composition may further include a drug. For example, the viscoelastic composition may include a drug suitable for treating glaucoma, reducing or lowering intraocular pressure, reducing inflammation, and/or preventing infection. Drugs such as an antimetabolite, steroid, heparin, other anticoagulants, and fibrinolytic compounds may also be delivered in combination with the viscoelastic composition. Examples of glaucoma drugs include prostaglandins, beta blockers, miotics, alpha adrenergic agonists, or carbonic anhydrase inhibitors. Anti-inflammatory drugs such as corticosteroids or other steroids may be used. For example, steroids such as prednisolone, prednisone, cortisone, cortisol, triamcinolone, or shorter acting steroids may be employed. Examples of antimetabolites include 5-fluorouracil or mitomycin C. In still another variation, the system delivers the drug alone, without the viscoelastic composition. Saline solution may also be the fluid employed.

In other variations, the devices/systems may include a slidable conduit that does not deliver a fluid, but which is sized to have an outer diameter sufficient to disrupt Schlemm's canal and surrounding trabeculocanalicular tissues. The outer diameter may range from about 50 microns to about 500 microns, from about 300 microns to about 500 microns, from about 200 microns to about 250 microns, or from about 180 microns to about 300 microns. In some instances it may be beneficial for the conduit to have an outer diameter of about 240 microns. Furthermore, a distal portion of the conduit may include a disruptive component, e.g., a notch, hook, barb, or combination thereof, to disrupt tissues.

Figure 2:
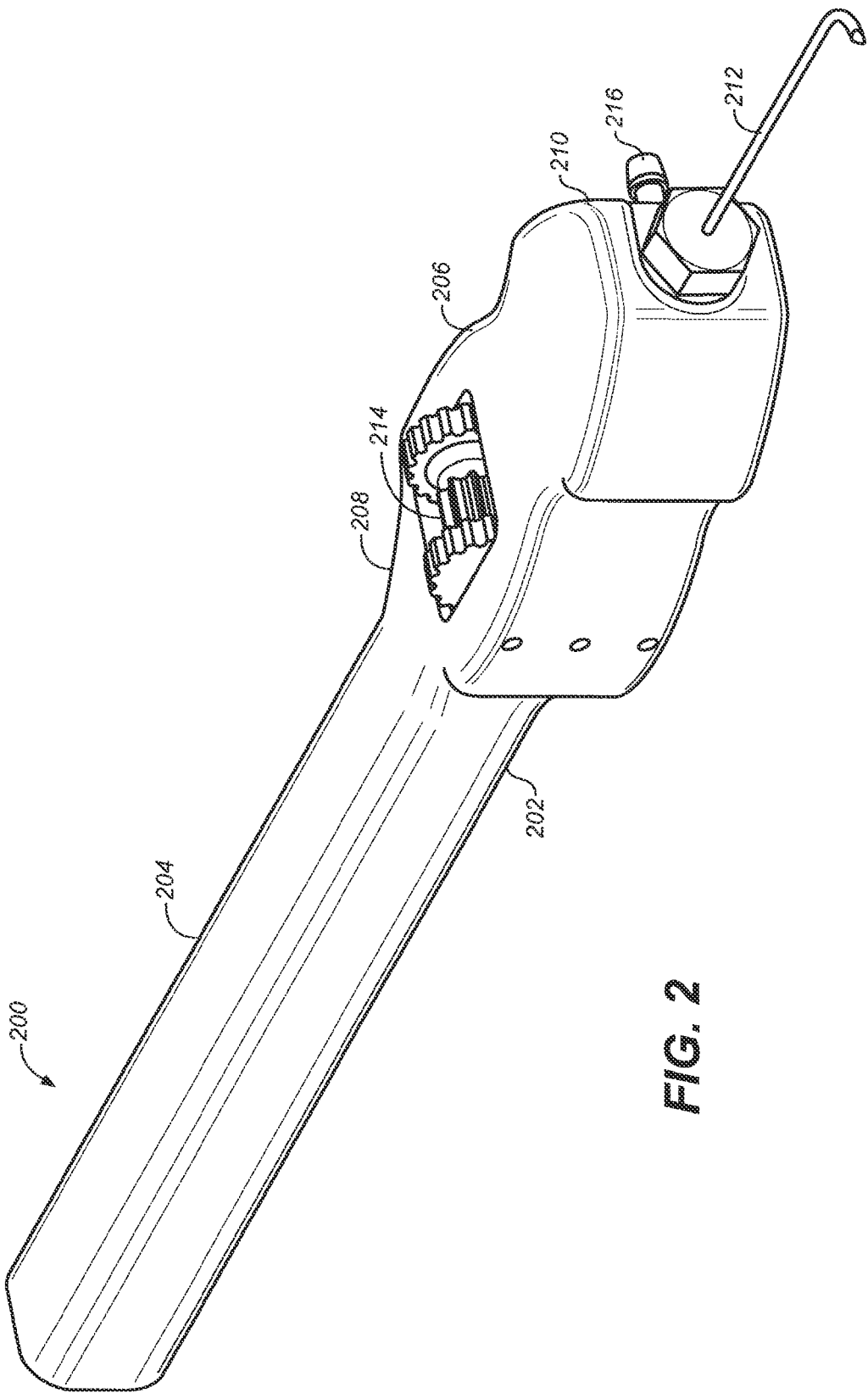
FIG. 2 depicts a perspective view of an exemplary delivery system for implanting an ocular device.

An exemplary ocular delivery system is depicted in FIG. 2. In the figure, delivery system (200) includes a universal handle (202) having a grip portion (204) and a housing (206). The housing has a proximal end (208) and a distal end (210). A cannula (212) is coupled to and extends from the housing distal end (210). A drive assembly (214) is substantially contained within the housing (206) that actuates movement of a positioning element (not shown). Port (216) is provided on the distal end of the housing (210) for removable connection to a source of irrigation fluid.

Figure 3:
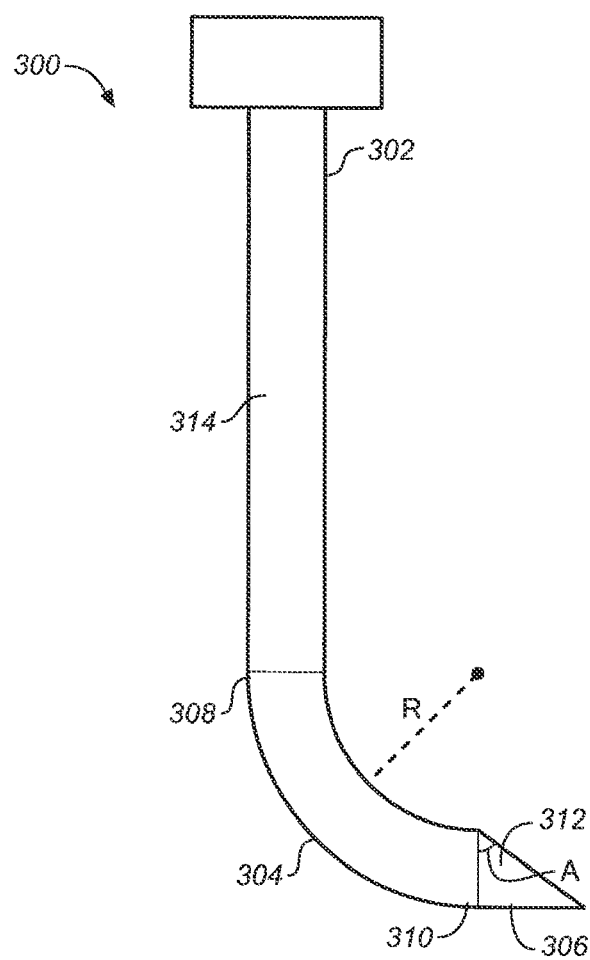
FIG. 3 depicts a side view of an exemplary cannula of the delivery system.

The cannula of an exemplary delivery system is shown in more detail in FIG. 3. Here the cannula (300) comprises a proximal end (302) a distal curved portion (304), a body (314), and a distal tip (306). The distal curved portion (304) has a proximal end (308) and a distal end (310), and a radius of curvature (R) that is defined between the ends (308, 310). A bevel (312) at the distal tip (306) directly engages the distal end of the curved portion of the cannula (310). In other words, the bevel (312) may be contiguous with the distal end of the curved portion of the cannula (310). As previously stated, this configuration of the distal curved portion (304) and bevel (312) may be beneficial or advantageous for allowing easy, atraumatic, and controlled access into Schlemm's canal. The angle of the bevel may also be important. In general, a short bevel may be beneficial. Here the bevel angle (A) is about 35 degrees.

Figure 4A:
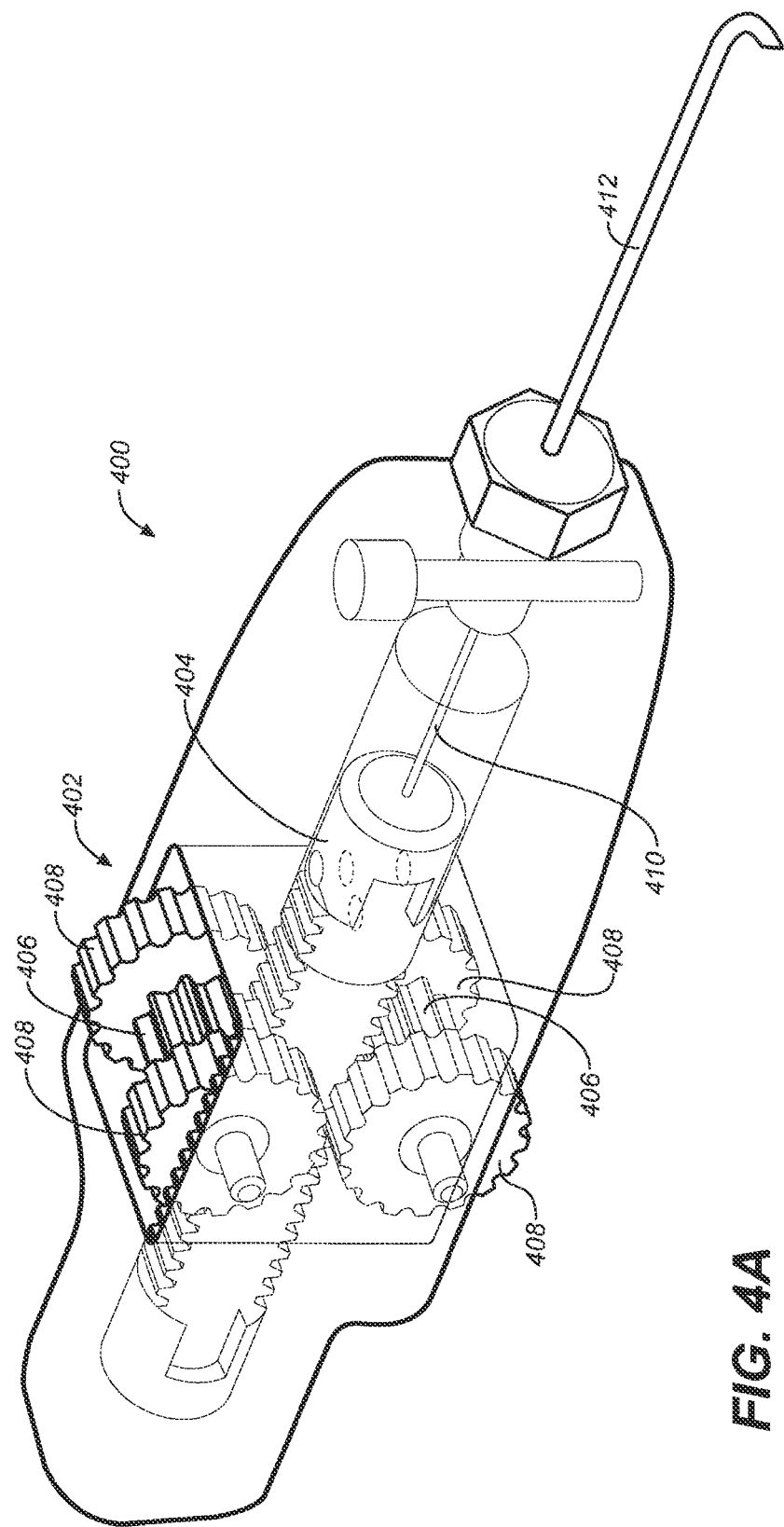
FIGS. 4A-4B depict perspective views of an exemplary drive assembly.
Figure 4B:
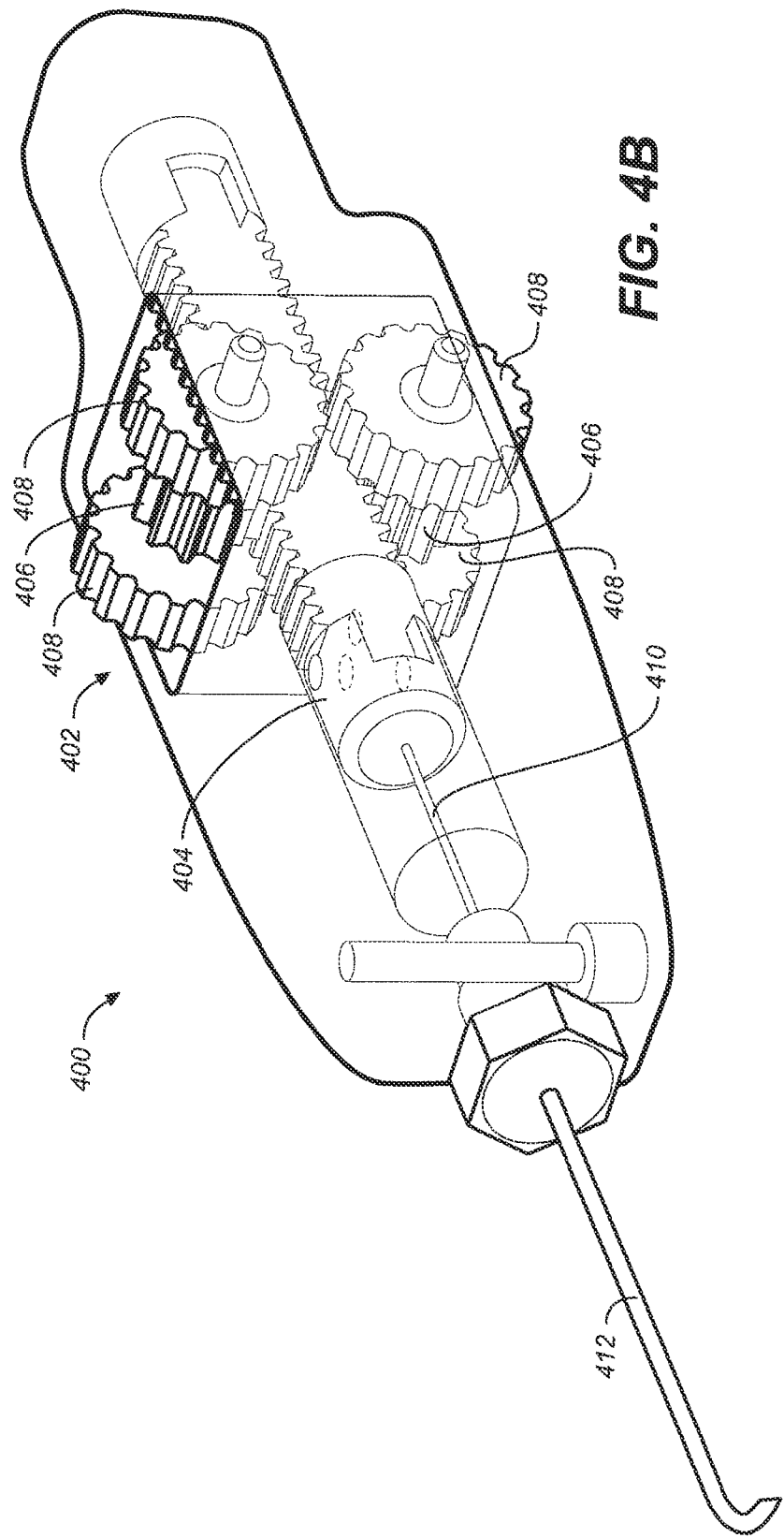

The ocular delivery systems generally include a drive assembly substantially contained within the housing. In the variation shown in FIG. 4A, delivery system (400) includes a drive assembly (402) having a linear gear (e.g., a rack) (404) and a pair of pinion gear mechanisms (406). Both the linear gear and the pinion gear mechanisms have teeth that engage each other to translate rotational motion (of the pinion gear mechanisms 406) to linear motion (of the linear gear 404). Each of the pinion gear mechanisms (406) are coupled to two rotatable components, shown in the figure as wheels (408), for a total of four rotatable components. The wheels (408) may be rotated by one or more of the surgeon's fingers to correspondingly rotate the pinion gear mechanism (406) and thus advance or retract the linear gear (404). The wheels (408) are coaxial with the pinion gear mechanism (406) and rotate in unison with the pinion gear mechanism. Movement of the linear gear (404) advances or retracts a positioning element (410) that is coaxially disposed and slidable within cannula (412). FIG. 4B shows the system of FIG. 4A in a second, flipped orientation that can be used with the opposite hand (e.g., by the left hand if the system of FIG. 4A was used with the right hand), or that can be used by the same hand, but a different direction of cannulation is desired (e.g., clockwise cannulation if counterclockwise cannulation was performed with the system in FIG. 4A).

When the delivery system is used to implant an ocular device, the cannula may have a slidable positioning element coaxially disposed within the cannula lumen. The slidable positioning elements generally include an engagement mechanism for manipulating, e.g., releasably engaging, advancing and/or retracting, an ocular device. Exemplary engagement mechanisms are depicted in FIGS. 5-9.

Figure 5A:
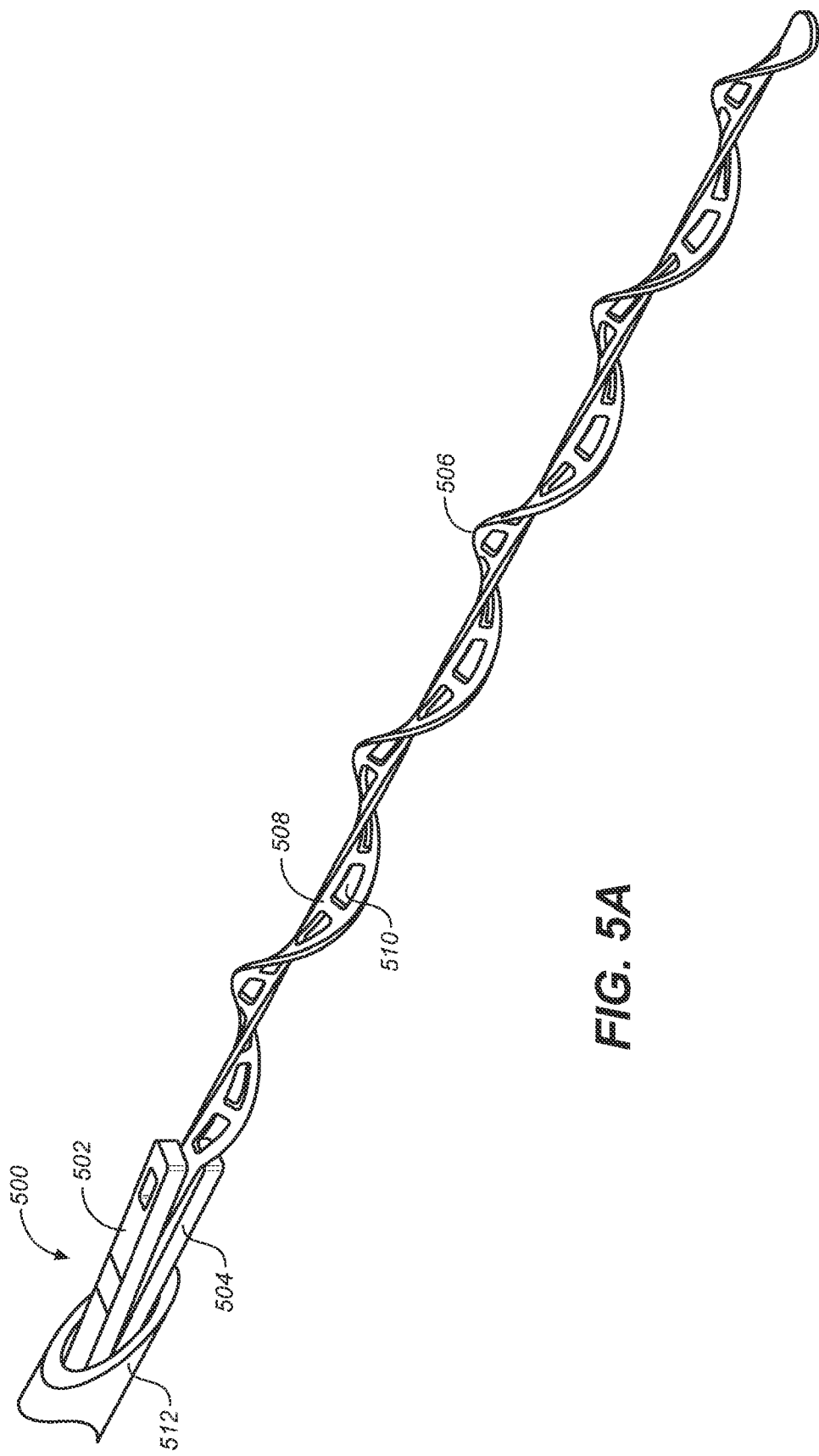
FIGS. 5A-5B show perspective views of an exemplary engagement mechanism.
Figure 5B:
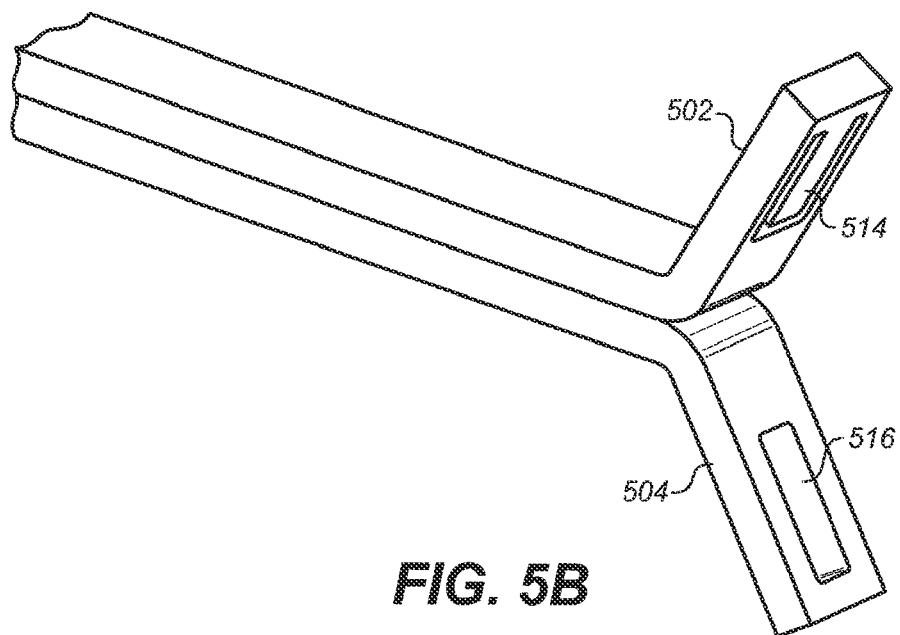
Figure 6:
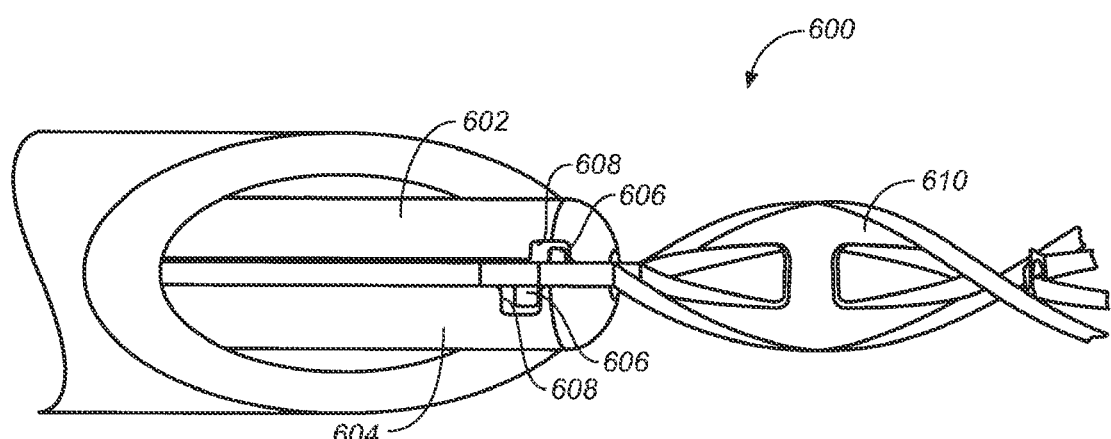
FIG. 6 shows a perspective view of an engagement mechanism according to one variation.

In FIG. 5A, the engagement mechanism (500) comprises a first jaw (502) and a second jaw (504). In their closed configuration (as shown in FIG. 5A), the jaws (502, 504) are constrained within cannula (512) and hold an ocular device (506) comprising a support (508) and at least one fenestration (510). When the jaws (502, 504) are advanced out of cannula (512) they are no longer constrained, and thus take the form of their open configuration, as shown in FIG. 5B. Opening of the jaws (502, 504) releases ocular device (506) from the engagement mechanism (500). At least one tine (514) may be provided in the first jaw (502) and at least one aperture (516) may be provided in the second jaw (504) to help secure a fenestrated ocular device when the jaws are in their closed configuration. In FIG. 6, a variation of an engagement mechanism (600) is shown where a first jaw (602) and a second jaw (604) include both a tine (606) and an aperture (608) to help grasp a fenestrated ocular device (610).

Figure 7A:
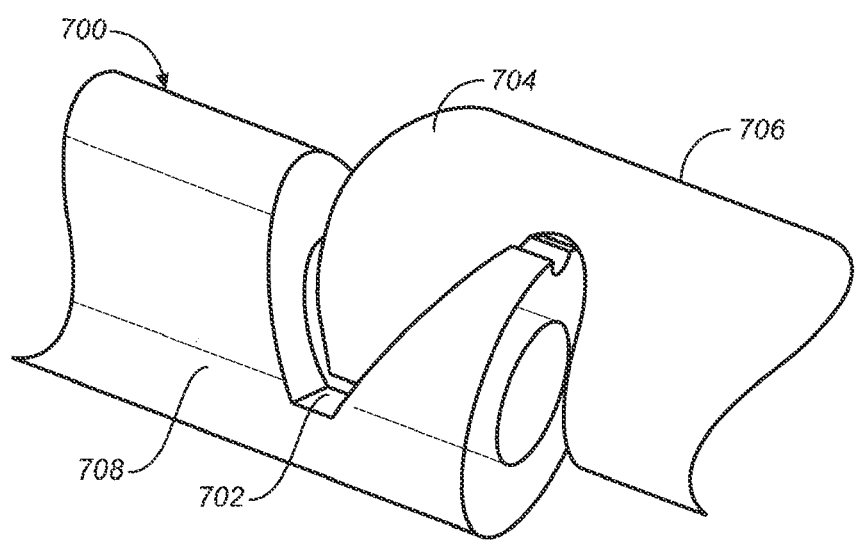
FIGS. 7A-7B show perspective views of engagement mechanisms according to other variations.
Figure 7B:
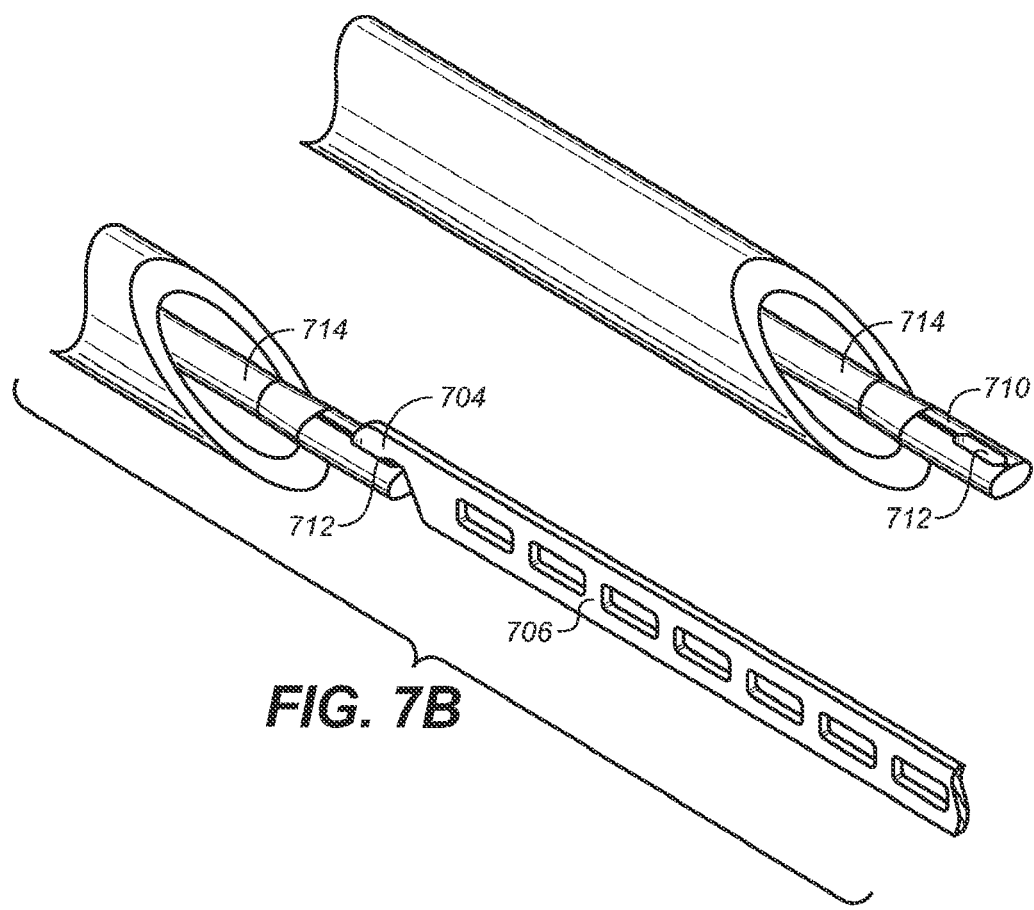

Referring to FIGS. 7A-7B, further exemplary engagement mechanisms are depicted. In FIG. 7A, engagement mechanism (700) comprises complementary mating elements. Specifically, engagement mechanism (700) includes a female element, notch (702) that is configured to interface with a complimentary male element (704), shown as a hook-like projection on the ocular device (706). Here the notch (702) may be fabricated at the end of a hypodermic tube (708) (which would serve as the positioning element). Instead of notch (702), the female element of the engagement mechanism (710) may include an opening (712), as shown FIG. 7B, which interfaces with male element (704) on the ocular device (706). In FIG. 7B, the positioning element (714) may be fabricated from a metal wire or rod and the opening (712) created via laser machining or other processes known in the art.

Figure 8A:
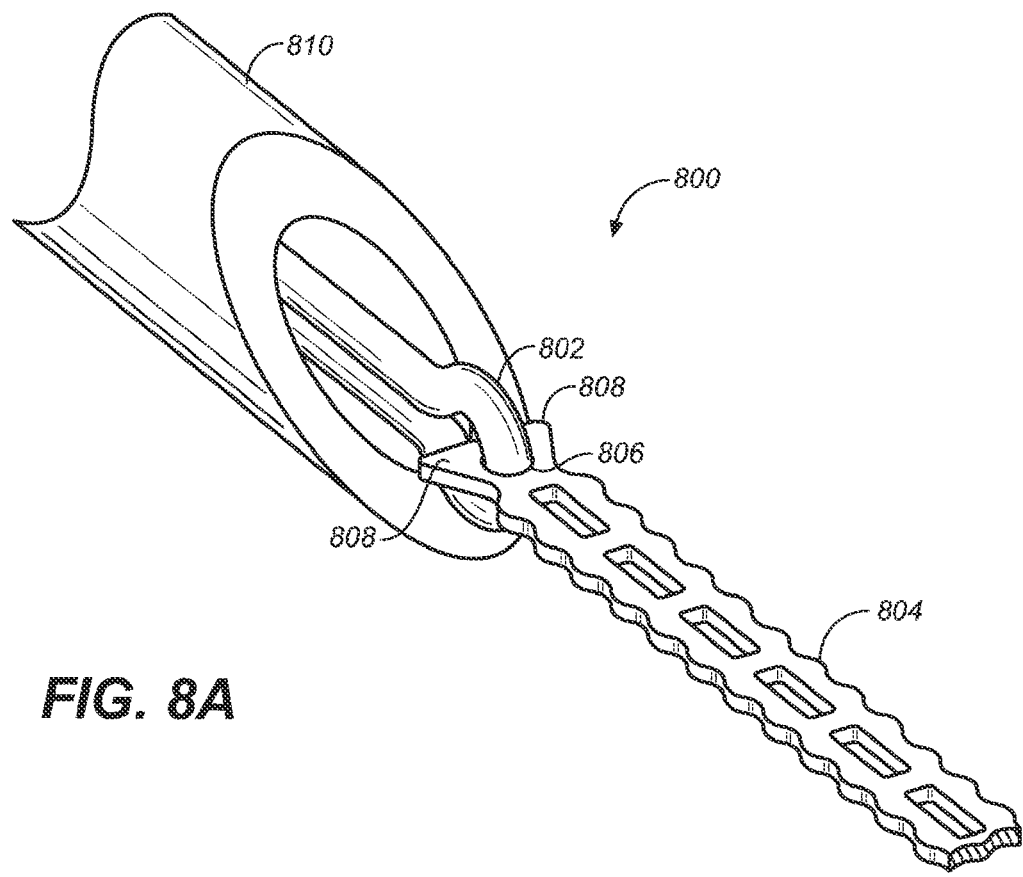
FIG. 8A-8B depict perspective views of an engagement mechanism according to yet a further variation.
Figure 8B:
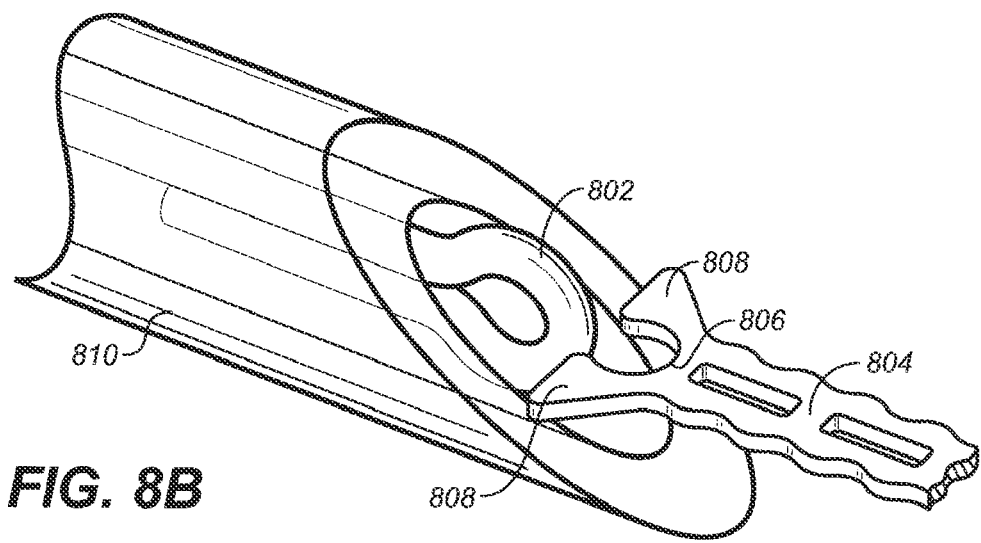

In other variations, the engagement mechanism may be configured as shown in FIGS. 8A and 8B. In those figures, engagement mechanism (800) comprises a looped portion (802). It may be beneficial to use this particular engagement mechanism with an ocular device (804) including a clasp (806) with arms or tabs (808) having a closed configuration and an expanded configuration. Similar to the variation shown in FIGS. 5A and 5B, tabs (808) are constrained in their closed configuration within the cannula (810) prior to advancement out of the cannula (810). In their constrained configuration, tabs (808) engage the looped portion (802) of the engagement mechanism (800) to prevent release of the ocular device (804) from the system. When the looped portion (802) of the engagement mechanism (800) is advanced sufficiently so that tabs (808) are no longer constrained by cannula (810), tabs (808) take on their expanded configuration to thus release the ocular device (804) from the looped portion (802) and into Schlemm's canal, as shown in FIG. 8B.

Figure 9:
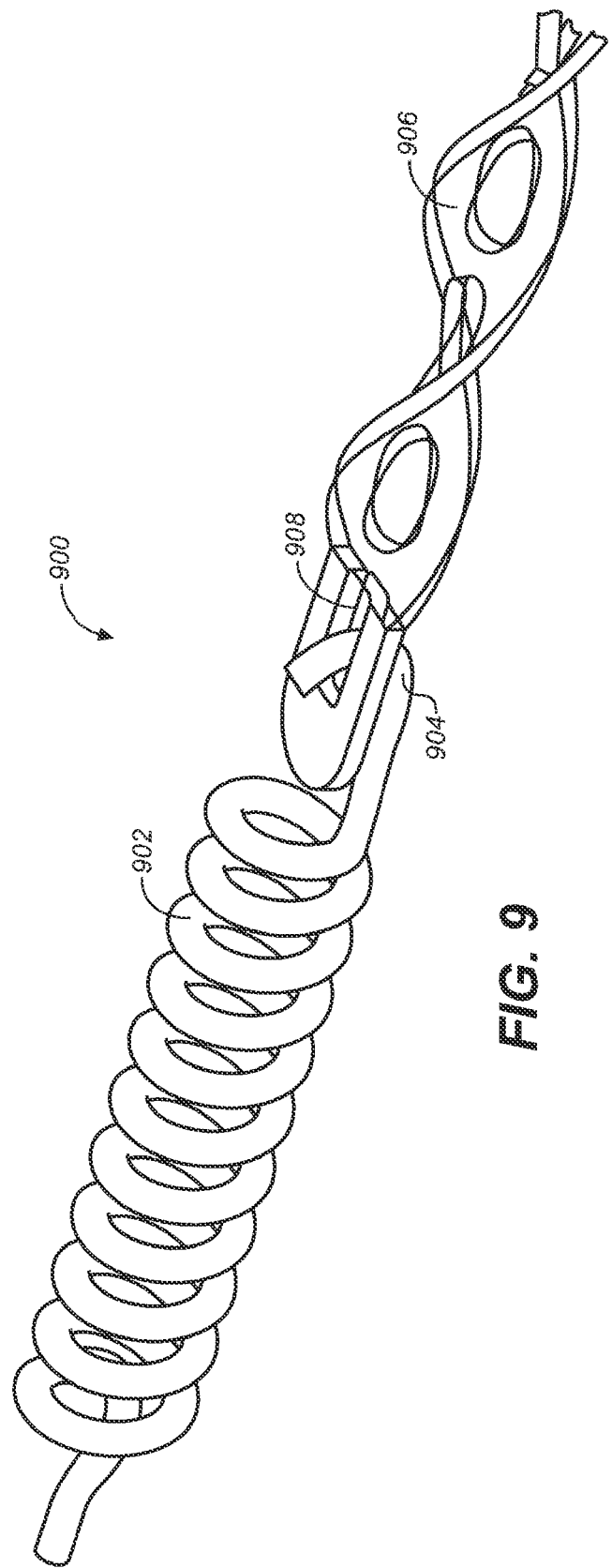
FIG. 9 depicts a perspective view of another exemplary engagement mechanism.

Another exemplary engagement mechanism (900) is shown in FIG. 9 comprising a coiled portion (902) and a hook (904). When an ocular device (906) having at least one fenestration (908) (e.g., a proximal fenestration) is to be implanted, the hook (904) may be releasably engaged to the fenestration (908). The ocular device (906) may be disengaged from the hook by the application of gentle force on the coil (902) or by another component (not shown) that can be advanced over the coil (902) to push the device (906) off the hook (904). It may be advantageous to use the hook (904) when retraction of the ocular device (906) is desired.

Figure 10A:
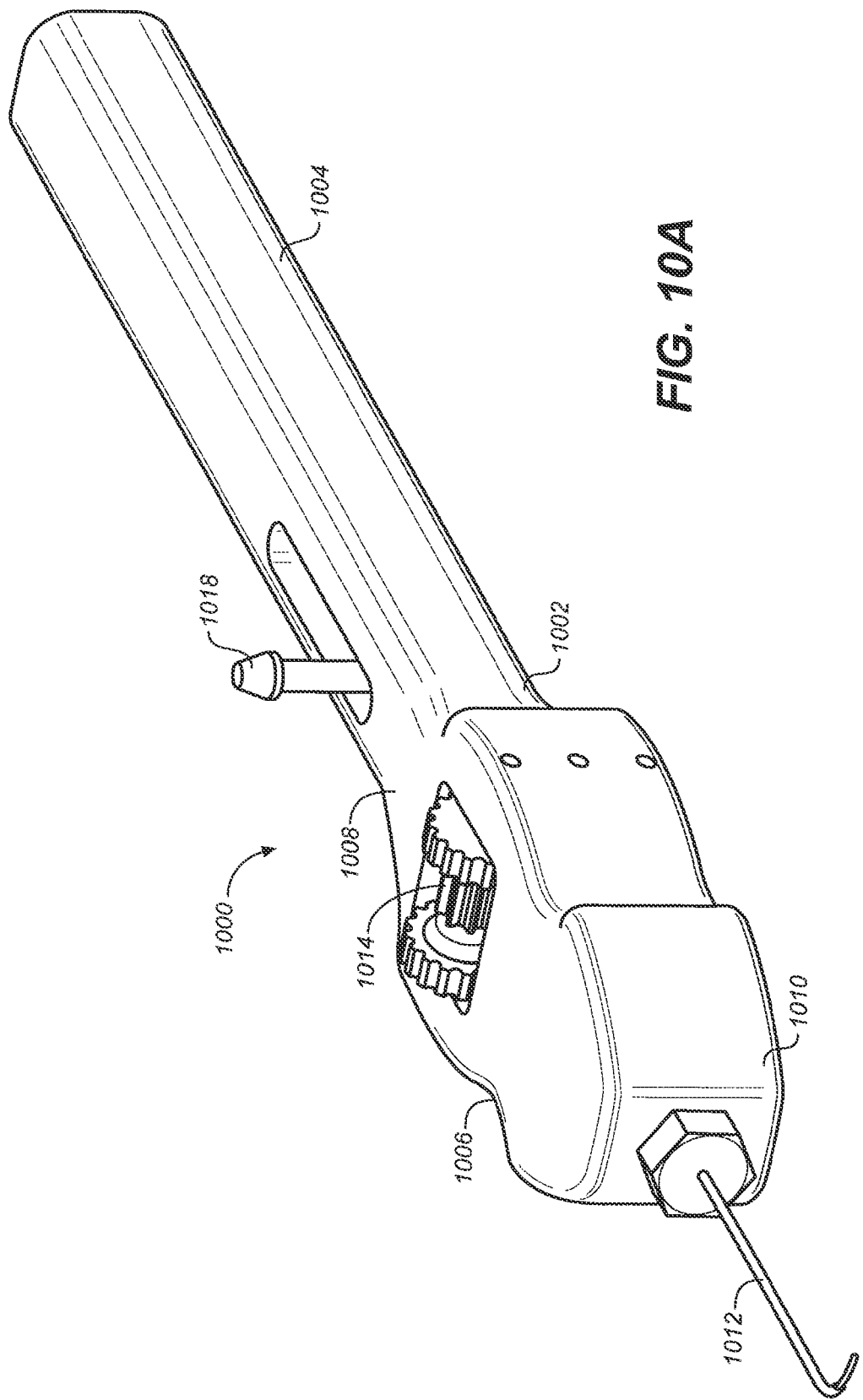
FIGS. 10A-10B show an exemplary delivery system for delivering a fluid composition into Schlemm's canal.
Figure 10B:
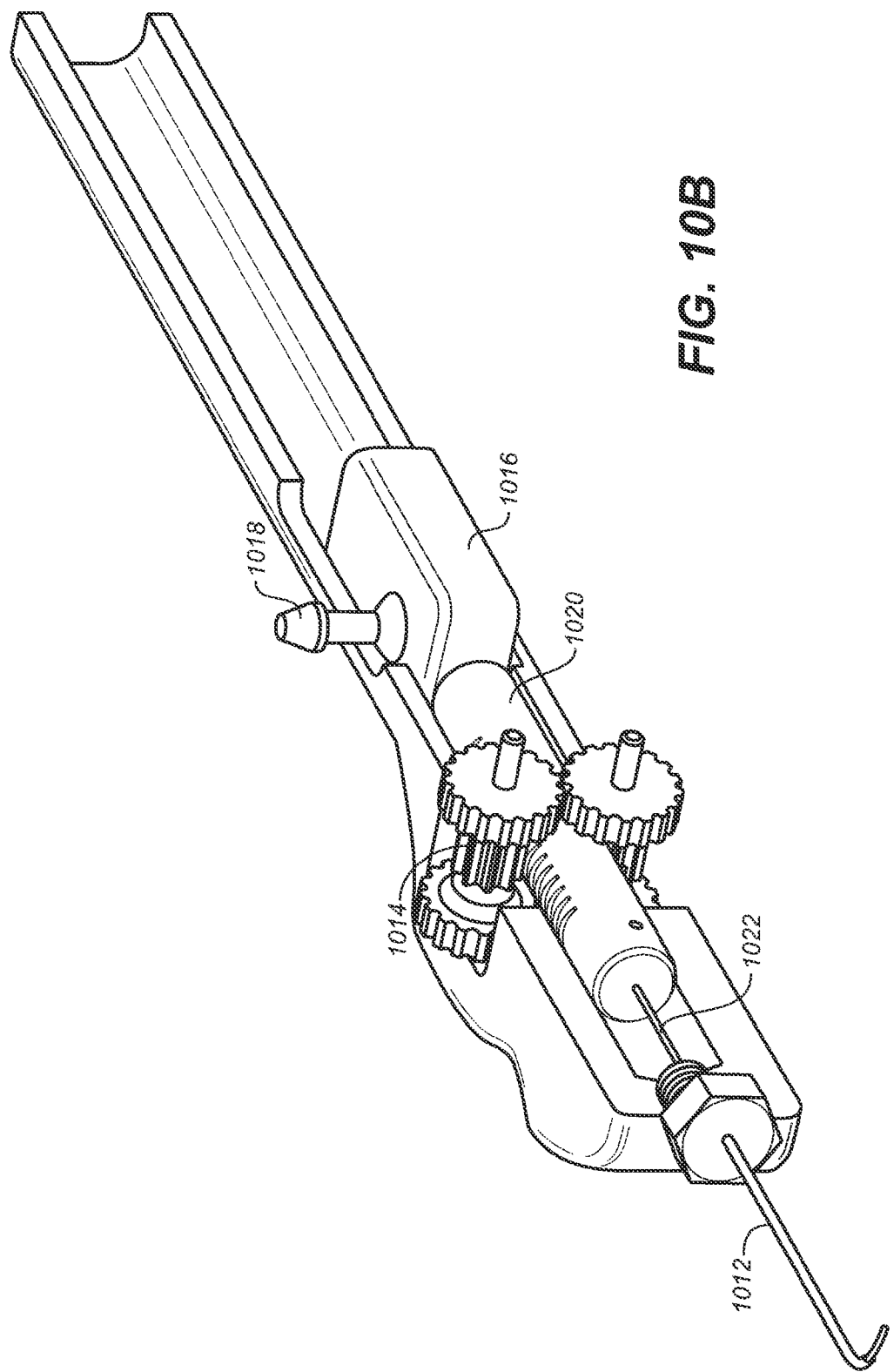

When the delivery systems are employed to deliver a fluid composition, the fluid composition may be preloaded in a reservoir of the system or loaded into the reservoir prior to use of the system. An exemplary delivery system for delivering a fluid composition into Schlemm's canal is shown in FIGS. 10A and 10B. Referring to FIG. 10A, delivery system (1000) includes a universal handle (1002) having a grip portion (1004) and a housing (1006). Housing (1006) has a proximal end (1008) and a distal end (1010). A cannula (1012)) is coupled to and extends from the housing distal end (1010). A drive assembly (1014) is substantially contained within the housing (1006) that actuates movement of a slidable conduit (not shown). The cannula (1012) and drive assembly (1014) have the same configuration as that shown and described in FIGS. 3 and 4A-4B for the system tailored for ocular device implantation, and thus are not described in detail here.

The delivery system (1000) also includes a fluid assembly (1016) (shown in FIG. 10B) within the handle (1002) having a loading component (1018) that is configured to allow transfer of a fluid composition from an external source into a reservoir defined by the fluid assembly and linear gear (1020). A slidable conduit (1022) is coaxially disposed within the cannula lumen that is in fluid communication with the reservoir. As previously stated, in a tool-based system that does not deliver an implant or a fluid, the system may not include a reservoir.

In an exemplary method, as illustrated by FIGS. 11A-11C, a fluid composition may be transferred into a reservoir (1102) of system (1100) via loading through loading component (1104). As shown in the figures, reservoir (1102) is defined by the fluid assembly (1106) and the linear gear (1108). Linear gear (1108) has a proximal end (1110) and a distal end (1112), and a lumen (1114) extending from the proximal end (1110) to the distal end (1112). Lumen (1114) is in fluid communication with the lumen (not shown) of the slidable conduit (1118).

To deploy the fluid composition out of the reservoir (1102), linear gear (1108) is retracted in the direction of the arrow (FIG. 11B) so that reservoir (1102) becomes pressurized. Retraction can be accomplished by rotation of pinion gear mechanisms (1120). Once a sufficient amount of pressure has been created in the reservoir (1102) the fluid composition contained therein is injected through linear gear lumen (1114) and conduit (1118) into Schlemm's canal.

Figure 12:
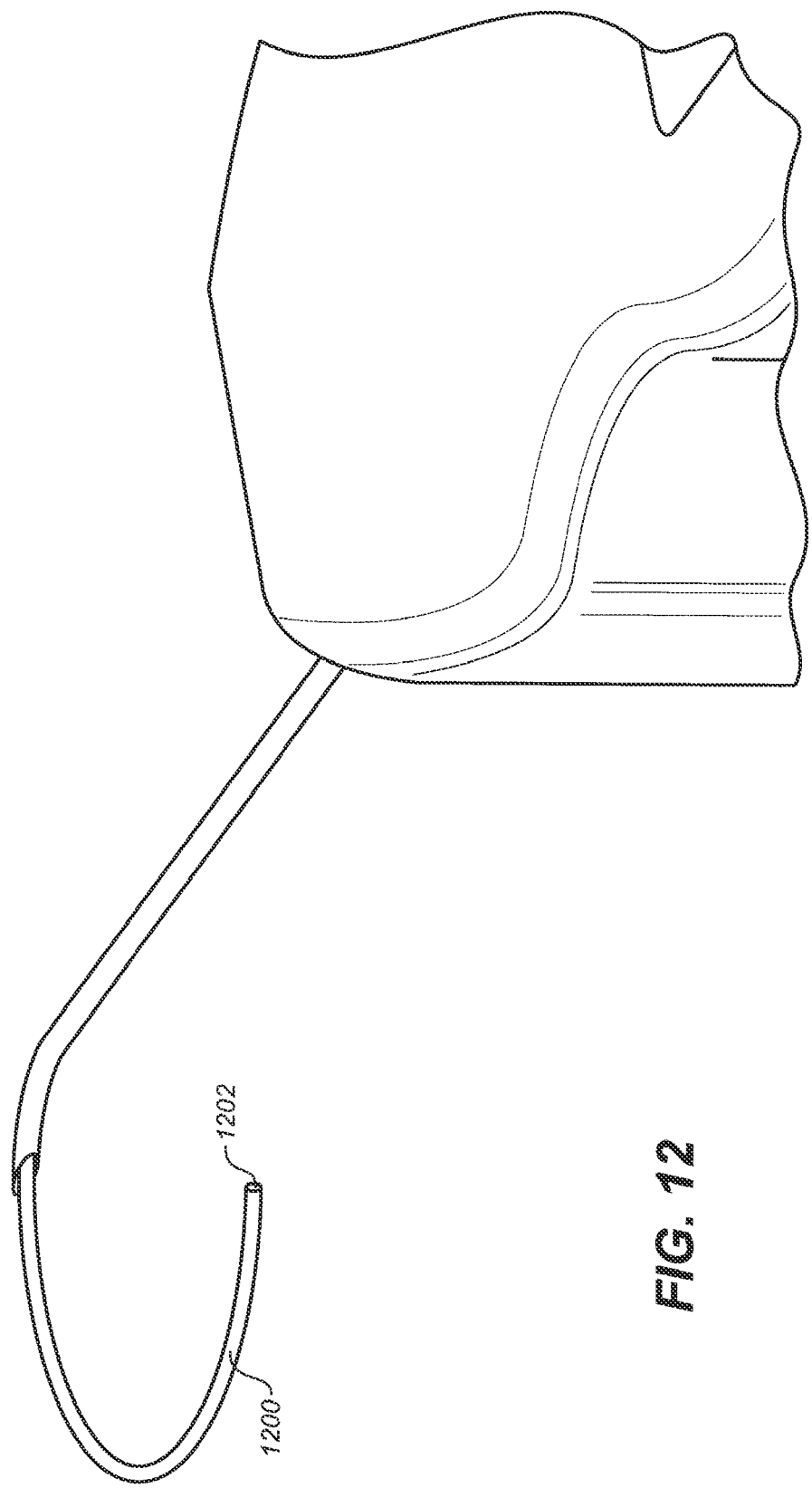
FIG. 12 depicts an exemplary slidable conduit for delivering a fluid composition.
Figure 13A:
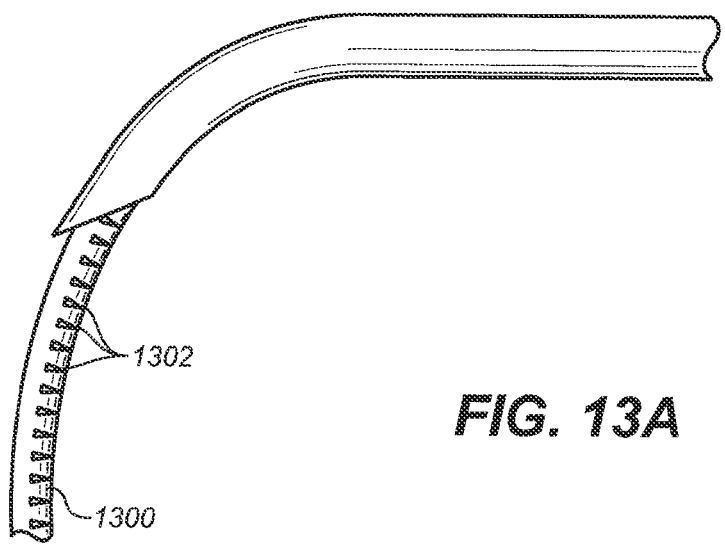
FIGS. 13A-13C show side or perspective views of slidable conduits according to other variations.
Figure 13B:
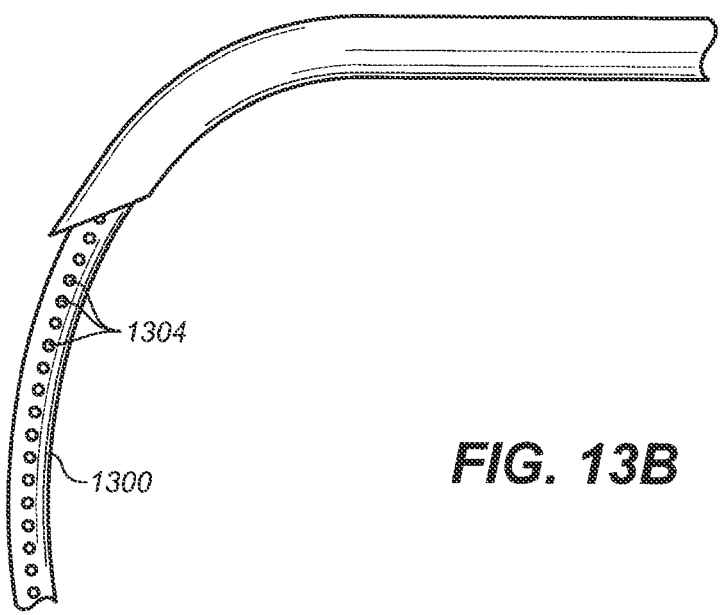
Figure 13C:

The slidable conduits employed with the systems described herein may be of various configurations. For example, as shown in FIG. 12, the conduit (1200) may be a flexible tube having a lumen in fluid communication with an opening at the distal end (1202). Here, any fluid that is delivered flows through the distal end (1202) to reach Schlemm's canal. In other variations, the slidable conduit (1300) may be configured to include a plurality of openings spaced along its axial length. The openings may have any suitable shape, e.g., slots (1302) (FIG. 13A) or circles (1304) (FIG. 13B). Fluid compositions delivered using the conduits depicted in FIG. 13A and FIG. 13B may partially flow out of the conduit through the openings and partially out through the distal end of the conduit. The distal end of the conduit may also be configured as a half tube (1306) (FIG. 13C).

II. Methods

Methods for implanting an ocular device and for delivering a fluid composition into Schlemm's canal using the systems described above are also provided. Implant-free methods for providing a force sufficient to disrupt trabeculocanalicular tissues, e.g., by providing a disruptive volume of viscoelastic fluid or a disruptive tool, are further described. The methods are generally single-handed, single-operator controlled methods that are minimally invasive, e.g., they are tailored for an ab-interno procedure, which as previously mentioned, can be advantageous over the more invasive ab-externo approach. However, use of the ocular systems in an ab-externo method may be contemplated in some instances and thus, are not excluded here. The methods for delivering an ocular device or fluid, or for providing a disruptive force, may be used to treat glaucoma, pre-glaucoma, or ocular hypertension. When treating glaucoma, the methods may also be used in conjunction with a cataract surgery (before or after) using the same incision.

In general, the methods for implanting an ocular device within Schlemm's canal first include the step of creating an incision in the ocular wall (e.g., the sclera or cornea) that provides access to the anterior chamber of the eye. As shown in the stylized depiction of an eye in FIG. 14, the cannula (1400) of the ocular delivery system is then advanced through the incision and at least partially across the anterior chamber (1402) to the trabecular meshwork (not shown). Schlemm's canal (i.e., the lumen of Schlemm's canal) (1404) is then accessed with the distal curved portion of the cannula (1406) and a slidable positioning element, (or, e.g., a slidable tool or guidewire), or slidable conduit (represented generically by element 1408) is advanced from the cannula to implant an ocular device within Schlemm's canal, perform a procedure within Schlemm's canal or on any of the neighboring trabeculocanalicular tissues, or deliver a fluid into the canal. However, in some instances, a slidable conduit may not be employed so that any fluid to be delivered is delivered through the cannula. In yet further variations, just the trabecular meshwork is punctured and the fluid composition is delivered without circumnavigation of Schlemm's canal.

As previously stated, the cannula may be configured to include a proximal end and a distal curved portion, where the distal curved portion has a proximal end, a distal end, and a radius of curvature defined between the ends. Here the cannula may also include a body and a distal tip having a bevel that directly engages the radius of curvature, e.g., it is contiguous with the radius of curvature. The method may also include the step of flushing the system with fluid (e.g., to remove air from the system) and/or the step of irrigating the operative field to clear away blood or otherwise improve visualization of the field.

Any suitable ocular device that maintains the patency of Schlemm's canal or improves outflow of aqueous humor may be implanted by the systems described herein. For example, ocular devices that maintain the patency of Schlemm's canal without substantially interfering with fluid flow across and along the canal may be implanted. Such devices may comprise a support having at least one fenestration, as disclosed in U.S. Pat. No. 7,909,789, which is incorporated by reference herein in its entirety. Ocular devices that disrupt the juxtacanalicular trabecular meshwork or adjacent inner wall of Schlemm's canal may also be implanted. In addition to ocular devices made from metal or metal alloys, the use of sutures, modified sutures, modified polymers, or solid viscoelastic structures may be delivered. Fluid compositions such as saline, viscoelastic fluids, air, and gas may also be delivered.

When a fluid composition is delivered into Schlemm's canal, the methods generally include the steps of creating an incision in the ocular wall (e.g., the sclera or cornea) that provides access to the anterior chamber of the eye; advancing a cannula of the ocular delivery system through the incision and at least partially across the anterior chamber to the trabecular meshwork; accessing Schlemm's canal with the cannula; and delivering the fluid composition into the canal using a conduit slidable within the cannula lumen. The cannula may be configured to include a proximal end and a distal curved portion, where the distal curved portion has a proximal end, a distal end, and a radius of curvature defined between the ends. Here the cannula may also include a body and a distal tip having a bevel that directly engages the radius of curvature, e.g., it is contiguous with the radius of curvature. Further advantageous cannula features may also be included, which are described above. The method may also include the step of flushing the system with fluid (e.g., to remove air from the system) and/or the step of irrigating the operative field to clear away blood or otherwise improve visualization of the field.

When an ab-interno method is employed for implanting an ocular device, the method may include the following steps. The surgeon may first view the anterior chamber and trabecular meshwork (with underlying Schlemm's canal) using an operating microscope and a gonioscope or gonioprism. Using a 0.5 mm or greater corneal, limbal, or sclera incision, the surgeon may then gain access to the anterior chamber. A saline solution or viscoelastic composition may then be introduced into the anterior chamber to prevent its collapse. Here the saline solution or viscoelastic composition may be delivered through the delivery system cannula or by another mode, e.g., by infusion through a sleeve on the cannula. The surgeon, under direct microscopic visualization, may then advance the cannula of the delivery system through the incision towards the anterior chamber angle. When nearing the angle (and thus the trabecular meshwork), the surgeon may apply a gonioscope or gonioprism to the cornea to visualize the angle. The application of a viscous fluid (e.g., a viscoelastic composition as previously described) to the cornea and/or gonioscope or gonioprism may help to achieve good optical contact. As the surgeon visualizes the trabecular meshwork, the cannula may then be advanced so that the bevel of at the distal end of the curved distal portion of the cannula pierces the meshwork and is in communication with the lumen of Schlemm's canal. The surgeon may irrigate saline or a viscoelastic composition into the canal or into the anterior chamber to either prevent collapse of chamber, dilate Schlemm's canal, or wash away any blood that may obscure visualization of cannula and ocular device delivery. Next, when the ocular device is advanced to the extent desired by the surgeon, it is released from the engagement mechanism so that it can reside in Schlemm's canal. If repositioning of the ocular device is needed or desired, the surgeon may retract and/or reposition the ocular device using the positioning element of the delivery system. The surgeon may then withdraw the delivery system from the eye.

Other variations of the ab-interno method for implanting an ocular device include the use of an endoscope. Similar to the method above, access to the anterior chamber is first made by incising the cornea, limbus, or sclera. Again, this may be done in combination with cataract surgery in one sitting, either before or after cataract surgery, or independently. The anterior chamber may be infused with saline solution or a viscoelastic composition may be placed in the anterior chamber to prevent its collapse. The saline or viscoelastic may be delivered as a separate step or it may be infused with the conduit of the delivery system, a sleeve on the conduit, or with a separate infusion cannula. The surgeon, under direct microscopic visualization, then advances the endoscope through the incision and towards the angle and trabecular meshwork. As the surgeon visualizes the trabecular meshwork using the endoscope or any associated video display, the bevel of the cannula is advanced to pierce the meshwork. The ocular device is then advanced using the positioning element under endoscopic visualization. The surgeon may irrigate saline or a viscoelastic composition into the canal or into the anterior chamber to either prevent collapse of chamber, dilate Schlemm's canal, or wash away any blood that may obscure visualization of cannula and ocular device delivery. When the ocular device is advanced to the extent desired by the surgeon, it is released from the engagement mechanism so that it can reside in Schlemm's canal. If repositioning of the ocular device is needed or desired, the surgeon may retract and/or advance the ocular device using the positioning element of the delivery system. The surgeon may then withdraw the delivery system from the eye.

With respect to the delivery of a fluid composition, the methods are similar to the implantation of an ocular device. However, instead of using a positioning element, the delivery system employs a slidable conduit to infuse a fluid composition into Schlemm's canal. The surgeon may first view the anterior chamber and trabecular meshwork (with underlying Schlemm's canal) using an operating microscope and a gonioscope or gonioprism. Using a 0.5 mm or greater corneal, limbal, or sclera incision, the surgeon may then gain access to the anterior chamber. A saline solution or viscoelastic composition may then be introduced into the anterior chamber to prevent its collapse. Here the saline solution or viscoelastic composition may be delivered through the delivery system cannula or by another mode, e.g., by infusion through a sleeve on the cannula. The surgeon, under direct microscopic visualization, may then advance the cannula of the delivery system through the incision towards the anterior chamber angle. When nearing the angle (and thus the trabecular meshwork), the surgeon may apply a gonioscope or gonioprism to the cornea to visualize the angle. The application of a viscous fluid (e.g., a viscoelastic composition as previously described) to the cornea and/or gonioscope or gonioprism may help to achieve good optical contact. As the surgeon visualizes the trabecular meshwork, the cannula may then be advanced so that the bevel of at the distal end of the curved distal portion of the cannula pierces the meshwork and is in communication with the lumen of Schlemm's canal. Next, a slidable conduit coaxially disposed within the cannula lumen may be advanced into the canal under gonioscopic visualization. The slidable conduit may be advanced any suitable amount and direction about the canal. For example, the slidable conduit may be advanced between about 10 degrees to about 360 degrees about the canal, or it may be advanced in two steps, e.g., 180 degrees in a clockwise direction and 180 degrees in a counterclockwise direction about the canal (to thereby achieve a full 360 degree ab-interno viscocanalostomy or canaloplasty). Fluid may be injected upon advancement or retraction of the conduit. Once the slidable conduit has been positioned within the canal, a fluid composition, e.g., a viscoelastic solution, may be continuously or intermittently delivered through the conduit. The fluid composition may exit the conduit through its distal end (e.g., the through the distal tip), or through openings or fenestrations provided along its shaft, or a combination of both. The openings or fenestrations may be spaced along the axial length of the conduit in any suitable manner, e.g., symmetrically or asymmetrically along its length. Other substances such as drugs, air, or gas may delivered be in the same manner if desired.

The slidable conduit may be repositioned by retraction or repeated advancement and retraction. In some variations of the method, the same or different incision may be used, but the delivery system cannula is employed to access and dilate Schlemm's canal from a different direction (e.g., counterclockwise instead of clockwise). Once a sufficient amount of fluid has been delivered, the surgeon may retract the slidable conduit into the cannula and remove the delivery system from the eye. It should be understood that these steps may be used alone or in combination with cataract surgery (in one sitting).

Other variations of the ab-interno method for delivering a fluid composition include the use of an endoscope. Similar to the method described directly above, access to the anterior chamber is first made by incising the cornea, limbus, or sclera. Again, this may be done in combination with cataract surgery in one sitting, either before or after cataract surgery, or independently. The anterior chamber may be infused with saline solution or a viscoelastic composition may be placed in the anterior chamber to prevent its collapse. The saline or viscoelastic may be delivered as a separate step or it may be infused with the conduit of the delivery system, a sleeve on the conduit, or with a separate infusion cannula. The surgeon, under direct microscopic visualization, then advances the endoscope through the incision and towards the angle and trabecular meshwork. As the surgeon visualizes the trabecular meshwork via the endoscope or any associated display, the bevel of the cannula is advanced to pierce the meshwork. The slidable conduit is then advanced under endoscopic visualization. The slidable conduit may be advanced any suitable amount and direction about the canal. For example, the slidable conduit may be advanced between about 10 degrees to about 360 degrees about the canal, or it may be advanced in two steps, e.g., 180 degrees in a clockwise direction and 180 degrees in a counterclockwise direction about the canal (to thereby achieve a full 360 degree ab-interno viscocanalostomy). Once the slidable conduit has been positioned within the canal, a fluid composition, e.g., a viscoelastic fluid, may be continuously or intermittently delivered through the conduit. The fluid composition may exit the conduit through its distal end (e.g., the through the distal tip), or through openings or fenestrations provided along its shaft, or a combination of both. The openings or fenestrations may be spaced along the axial length of the conduit in any suitable manner, e.g., symmetrically or asymmetrically along its length. Other substances such as drugs, air, or gas may be delivered in the same manner if desired.

The slidable conduit may be repositioned by retraction or repeated advancement and retraction. In some variations of the method, the same or different incision may be used, but the delivery system cannula is employed to access and dilate Schlemm's canal from a different direction (e.g., counterclockwise instead of clockwise). Once a sufficient amount of fluid has been delivered, the surgeon may retract the slidable conduit into the cannula and remove the delivery system from the eye.

An ab-externo approach to implanting an ocular device or delivering a fluid composition may include additional or slightly different steps. For example, the creation of tissue flaps, suturing, etc., may be part of the ab-externo method. In general, the ab-externo method for implanting an ocular device may include the following steps. First, under microscopic visualization, conjunctiva is incised, a scleral flap is created and tissue is dissected to identify the ostia into Schlemm's canal. The anterior chamber may be separately infused with saline or may have a viscoelastic composition placed in it to prevent collapse of the anterior chamber angle. The operation may be done as a standalone procedure or in combination with cataract surgery in one sitting. It may also be done before the cataract surgery portion or after it.

Using the delivery system described herein, the cannula may be advanced into Schlemm's canal and the ocular device advanced using the positioning element under direct microscopic visualization or through a gonioscope or gonioprism. When the ocular device is advanced the desired amount, the surgeon may release the ocular device from the positioning element by actuating the engagement mechanism and remove the delivery system from the eye and operating field. The scleral wound is then closed, using for example, sutures or tissue adhesive. If repositioning of the ocular device is needed or desired, the surgeon may retract and/or advance the ocular device using the positioning element of the delivery system.

With respect to the delivery of a fluid composition, the ab-externo method is similar to ab-interno delivery. However, instead of using a positioning element, the delivery system employs a slidable conduit to infuse a fluid composition into Schlemm's canal. First, under microscopic visualization, conjunctiva is incised, a scleral flap is created and tissue is dissected to identify the ostia into Schlemm's canal. The anterior chamber may be separately infused with saline or may have a viscoelastic composition placed in it to prevent collapse of the anterior chamber angle. The operation may be done as a standalone procedure or in combination with cataract surgery in one sitting. It may also be done before the cataract surgery portion or after it.

Using the delivery system described herein, the cannula may be advanced into Schlemm's canal and a slidable conduit coaxially disposed within the cannula lumen may be advanced into the canal under gonioscopic visualization. Once the slidable conduit has been positioned within the canal, a fluid composition, e.g., a viscoelastic fluid, may be continuously or intermittently delivered through the conduit. The fluid composition may exit the conduit through its distal end (e.g., the through the distal tip), or through openings or fenestrations provided along its shaft, or a combination of both. The openings or fenestrations may be spaced along the axial length of the conduit in any suitable manner, e.g., symmetrically or asymmetrically along its length. Other substances such as drugs, air, or gas may delivered be in the same manner if desired. The slidable conduit may be repositioned by retraction or repeated advancement and retraction. The delivery system may then be removed from the eye.

The fluid compositions may be delivered in a manner where retraction of a system component allows advancement of the fluid out of the system cannula. Referring again to FIGS. 11A-11C, linear gear (1108) is retracted in the direction of the arrow (FIG. 11B) so that reservoir (1102) becomes pressurized. Retraction can be accomplished by rotation of pinion gear mechanisms (1120). Once a sufficient amount of pressure has been created in the reservoir (1102) the fluid composition contained therein is injected through linear gear lumen (1114) and conduit (1118) into Schlemm's canal. It should be understood that the ocular delivery systems may be configured so that the fluid compositions are delivered continuously, passively, automatically, or actively by the surgeon. The fluid compositions may also be delivered to the canal independent of the gear shaft movement with a pump or auxiliary plunger.

The fluid compositions that may be delivered by the ocular systems described herein include saline and viscoelastic fluids. The viscoelastic fluids may comprise hyaluronic acid, chondroitin sulfate, cellulose, derivatives or mixtures thereof, or solutions thereof. In one variation, the viscoelastic fluid comprises sodium hyaluronate. In another variation, the viscoelastic composition may further include a drug. For example, the viscoelastic composition may include a drug suitable for treating glaucoma, reducing or lowering intraocular pressure, reducing inflammation or scarring, and/or preventing infection. The viscoelastic composition may also include agents that aid with visualization of the viscoelastic composition. For example, dyes such as but not limited to fluorescein, trypan blue, or indocyanine green may be included. In some variations, a fluorescent compound or bioluminescent compound is included in the viscoelastic composition to help with its visualization. In other variations, the system delivers the drug alone, without the viscoelastic composition. In this case, the drug may be loaded onto or into a sustained release biodegradable polymer that elutes drug over a period of weeks, months, or years. It is also contemplated that air or a gas could be delivered with the systems.

The fluid compositions may be delivered to dilate Schlemm's canal. The entire length of Schlemm's canal or a portion thereof may be dilated by the fluid. For example, at least 75%, at least 50%, at least 25%, or at least 10% of the canal may be dilated. The fluid compositions may also be delivered to treat various medical conditions, including but not limited to, glaucoma, pre-glaucoma, and ocular hypertension.

Additionally, the fluid compositions may be delivered to restore the tubular anatomy of Schlemm's canal, to clear obstructions within the canal, to disrupt juxtacanalicular trabecular meshwork or the inner wall of Schlemm's canal within the canal, or to expand the canal. Here the delivery systems may include wires, tubes, balloons, instruments that deliver energy to the tissues, and/or other features to help with these methods. It is contemplated that glaucoma may be treated using such systems with additional features. The surface of these systems may also be roughened or have projections to further disrupt the inner wall of Schlemm's canal and juxtacanalicular trabecular meshwork to enhance aqueous humor outflow or permeability.

Figure 16:
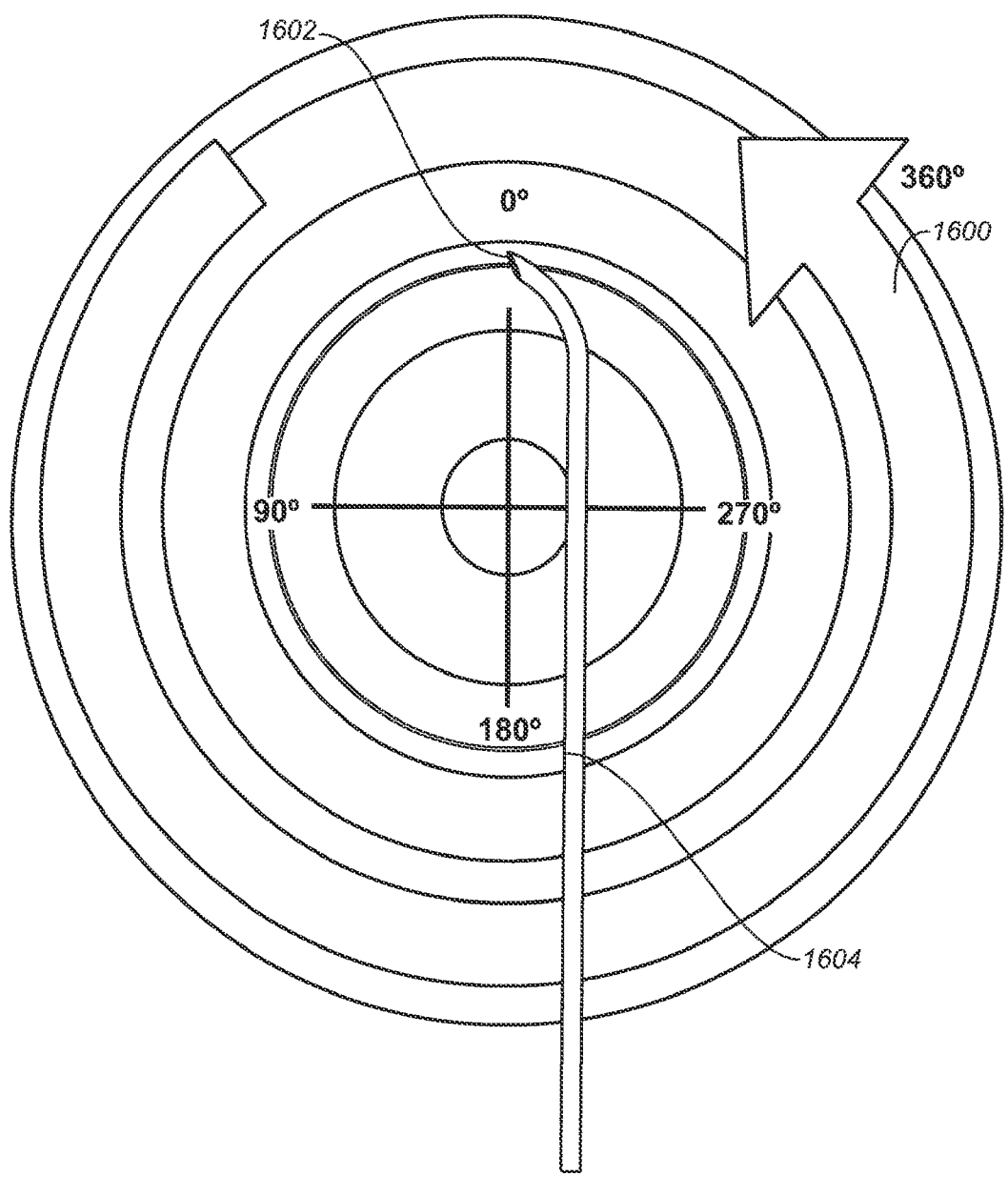
FIG. 16 is a stylized depiction of an ab-interno method of accessing Schlemm's canal from a single point, and delivering a viscoelastic fluid while advancing a fluid delivery conduit along a 360 degree arc of the canal.
Figure 17:
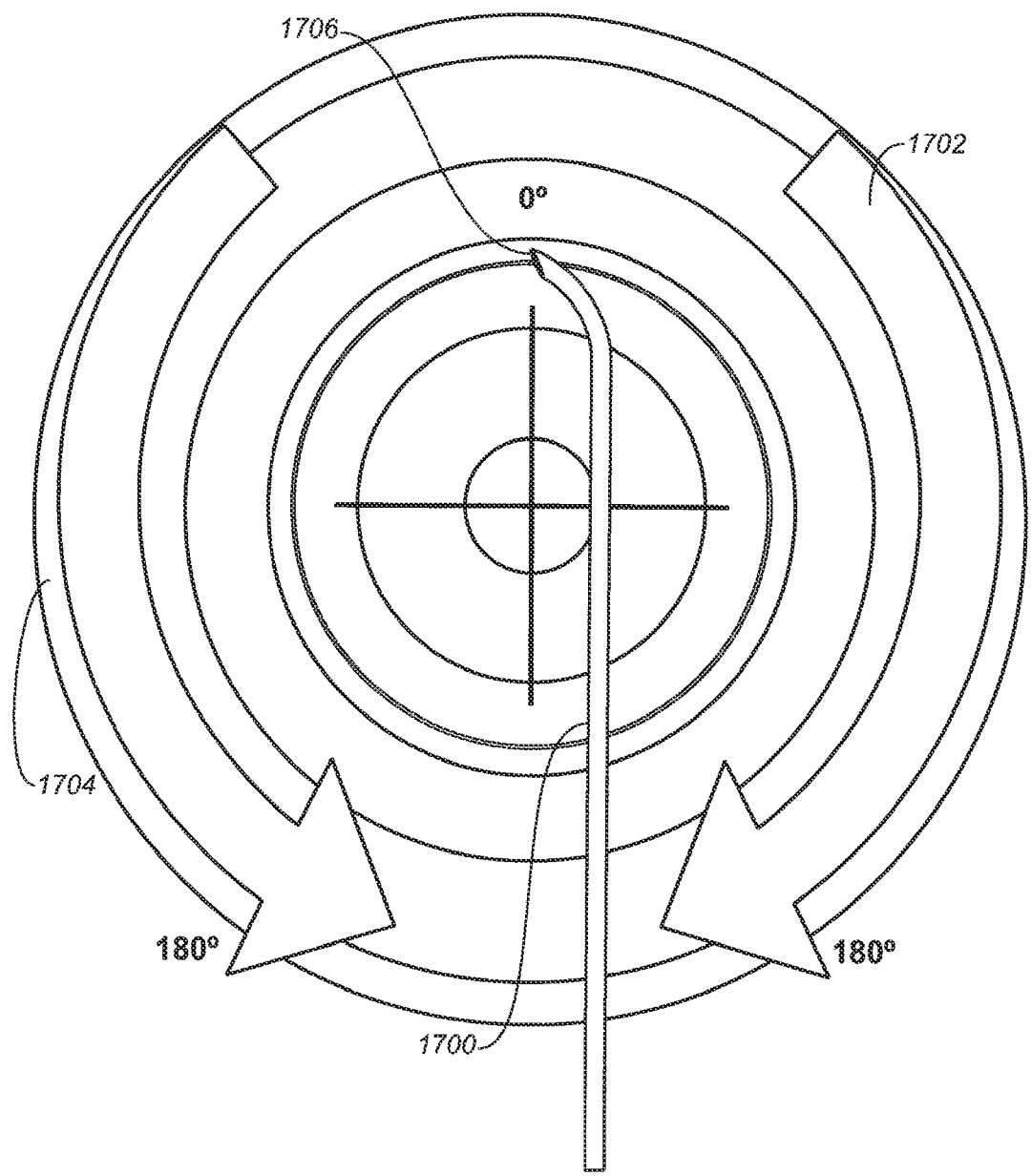
FIG. 17 is a stylized depiction of an ab-interno method of accessing Schlemm's canal from a single point, and delivering a viscoelastic fluid while advancing a fluid delivery conduit in both the clockwise and counterclockwise directions along a 180 degree arc of the canal.

When the systems and devices are tailored to provide a disruptive force to the trabeculocanalicular tissues, implant-free methods may be employed, e.g., by delivering a disruptive volume of viscoelastic fluid, advancing disruptive tools, e.g., cannulas, conduits, catheters, etc., including one or more disruptive components on their distal portions, or both. Exemplary disruptive components include, without limitation, notches, hooks, barbs, or combinations thereof. Depending on factors such as the type or severity of the condition being treated, the disruptive force may be generated to partially or completely destroy and/or remove the trabecular meshwork, and may be adjusted by varying the volume of viscoelastic fluid delivered, or by varying the tool configuration. Exemplary volumes of viscoelastic fluid that may be sufficient to provide a disruptive force may range from about 1 µl to about 50 µl, from about 1 µl to about 30 µl, or from about 2 µl to about 16 µl. In one variation, a volume of about 4 µl is sufficient to disrupt Schlemm's canal and/or the surrounding tissues. In other variations, the volume of viscoelastic fluid sufficient to disrupt trabeculocanalicular tissues may be about 2 IA, about 3 µl, about 4 µl, about 5 µl, about 6 µl, about 7 µl, about 8 µl, about 9 µl, about 10 µl, about 11 µl, about 12 µl, 13 µl, about 14 µl, about 15 µl, about 16 µl, about 17 µl, about 18 µl, about 19 µl, about 20 µl, about 25 µl, about 30 µl, about 35 µl, about 40 µl, about 45 µl, or about 50 µl. The total volume of viscoelastic fluid may be delivered along a 360 degree arc (1600) of Schlemm's canal during a single advancement from a single access point (1602) in the canal (e.g., as shown in FIG. 16) or withdrawal of the conduit (1604), or along lesser degrees of arc in multiple advancements or withdrawals of the conduit. For example, as shown in FIG. 17, a conduit (1700) may be advanced along a 180 degree arc of the canal in both clockwise (1702) and counterclockwise (1704) directions to deliver fluid from, e.g., a single access point (1706) in the canal. Referring to FIGS. 16 and 17, an exemplary disruptive volume of, 4 µl may be delivered along a 360 degree arc of the canal while the conduit is advanced from a single access point in the canal, or 2 µl may be delivered along a 180 degree arc of the canal during two advancements (one in the clockwise direction and the other in the counterclockwise direction) of the conduit from a single access point in the canal. The conduit may access the canal from a single point or from multiple points. The amount or degree of tissue disruption may be varied by the volume of fluid delivered. For example, 8 µl may be used to perforate or gently tear the meshwork, while 16 µl may be used to maximally tear the meshwork. More specifically, about 1 to 2 µl may be used to dilate Schlemm's canal and collector channels; about 2 to 4 µl may be used to dilate Schlemm's canal and collector channels, and disrupt/stretch juxtacanalicular tissues; and about 4 to 6 µl may be used for all the foregoing and for the creation of microtears in the trabecular meshwork and juxtacanalicular tissues (further increasing porosity and outflow). A volume of about 8 to 16 µl may be used for all the foregoing and for substantial perforation/tearing of the trabecular meshwork and juxtacanalicular tissues. A volume of about 16 to 50 µl may be used for substantial or complete tearing of the trabecular meshwork. When fluids are not used, and only a disruptive tool is employed, the outer diameter of the conduit or tool may be variously sized for disruption of tissues, analogous to how fluid volumes may be varied to vary the level of disruption. For example, a conduit or tool having an outer diameter ranging from about 50 to about 100 microns may be advanced through the canal to slightly dilate the canal and break or remove septae obstructing circumferential canalicular flow. A conduit or tool having an outer diameter ranging from about 100 to 200 microns may be employed to perform the foregoing, and may also to begin to stretch the trabecular meshwork and juxtacanalicular tissues. A conduit or tool having an outer diameter ranging from about 200 to about 300 microns may be able to perform the above, but may also create microtears in the trabecular meshwork and juxtacanalicular tissues, and may maximally dilate the collector channels. A conduit or tool having an outer diameter ranging from about 300 to about 500 microns may maximally disrupt the tissues and may create tears or perforations all along the trabecular meshwork and juxtacanalicular tissues. Additionally, the further the advancement of the conduit or tool through the canal, the greater the efficacy of the procedure. For example, the conduit or tool may be advanced out from the tip of the cannula and into the canal about a 30 degree arc of the canal (e.g., advanced about 3 to 4 mm out of the cannula), advanced about a 60 degree arc of the canal (e.g., advanced about 6 to 8 mm out of the cannula), advanced about a 90 degree arc of the canal (e.g., advanced about 10 mm out of the cannula), advanced about a 120 arc of the canal (e.g., advanced about 15 mm out of the cannula), advanced about a 180 degree arc of the canal (e.g., advanced about 20 mm out of the cannula), or advanced about a full 360 degrees of the canal (e.g., advanced about 36 to 40 mm out of the cannula), for maximal efficacy and maximal intraocular pressure reduction.

The implant-free methods for treating conditions of the eye may include advancing a conduit into Schlemm's canal, where the conduit has been loaded with a volume of viscoelastic fluid, and delivering the viscoelastic fluid into Schlemm's canal at a volume sufficient to disrupt the trabeculocanalicular tissues to reduce intraocular pressure. However, the implant-free methods for treating conditions of the eye may not necessarily include delivery of viscoelastic fluids. In these instances, the method may comprise advancing a device into Schlemm's canal, where the device has a diameter between about 300 and about 500 microns, or about 150 and about 200 microns, and where advancement of the device into Schlemm's canal disrupts the canal and/or trabeculocanalicular tissues in a manner sufficient to reduce intraocular pressure.

Other methods for treating conditions of the eye may be single-handed, single-operator methods for introducing viscoeleastic fluid into Schlemm's canal that include advancing a conduit into Schlemm's canal, where the conduit has been loaded with a volume of viscoelastic fluid, and delivering the viscoelastic fluid into Schlemm's canal, where delivering the volume of viscoelastic fluid is accomplished by a single-handed device used by a single operator.

Again, when viscoelastic fluids are delivered in the methods disclosed herein, the disruptive volume may be between about 2 µl to about 8 µl. It may be beneficial to deliver a volume of about 4 µl of viscoelastic fluid in certain instances. The viscoelastic fluid may be delivered while advancing the conduit of a single-handed, single-operator controlled device from Schlemm's canal in the clockwise direction, counterclockwise direction, or both, or during withdrawal of the conduit from Schlemm's canal. As previously stated, the viscoelastic fluid may be delivered to disrupt Schlemm's canal and surrounding trabeculocanalicular tissues. For example, the delivered viscoelastic fluid may cause disruption by dilating Schlemm's canal, increasing the porosity of the trabecular meshwork, stretching the trabecular meshwork, forming microtears in juxtacanalicular tissue, removing septae from Schlemm's canal, dilating collector channels, or a combination thereof. The conduit may be loaded with the viscoelastic fluid at the start of an ocular procedure so that the fluid can be delivered by a single device. This is in contrast to other systems that use forceps or other advancement tool to advance a fluid delivery catheter into Schlemm's canal and/or devices containing viscoelastic fluid that are separate or independent from a delivery catheter or catheter advancement tool, and which require connection to the delivery catheter or catheter advancement tool during a procedure by an assistant while the delivery catheter or catheter advancement tool is held by the surgeon.

In some variations, the methods disclosed herein may include advancement of the conduit (or a tool) about a 360 degree arc of Schlemm's canal, about a 270 degree arc of Schlemm's canal, about a 120 degree arc of Schlemm's canal, about a 180 degree arc of Schlemm's canal, or about a 90 degree arc of Schlemm's canal. In yet further variations, advancement of the conduit (or a tool) may be about a 0 to 5 degree arc of Schlemm's canal, about a 30 degree arc of Schlemm's canal, or about a 60 degree arc of Schlemm's canal. Advancement may occur from a single access point in Schlemm's canal or from multiple access points in the canal. When a disruptive force is to be provided, it may be beneficial to advance the conduit in both clockwise and counterclockwise directions about a 180 degree arc of Schlemm's canal from a single access point in the canal.

Prior to the introduction of goniotomy and trabeculotomy (both of which are typically used to treat an obstructed trabecular meshwork, often genetically-driven at a young age), congenital glaucoma uniformly resulted in blindness. Despite the invasiveness of goniotomy (which is performed ab-interno, but a sharp scalpel is used to cut 30-60 degrees of meshwork to improve outflow) and trabeculotomy (ab-externo method where deep scleral incisions unroof Schlemm's canal and the meshwork is cut with a probe), the procedures are viewed as being effective and have allowed many pediatric patients to avoid an entire lifetime of blindness. In 1960, Burian and Smith each independently described trabeculotomy ab-externo. In this highly invasive ab-externo operation, the surgeon makes a deep scleral incision, finds Schlemm's canal, cannulates all 360 degrees of Schlemm's canal externally with a catheter or specially designed probe called a trabeculotome, and finally tensions both ends of the catheter or probe to the point where the trabeculotome cuts through the entire trabecular meshwork into the anterior chamber to improve drainage.

More recent attempts at decreasing the invasiveness of ab-externo trabeculotomy have been developed by NeoMedix, which commercializes a device called "Trabectome". The Trabectome attempts to make trabeculotomy easier by using an ab-interno approach. The instrument and methods involve removal of the trabecular meshwork ab interno by electrocautery using an instrument that also provides infusion and aspiration. The disadvantages of the Trabectome are three-fold: 1) the device employs an energy-based mechanism to ablate trabecular meshwork, which is believed to cause inflammation and scarring in the eye, which in turn can adversely impact outflow and pressure; 2) the device/procedure is ergonomically limited—it requires a foot pedal and power cords to activate electrocautery and irrigation in addition to being limited to 60-120 degrees of meshwork therapy per corneal or scleral entry incision; and 3) Because it involves energy-based ablation and irrigation, there is a significant capital equipment cost that may limit adoption.

The methods (as well as systems and devices) described herein, including the method for providing a disruptive force to trabeculocanalicular tissues, may be highly suitable for ab-interno trabeculotomy and goniotomy given that they avoid the use of electrocautery, and are capable of advancing conduits over larger degrees of arc of Schlemm's canal. In some variations of the ab-interno trabeculotomy and goniotomy methods, the procedure includes advancing a cannula at least partially through the anterior chamber of the eye, entering Schlemm's canal at a single access point using the cannula, and delivering a volume of a viscoelastic fluid through a conduit slidable within, and extendable from, the cannula, sufficient to disrupt the structure of Schlemm's canal and surrounding tissues to reduce intraocular pressure. Other methods that may be useful in treating conditions of the eye include the steps of entering Schlemm's canal using a conduit extendable from a single-operator controlled handle, the handle comprising a fluid reservoir, and delivering a volume of a viscoelastic fluid from the fluid reservoir through the conduit by increasing pressure within the fluid reservoir, where the volume of delivered viscoelastic fluid is sufficient to disrupt the structure of Schlemm's canal and surrounding tissues to reduce intraocular pressure. The disruptive volume may be between about 2 µl to about 16 µl. In one variation, the disruptive volume is about 4 µl of viscoelastic fluid. As previously stated, in some instances the disruptive volume may range anywhere between about 20 µl to about 50 µl.

More specifically, disruption (e.g., cutting, destruction, removal, etc.) of the trabecular meshwork may be accomplished by removing the cannula from the eye while leaving the conduit in the canal, thereby tearing through the meshwork. Alternatively, tissue disruption may occur by viscodilating excessively and intentionally with at least about 1 µl, at least about 2 µl, at least about 3 µl, at least about 4 µl, at least about 5 µl, at least about 6 µl, at least about 7 µl, at least about 8 µl, at least about 9 µl, at least about 10 µl, at least about 11 µl, at least about 12 µl, at least about 13 µl, at least about 14 µl, at least about 15 µl, at least about 16 µl, at least about 17 µl, at least about 18 µl, at least about 19 µl, or at least about 20 µl of viscoelastic fluid per 360 degree arc of the canal. The amount or degree of tissue disruption may be varied by the volume of fluid delivered. For example, 8 µl may be used to perforate or gently tear the meshwork, while 16 µl may be used to maximally tear the meshwork. In some variations, at least about 20 µl, at least about 25 µl, at least about 30 µl, at least about 35 µl, at least about 40 µl, at least about 45 µl, or at least about 50 µl of viscoelastic fluid may be delivered.

Another method for disrupting tissues may include using oversized conduits (e.g., having an outside diameter of 300-500 microns) to tear the meshwork upon delivery, or inflating or expanding the conduit once it has been fully advanced into Schlemm's canal to stretch, disrupt, rupture, or fully tear the meshwork. For example, a catheter/conduit, probe, or wire (with or without a lumen) whose tip is 200-250 microns in outer diameter, but having a shaft that begins to flare outwards after 3 clock hours of Schlemm's canal (i.e., at about the 5 or 10 mm mark on the catheter/conduit) up to about 300, up to about 400, or up to about 500 microns, may be used, so that as the tip advances comfortably within Schlemm's canal, the enlarged shaft trails behind and ruptures the trabecular meshwork as it is advanced.

In yet further methods, tissue disruption may be accomplished by the ab-interno delivery of a suture throughout Schlemm's canal, which is then sufficiently tensioned to stretch the canal, disrupt the trabecular meshwork, and/or tear through the meshwork ("Ab interno Suture Trabeculotomy"). Here a tool including a grasping element may be employed for pulling the distal suture tip inwards as the cannula is being withdrawn from the eye, severing all 360 degrees or a segment of the trabecular meshwork, or for tying the suture ends together to provide tension on the meshwork without necessarily tearing it.

Figure 18A:
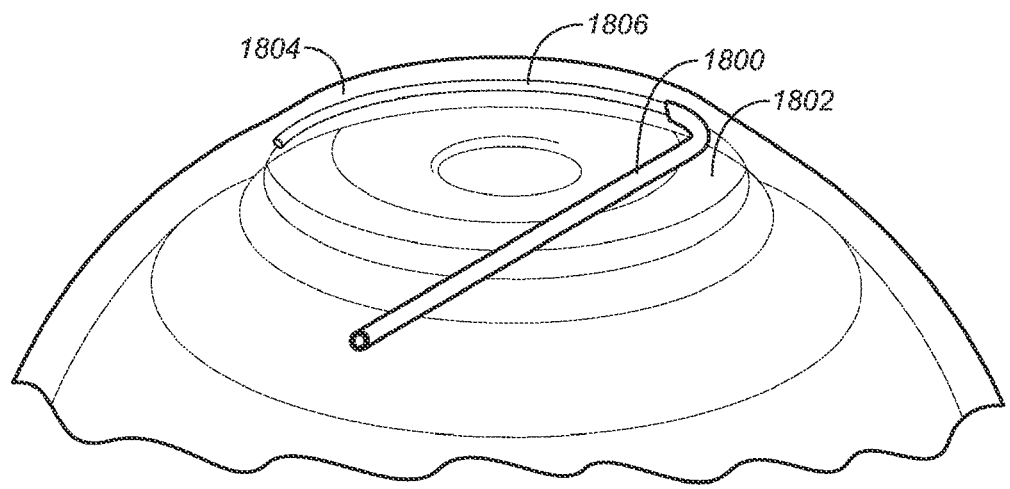
FIGS. 18A-18C illustrate an exemplary ab-interno method of cutting or tearing the trabecular meshwork.
Figure 18B:
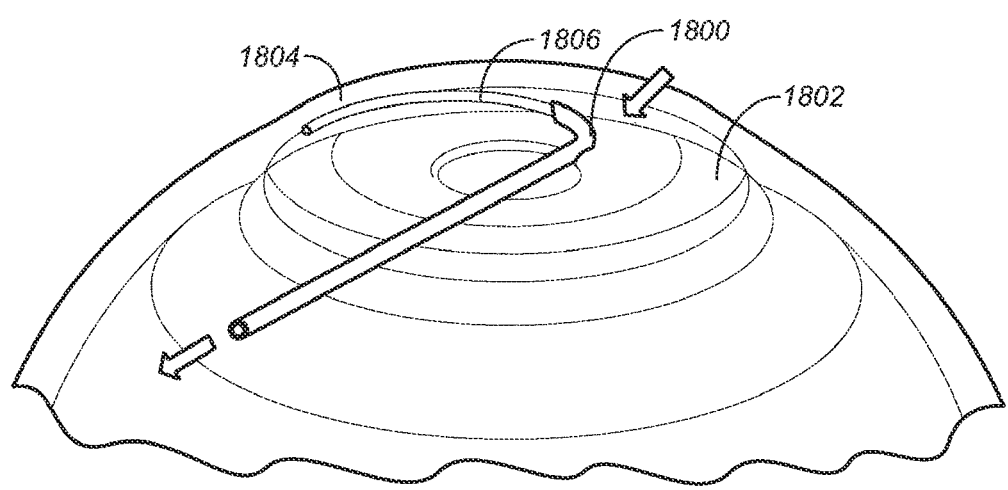
Figure 18C:
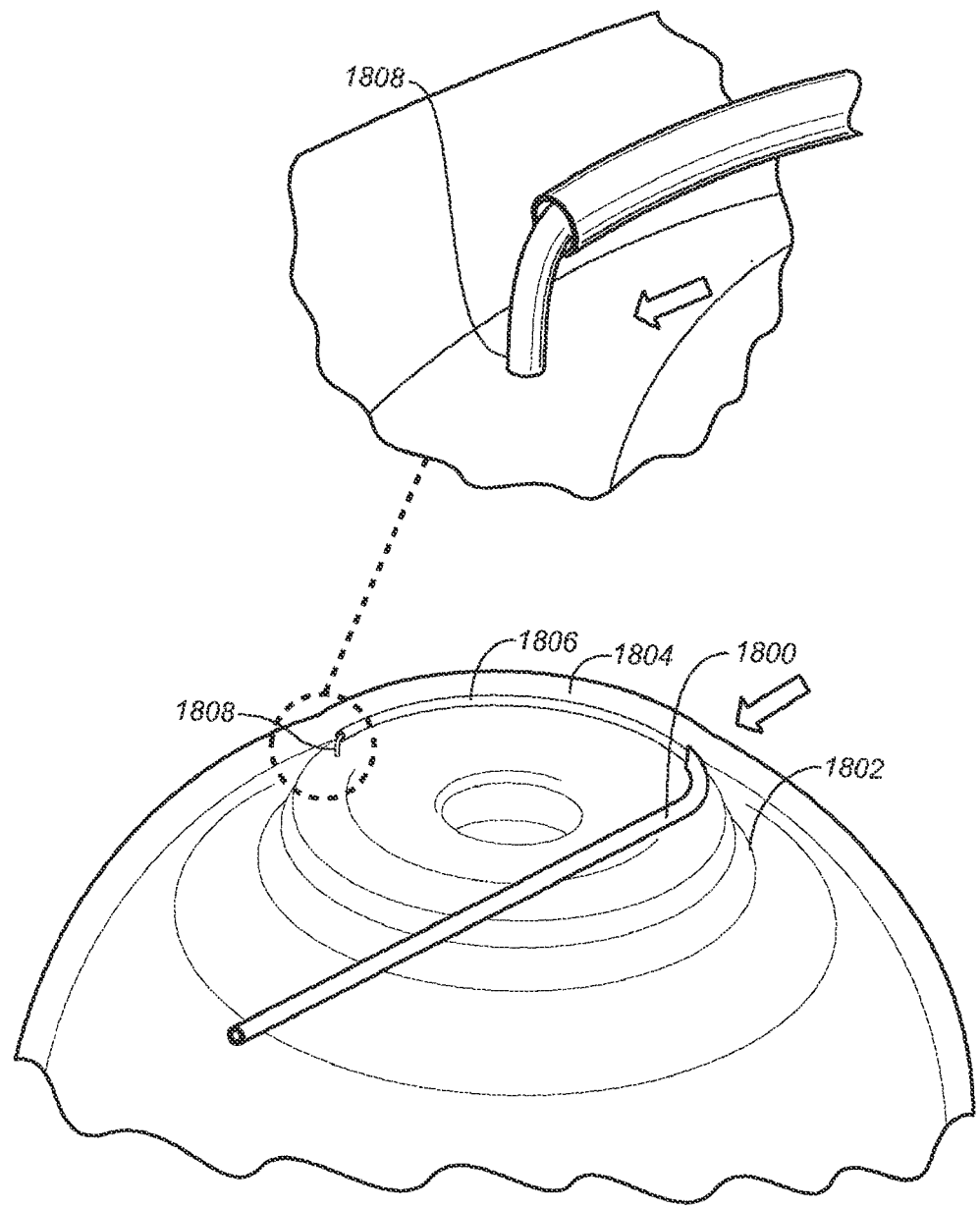

Customizing a body segment of the conduit proximal to the tip with a notch or notches or barbs that catch the meshwork as the distal tip is being guided and advanced along Schlemm's canal could also be used, thereby disrupting, partially tearing, fully tearing, and/or removing trabecular meshwork upon advancement. Additionally, an implant with edges specifically designed to cut the meshwork could be used. Still other methods for disrupting tissues may involve customizing the system (e.g., the conduit, any catheters or wires, probe tips, etc.) to catch or grasp the meshwork upon retraction after complete advancement through the canal. This may be done using a wire with a bent tip, hook, notch, or barb on its end that is advanced through the lumen of the catheter that then snags the meshwork upon retraction, tearing it along its length or removing it altogether, or solely with a metal or polymer wire or suture (no catheter) whose tip (and/or body) is hooked, notched, or barbed in such a way that it can be advanced into Schlemm's canal without tearing the meshwork but snags the meshwork upon retraction, tearing the meshwork and/or removing it completely. Referring to FIG. 18A, a cannula (1800) may be inserted into the anterior chamber (1802) and Schlemm's canal (1804), and a tool (e.g., a slidable conduit (1806)) may be advanced within the canal (1804). As shown in FIG. 18B, the slidable conduit (1806) can be retracted and withdrawn from the anterior chamber (1802) without retracting the cannula (1800). This action by itself may tear the trabecular meshwork. Alternatively, as shown in FIG. 18C, the conduit (1806) may be provided with a disruptive tool, e.g., a sharp-edged element (1808), that can cut or tear the trabecular meshwork while being retracted into the cannula (1800), which is held stationary. Exemplary sharp-edged elements may be a hook, wire, or any other suitable shape memory component that can extend from the cannula to tear, cut, or remove trabecular meshwork.

The configuration of the ocular delivery system may be advantageous in many different respects. In one aspect, the delivery system is capable of being used in an ab-interno method of implanting an ocular device in Schlemm's canal or an ab-interno method of delivering a fluid composition or a tool into the canal. In another aspect, the delivery system cannula is configured to allow easy and atraumatic access to Schlemm's canal. Furthermore, the delivery system is configured in a manner that gives the surgeon greater freedom of use, all in a single instrument. For example, the handle of the system is configured so that it can be used with either the right or left hand on either the right or left eye just by flipping over the handle or rotating the cannula. Furthermore, the delivery system is designed so that it is capable of being used with the right hand to access Schlemm's canal in a counterclockwise fashion, use with the left hand to access to Schlemm's canal in a clockwise fashion, or use with the left hand to access the canal in a counterclockwise fashion, etc. Thus, access to the canal from all four quadrants of the eye can be achieved. In yet a further respect, the delivery system comprises single-handed, single-operator controlled devices configured to provide a force sufficient to disrupt Schlemm's canal and surrounding tissues to improve flow through the trabeculocanalicular outflow pathway. The systems generally combine access cannulas, delivery conduits, conduit advancement mechanisms, disruptive tools, and viscoelastic fluids into a single device so that one person or one hand can advance the conduit or tool, or deliver the fluid.

The invention claimed is:

1. A device for delivering fluids to an eye comprising:
a cannula;
a handle disposed at a proximal end of the cannula and comprising a housing and a fluid reservoir at least partially housed therein, wherein the handle is capable of being held with a single hand of a user;
a flexible conduit slidably disposed within, and advanceable distally from, the cannula and around an arc of Schlemm's canal, the conduit comprising a lumen in fluid communication with the fluid reservoir; and
a loading component, wherein the fluid reservoir is finable via the loading component, and
wherein the device is configured to deliver fluid from the fluid reservoir to the eye via the conduit without a separate fluid delivery device in fluid communication with the conduit during fluid delivery.

2. The device of claim 1, wherein the fluid reservoir is moveable within the housing.

3. The device of claim 1, wherein the loading component comprises a coupling configured to reversibly couple to the separate fluid delivery device.

4. The device of claim 1, wherein the cannula is configured to rotate.

5. The device of claim 1, wherein a length of the handle is about 4 inches to about 10 inches.

6. The device of claim 1, wherein an outer diameter of the conduit is about 150 microns to about 500 microns.

7. The device of claim 1, wherein the conduit is configured to be advanced around a 180 degree arc of Schlemm's canal.

8. The device of claim 1, wherein the handle further comprises an actuator for moving the conduit, wherein the actuator is accessible by a finger on the single hand of the user while holding the handle.

9. The device of claim 8, wherein the device is configured to deliver fluid from the fluid reservoir by decreasing the volume of the fluid reservoir.

10. The device of claim 8, wherein the actuator comprises a slide.

11. The device of claim 1, wherein the conduit is configured to be advanced around about a 360 degree arc of Schlemm's canal.

12. A device for delivering fluids to an eye comprising:
a cannula;
a handle comprising a housing and a fluid reservoir at least partially housed and moveable therein, wherein the cannula is coupled to a distal end of the housing, wherein the handle is capable of being held by a single hand of a user; and
a flexible conduit slidably disposed within, and advanceable distally from, the cannula and around an arc of Schlemm's canal, the conduit comprising a lumen in fluid communication with the fluid reservoir,
wherein the handle further comprises an actuator configured to deliver fluid through the conduit to Schlemm's canal, the actuator comprises a slide, and movement of the slide correspondingly moves an elongate member to deliver fluid from the fluid reservoir into Schlemm's canal, and wherein the device is configured to deliver fluid from the fluid reservoir into Schlemm's canal via the conduit without a syringe in fluid communication with the conduit during fluid delivery.

13. The device of claim 12, wherein the device is configured to deliver fluid from the fluid reservoir by decreasing a volume of the fluid reservoir.

14. The device of claim 12, wherein the slide is coupled to the elongate member and the elongate member is positioned within the handle.

15. The device of claim 14, wherein the elongate member comprises a lumen therethrough configured to deliver fluid to the conduit.

16. The device of claim 12, wherein the conduit is configured to be advanced around a 90 degree arc of Schlemm's canal.

17. The device of claim 12, wherein the conduit is configured to be advanced around a 180 degree arc of Schlemm's canal.

18. The device of claim 12, wherein a length of the handle is about 4 inches to about 10 inches.

19. The device of claim 12, wherein the device further comprises a loading component, and wherein the fluid reservoir is fillable via the loading component.

20. The device of claim 12, wherein the conduit is configured to be advanced around about a 360 degree arc of Schlemm's canal.

21. A device for delivering fluids to an eye comprising:
a cannula;
a handle comprising a housing and a fluid reservoir at least partially housed and moveable therein, wherein the handle is capable of being held by a single hand of a user;
a flexible conduit slidably disposed within, and advanceable distally from, the cannula, and around an arc of Schlemm's canal; and
a loading component extending from the fluid reservoir and passing through the housing of the handle, wherein a portion of the loading component extends beyond the housing, and
wherein the device is configured to deliver fluid from the fluid reservoir to the eye via the conduit without a separate fluid delivery device in fluid communication with the fluid reservoir during fluid delivery.

22. The device of claim 21, wherein the cannula is disposed at a distal end of the housing.

23. The device of claim 21, wherein the portion of the loading component extending beyond the housing of the handle comprises a coupling on an end thereof, the coupling configured to reversibly couple to the separate fluid delivery device.

24. The device of claim 21, wherein an outer diameter of the flexible conduit is about 150 microns to about 500 microns.

25. The device of claim 21, wherein the handle further comprises a lock.

26. The device of claim 21, wherein the device is configured to deliver fluid from the fluid reservoir by decreasing the volume of the fluid reservoir.

27. The device of claim 21, wherein the cannula is configured to rotate.

28. The device of claim 21, wherein the conduit is configured to be advanced around a 180 degree arc of Schlemm's canal.

29. The device of claim 21, wherein a length of the handle is about 4 inches to about 10 inches.

30. The device of claim 21, wherein the conduit is configured to be advanced around about a 360 degree arc of Schlemm's canal.

* * * * *

UNITED STATES PATENT AND TRADEMARK OFFICE
CERTIFICATE OF CORRECTION

| | | |
|---|---|---|
| PATENT NO. | : 12,042,428 B2 | Page 1 of 1 |
| APPLICATION NO. | : 18/130354 | |
| DATED | : July 23, 2024 | |
| INVENTOR(S) | : David Y. Badawi et al. | |

It is certified that error appears in the above-identified patent and that said Letters Patent is hereby corrected as shown below:

In the Claims

At Column 32, Claim number 1, Line numbers 23-24, read:
"a loading component, wherein the fluid reservoir is finable via the loading component, and"

Should read:
-- a loading component, wherein the fluid reservoir is fillable via the loading component, and --

Signed and Sealed this
Twentieth Day of May, 2025

Coke Morgan Stewart
*Acting Director of the United States Patent and Trademark Office*